(12) United States Patent  
Schultheiss et al.

(10) Patent No.: US 11,970,447 B2  
(45) Date of Patent: Apr. 30, 2024

(54) CRYSTALLINE SALTS OF PSILOCIN

(71) Applicant: Canna-Chemistries LLC, Vincennes, IN (US)

(72) Inventors: Nate Schultheiss, West Lafayette, IN (US); Nico Setiawan, Lafayette, IN (US); Lisa M. McCracken, Lafayette, IN (US); David Jonaitis, Brookston, IN (US)

(73) Assignee: CANNA-CHEMISTRIES LLC, Vincennes, IN (US)

( * ) Notice: Subject to any disclaimer, the term of this patent is extended or adjusted under 35 U.S.C. 154(b) by 0 days.

(21) Appl. No.: 17/751,998

(22) Filed: May 24, 2022

(65) Prior Publication Data

US 2022/0380308 A1    Dec. 1, 2022

Related U.S. Application Data

(60) Provisional application No. 63/310,703, filed on Feb. 16, 2022, provisional application No. 63/244,610, filed on Sep. 15, 2021, provisional application No. 63/240,092, filed on Sep. 2, 2021, provisional application No. 63/192,266, filed on May 24, 2021.

(51) Int. Cl.  
*C07D 209/16* (2006.01)  
*A61P 25/18* (2006.01)

(52) U.S. Cl.  
CPC ............ *C07D 209/16* (2013.01); *A61P 25/18* (2018.01); *C07B 2200/13* (2013.01)

(58) Field of Classification Search  
CPC .... C07D 209/16; C07B 2200/13; C07C 63/08  
See application file for complete search history.

(56) References Cited

U.S. PATENT DOCUMENTS 11,312,684 B1 * 4/2022 Nichols ................ C07D 209/16  
2022/0388956 A1 * 12/2022 Short ................... C07D 209/16

FOREIGN PATENT DOCUMENTS

GB            912715 A   * 12/1962  
WO       2019081764 A1     5/2019  
WO       2022173888 A1     8/2022

OTHER PUBLICATIONS

Salts of Therapeutic Agents: Chemical, Physicochemical, and Biological Considerations Molecules 2018, 23, 1719 (Year: 2018).*  
H.G. Brittain, in Polymorphism in Pharmaceutical Solids (H.G. Brittain ed., 2nd ed., 2009) (Year: 2009).*  
Conformational Behavior of Cinchonidine in Different Solvents: A Combined NMR and ab Initio Investigation, J. Am. Chem. Soc. 1998, 120, 49, 12920-12926 (Year: 1998).*  
Advanced Methodologies for Pharmaceutical Salt Synthesis, Crystal Growth & Design, 1358-1374 (2021) (Year: 2021).*

(Continued)

*Primary Examiner* — Amy C Bonaparte  
*Assistant Examiner* — Lauren Wells  
(74) *Attorney, Agent, or Firm* — Jeffrey N. Townes; Cozen O'Connor

(57) ABSTRACT

Crystalline salts of psilocin are disclosed. The beneficial and therapeutic uses of the crystalline psilocin salts and of compositions containing the crystalline psilocin salts are also disclosed. The disclosure sets out methods of making and characterizing the crystalline psilocin salts.

18 Claims, 50 Drawing Sheets

XRPD pattern of the psilocin stearate salt 10

(56) References Cited

OTHER PUBLICATIONS

Solid state thermomechanical engineering of high quality pharmaceutical salts via solvent free continuous processing Green Chemistry, 540-540 (2020) (Year: 2020).*
Diversity in Single- and Multiple-Component Crystals. The Search for and Prevalence of Polymorphs and Cocrystals Crystal Growth & Design, 1007-1026 (2007) (Year: 2007).*
Stahl et al., eds., "Appendix" in Handbook of Pharmaceutical Salts: Properties, Selection, and Use (2002).
Stahl et al. "Chapter 12: Monographs on Acids and Bases" in Handbook of Pharmaceutical Salts: Properties, Selection, and Use, Sthal et al., eds., (2002).
Stahl et al., eds., Excerpts from Handbook of Pharmaceutical Salts: Properties, Selection, and Use, consisting of the Introduction and pp. 103-104, 109-110, 120, 154-157, and 163-170 (2008).
Kuhnert-Brandstatter et al., "Polymorphe Modifikationen und Solvate von Psilocin und Psilocybin," Archiv Der Pharmazie, vol. 309, No. 8, (Jan. 1, 1976), pp. 625-631.
Shirota et al., "Concise Large-Scale Synthesis of Psilocin and Psilocybin, Principal Hallucinogenic Constituents of 'Magic Mushroom'," Journal of Natural Products, vol. 66, No. 6, (Jun. 1, 2003), pp. 885-887.
Nichols, "Psilocybin: from ancient magic to modern medicine," The Journal of Antibiotics, vol. 73, No. 10, (May 12, 2020), pp. 679-686.

* cited by examiner

FIG. 1: XRPD pattern of the psilocin benzoate salt 1
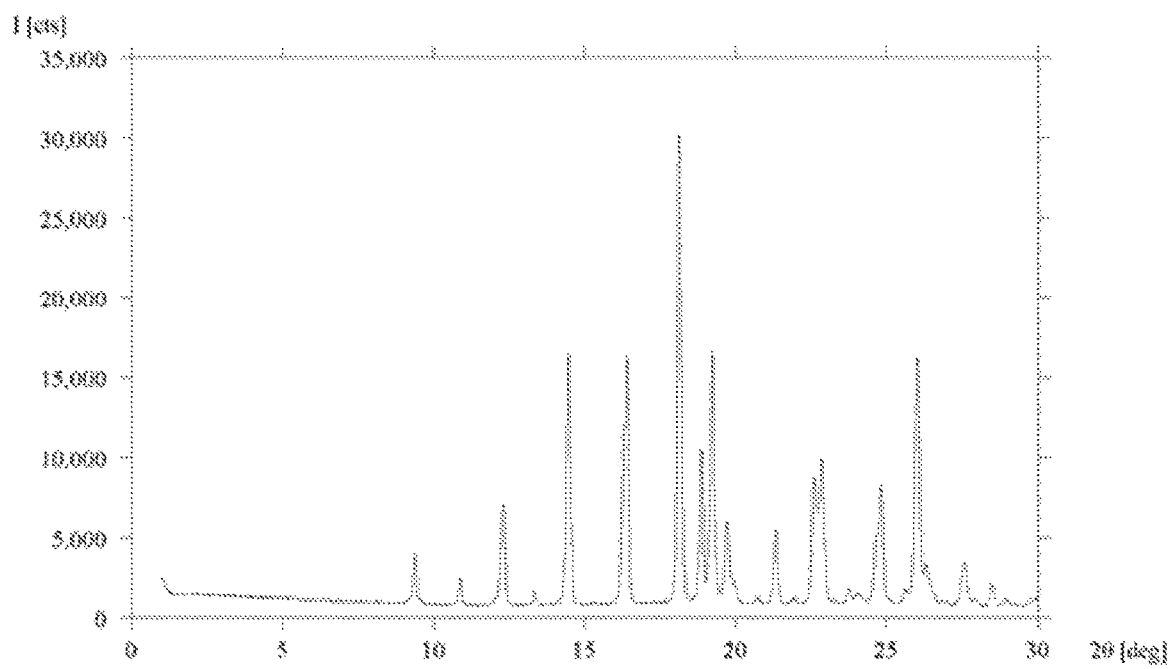

FIG. 2: XRPD pattern indexing of the psilocin benzoate salt 1
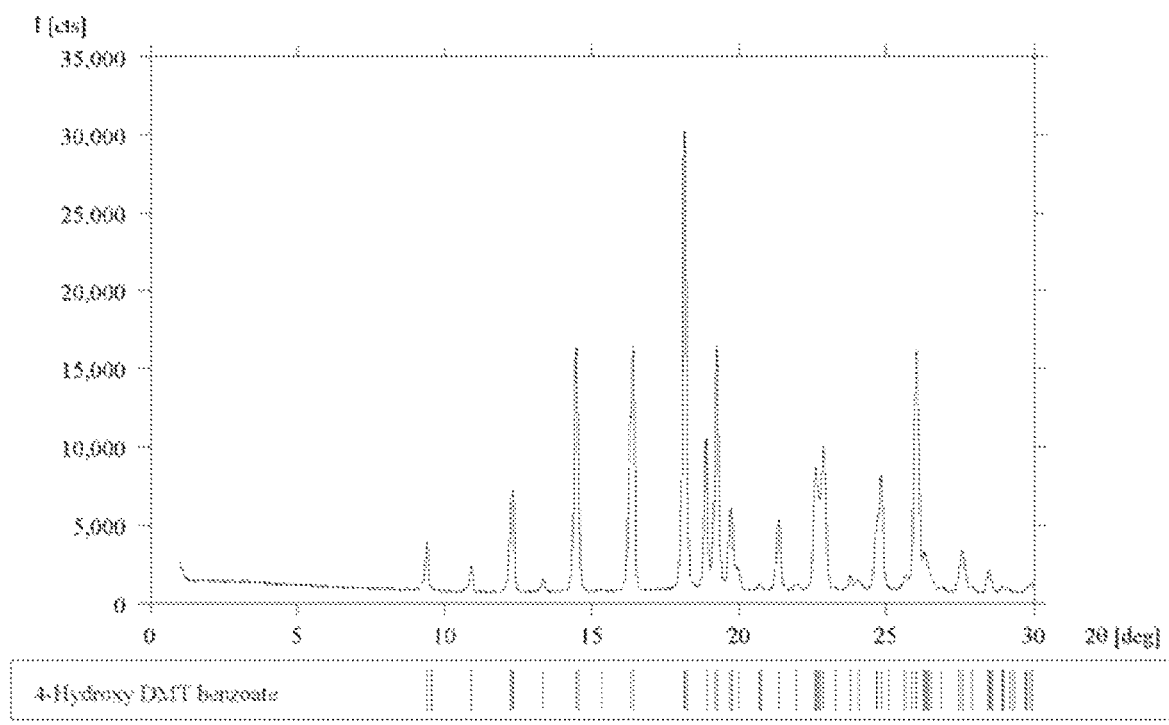

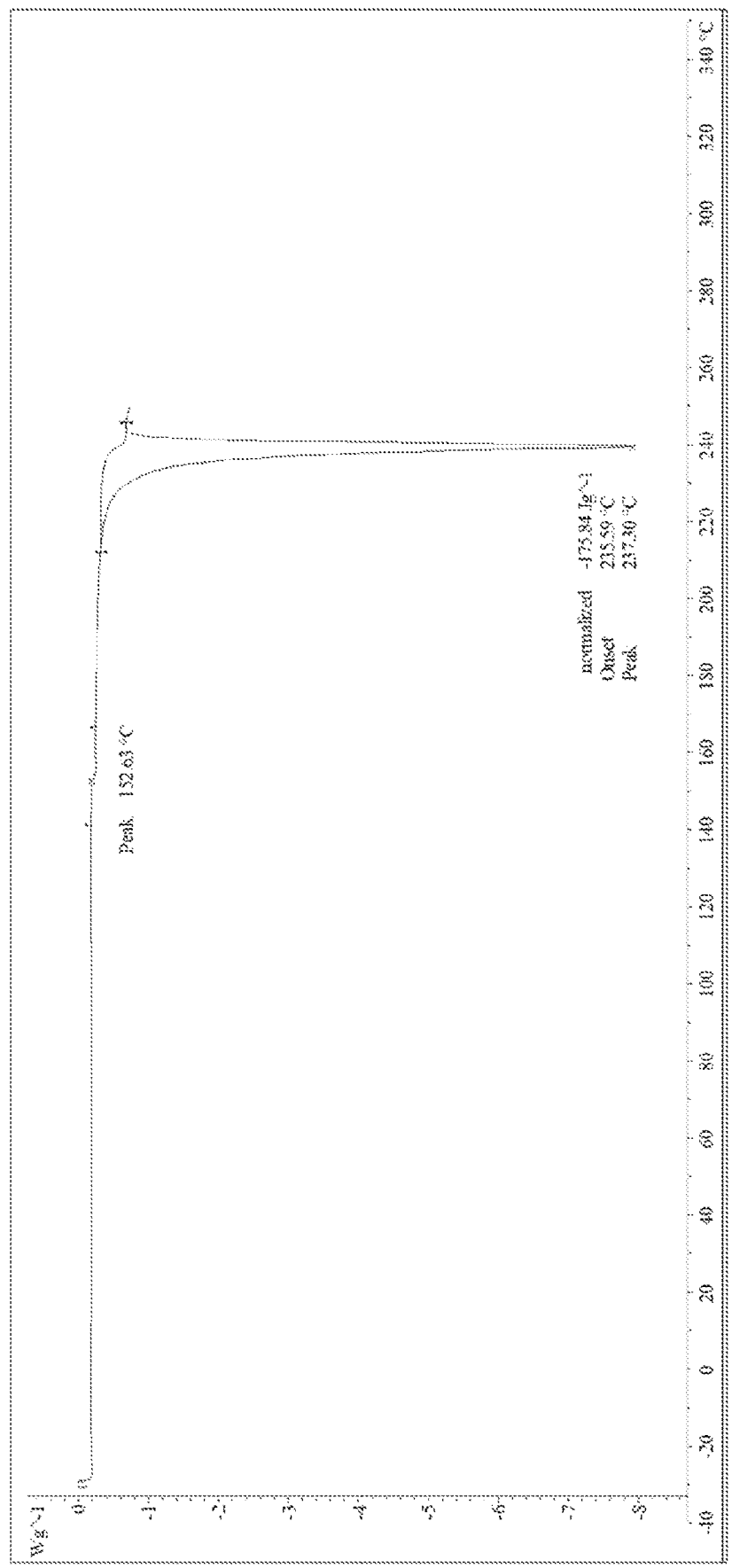
FIG. 3: DSC trace for the psilocin benzoate salt 1

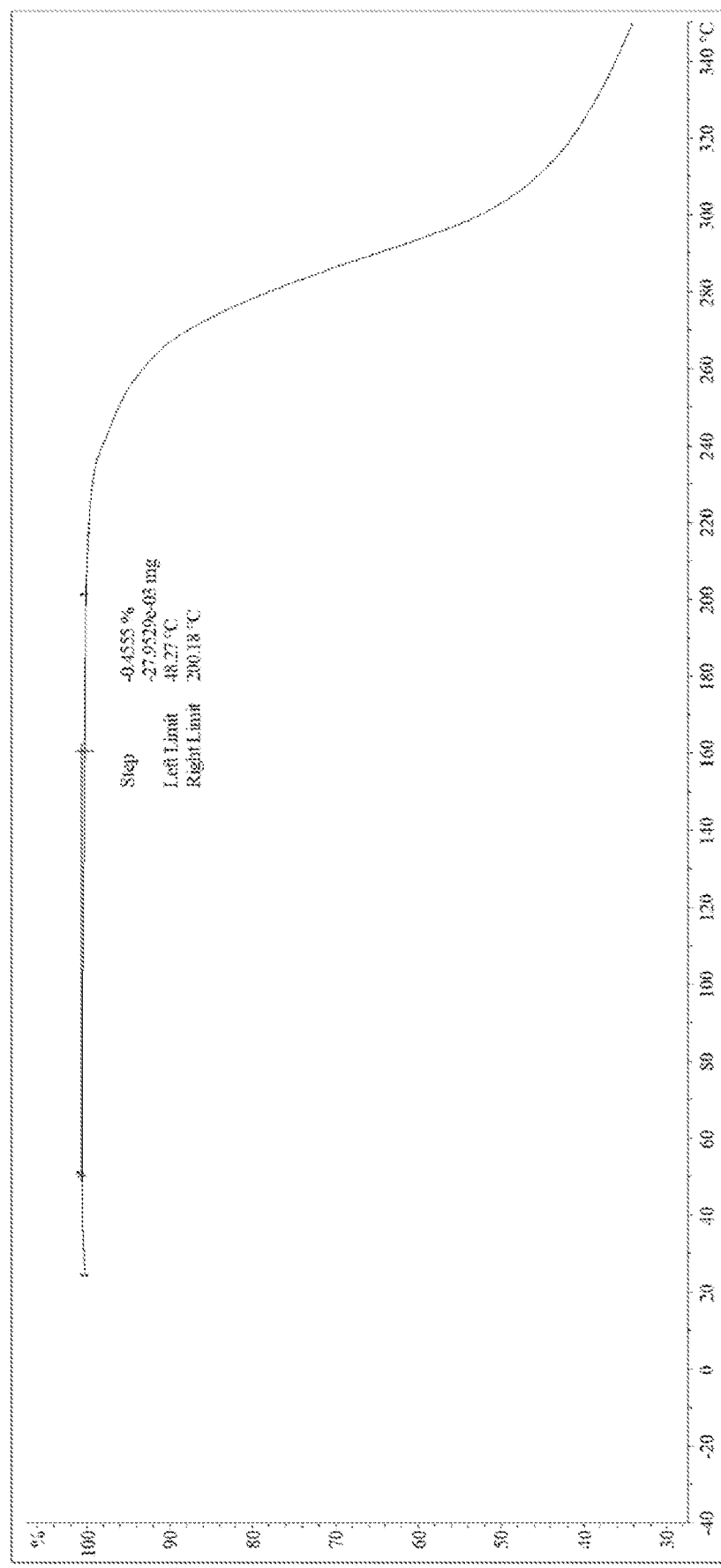
FIG. 4: TGA trace for the psilocin benzoate salt 1

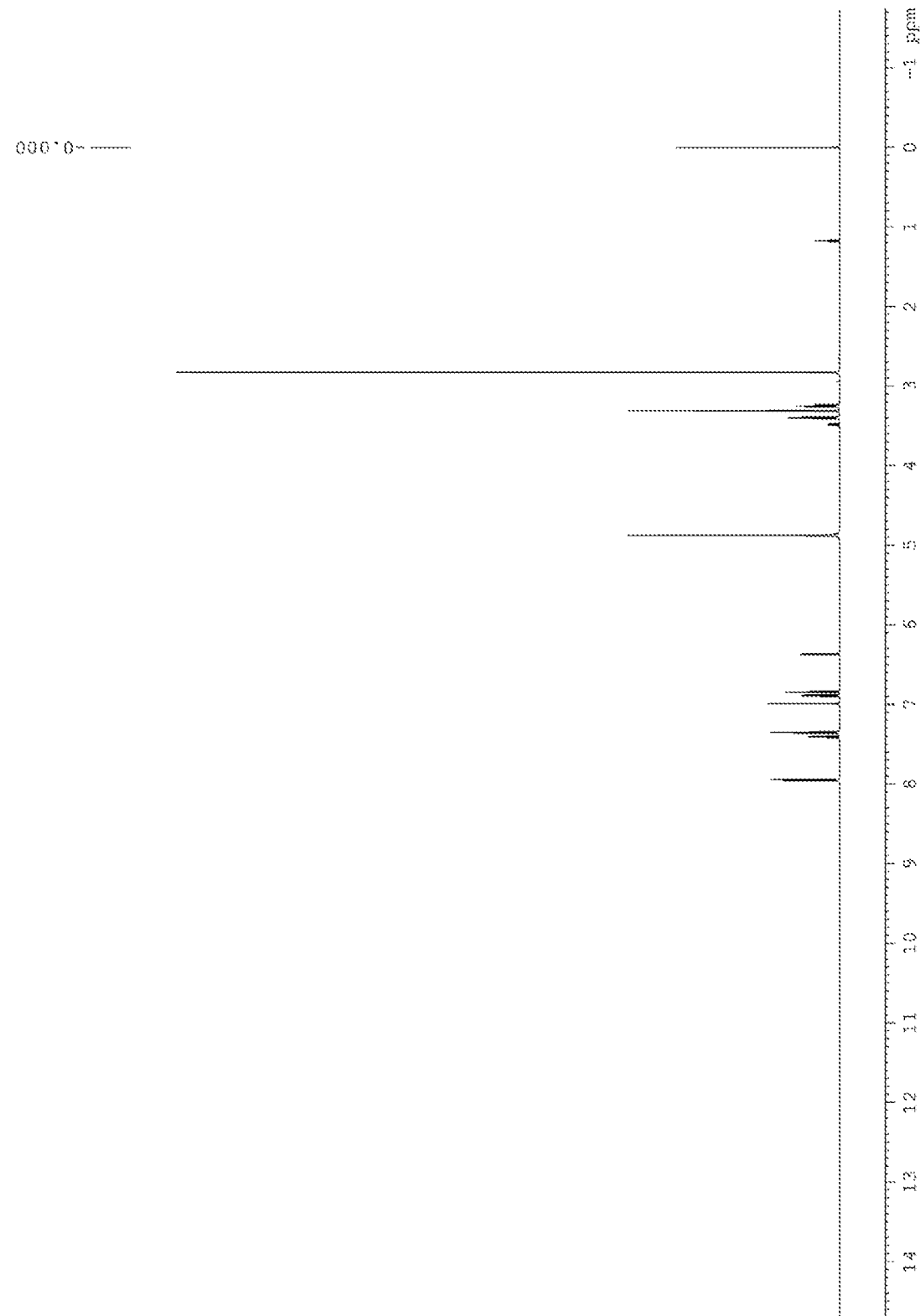
FIG. 5: ¹H NMR spectrum of the psilocin benzoate salt 1

FIG. 6: XRPD pattern of the psilocin nicotinate salt 2
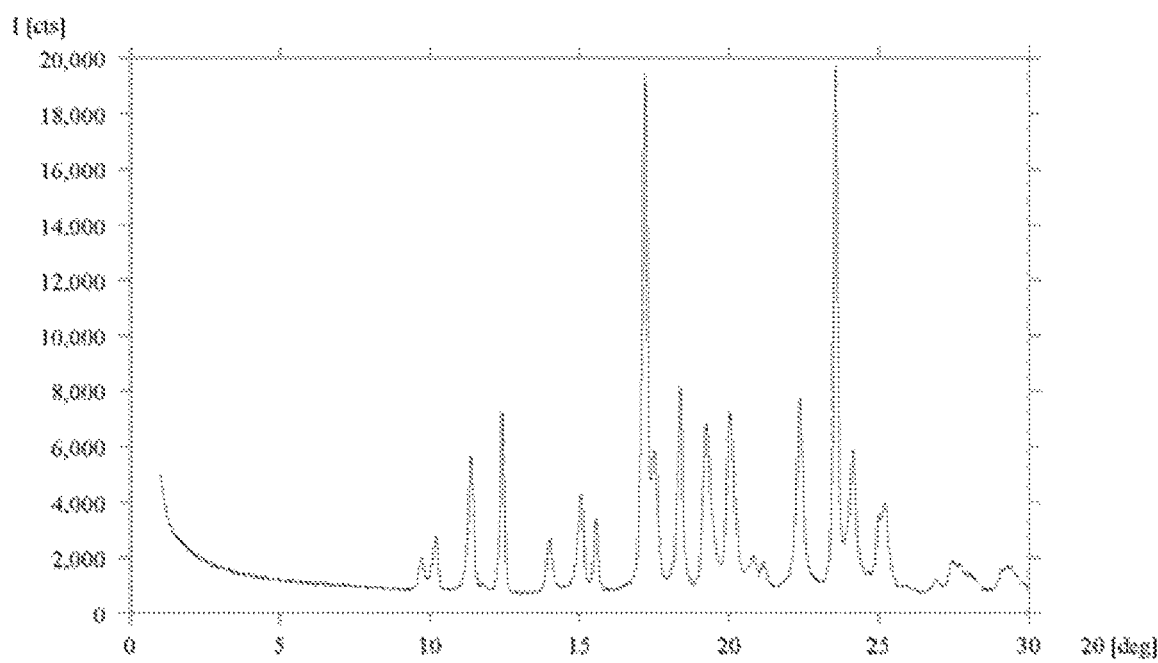

FIG. 7: XRPD pattern indexing of the psilocin nicotinate salt 2
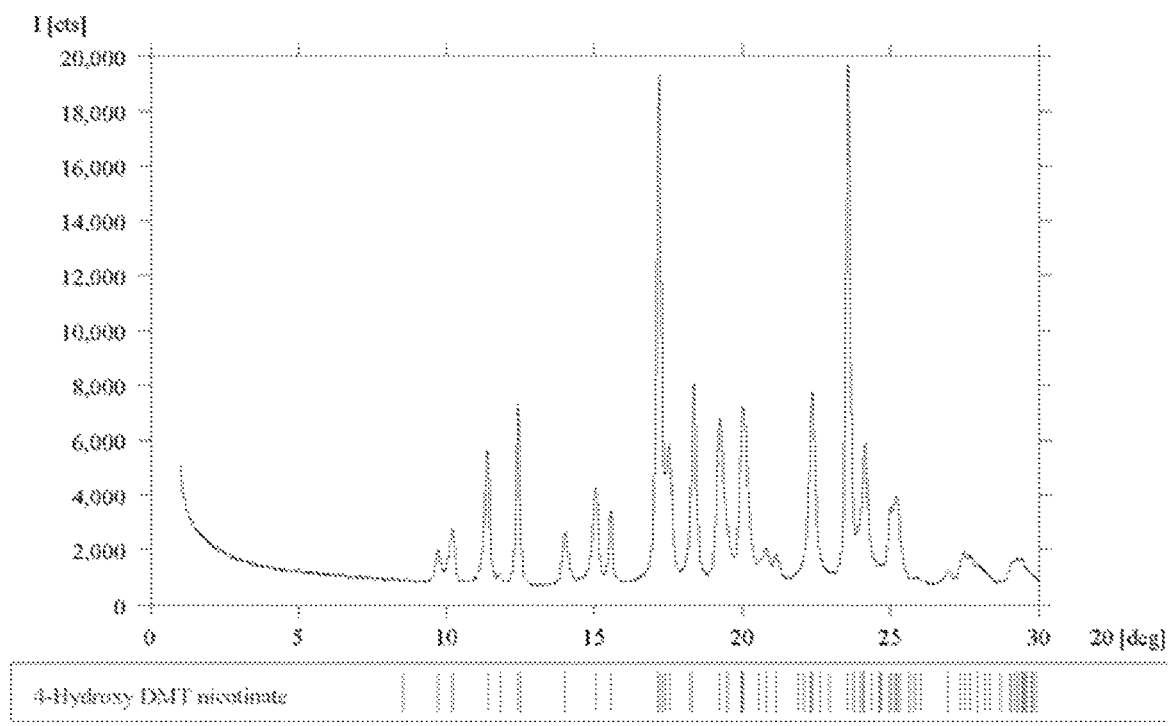

FIG. 8: DSC trace for the psilocin nicotinate salt 2
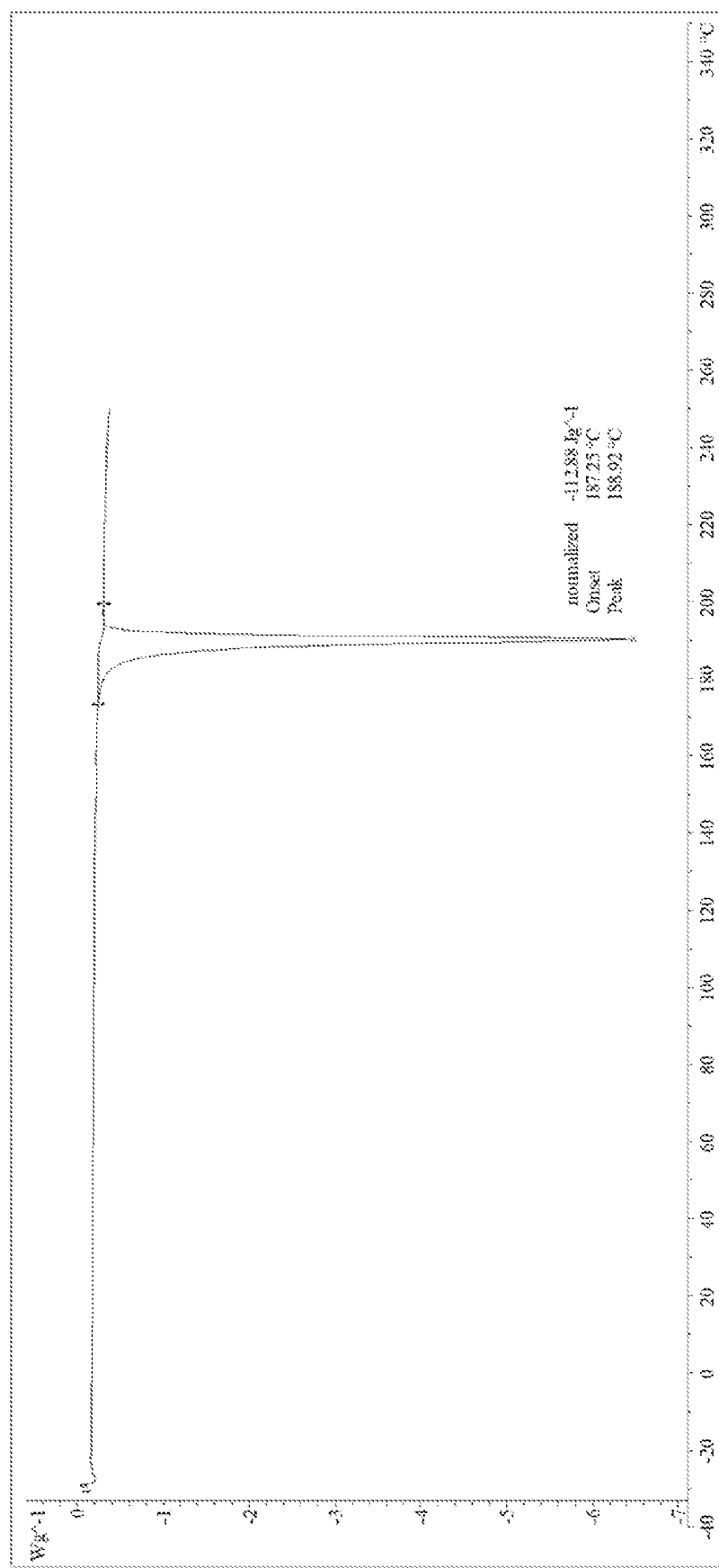

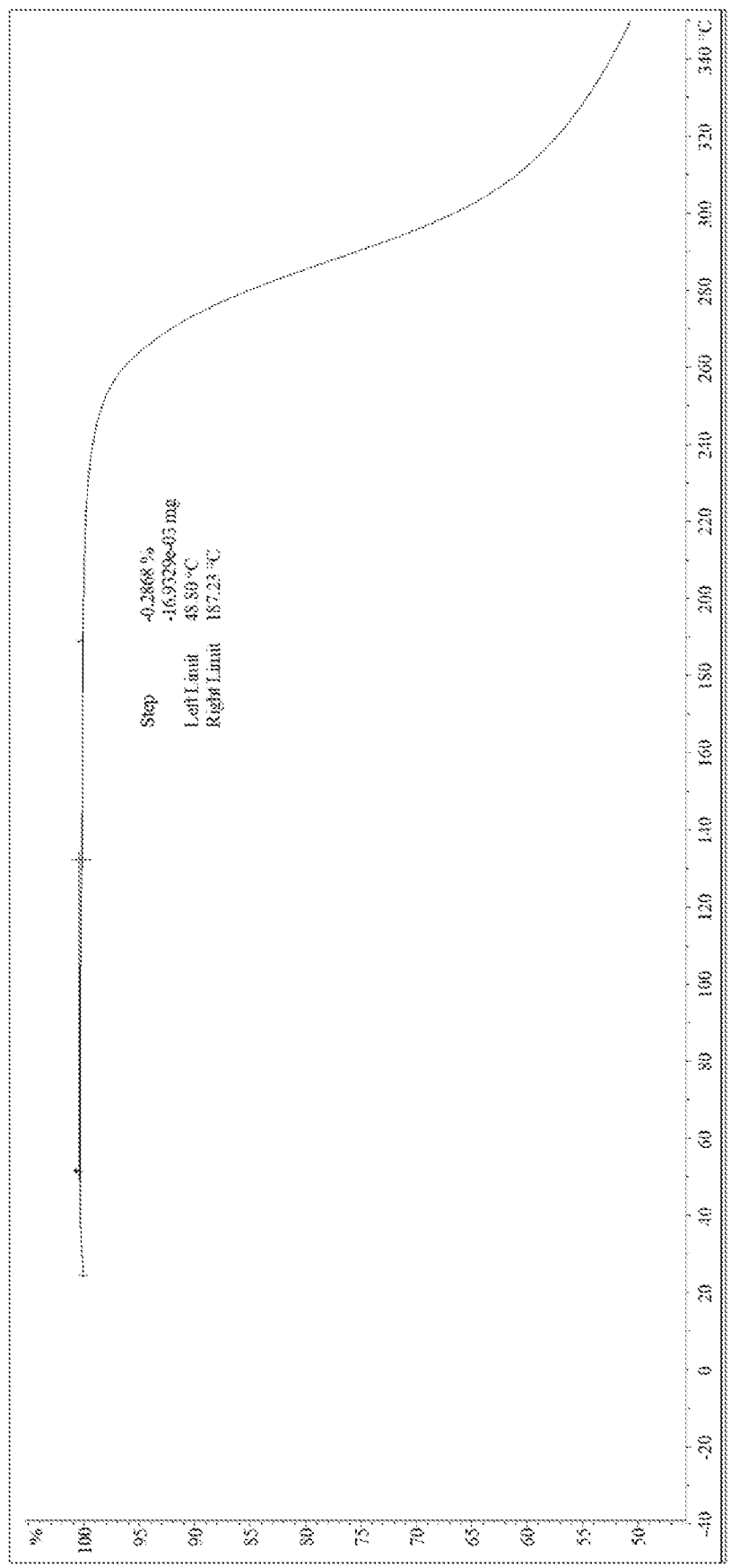
FIG. 9: TGA trace for the psilocin nicotinate salt 2

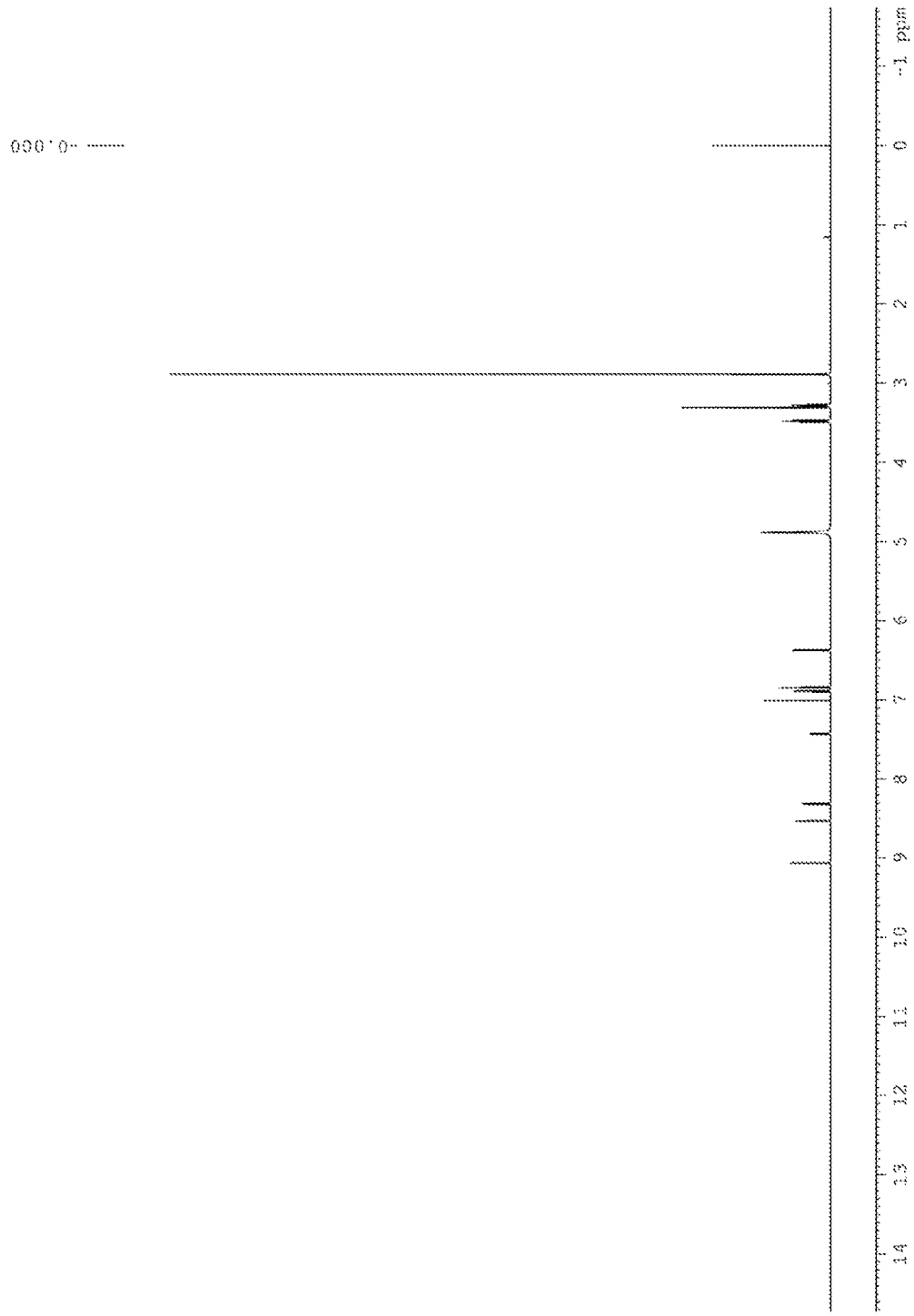
FIG. 10: $^1$H NMR spectrum of the psilocin nicotinate salt 2

FIG. 11: XRPD pattern of the psilocin tartrate salt 3
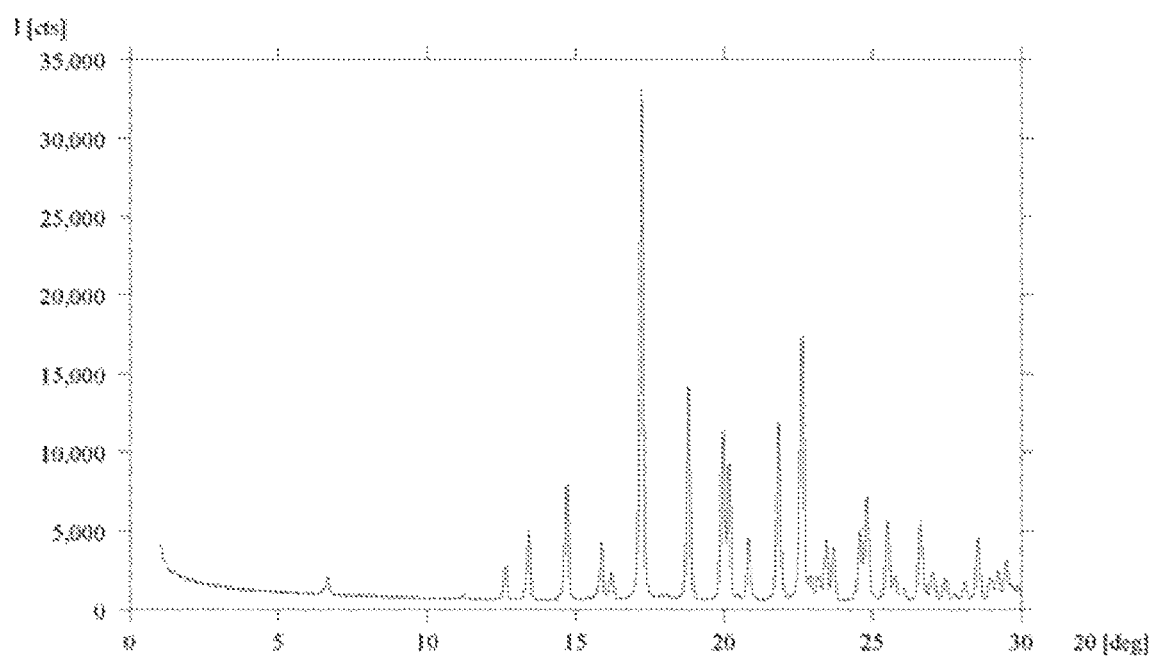

FIG. 12: XRPD pattern indexing of the psilocin tartrate salt 3
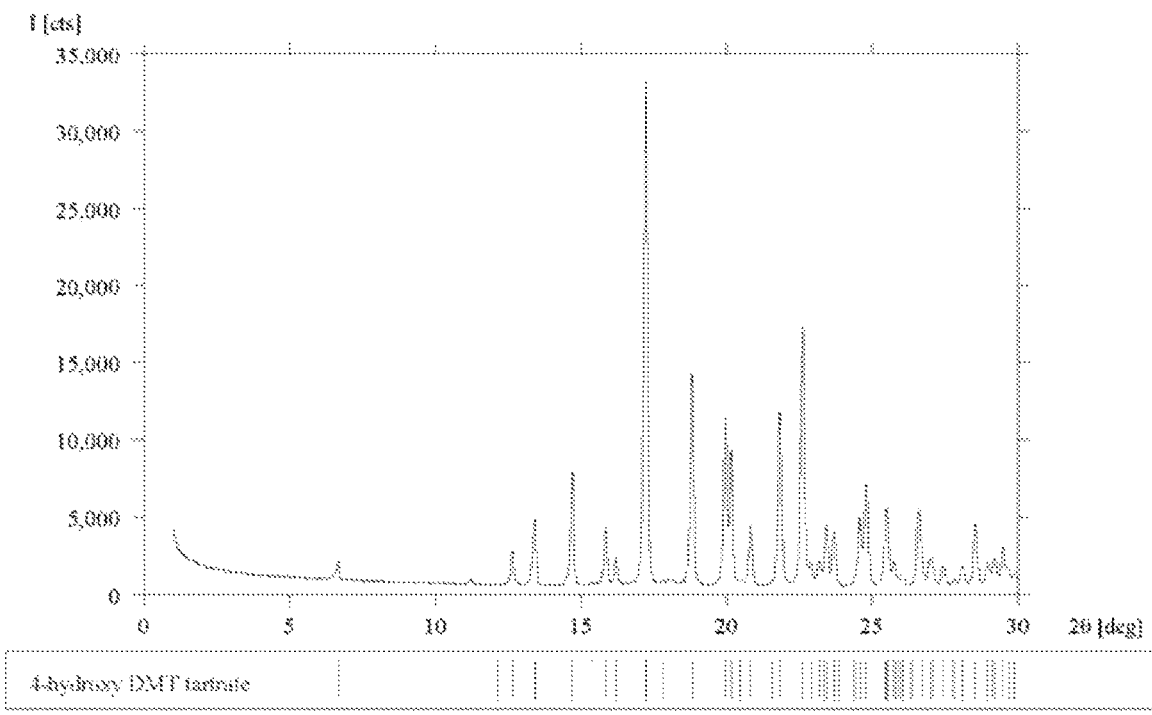

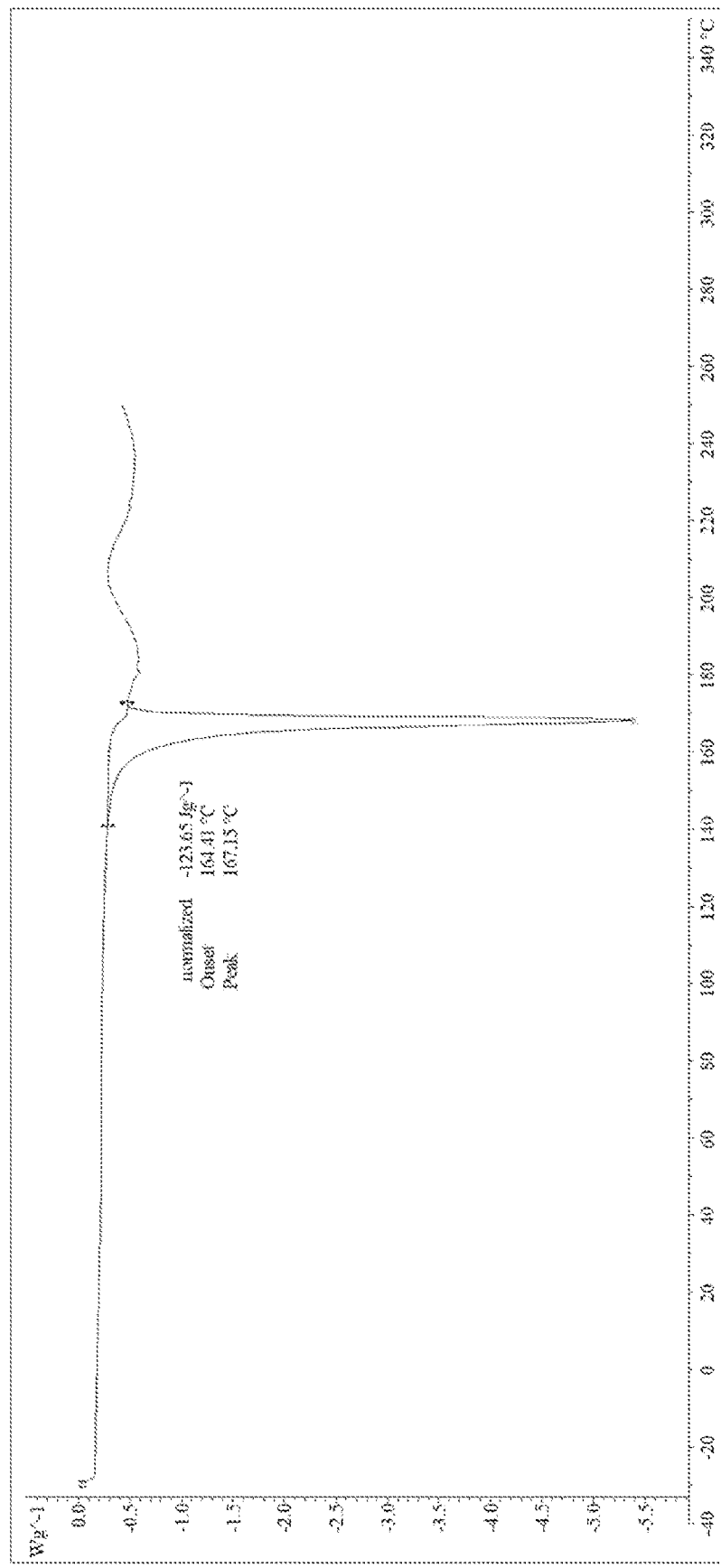
FIG. 13: DSC trace for the psilocin tartrate salt 3

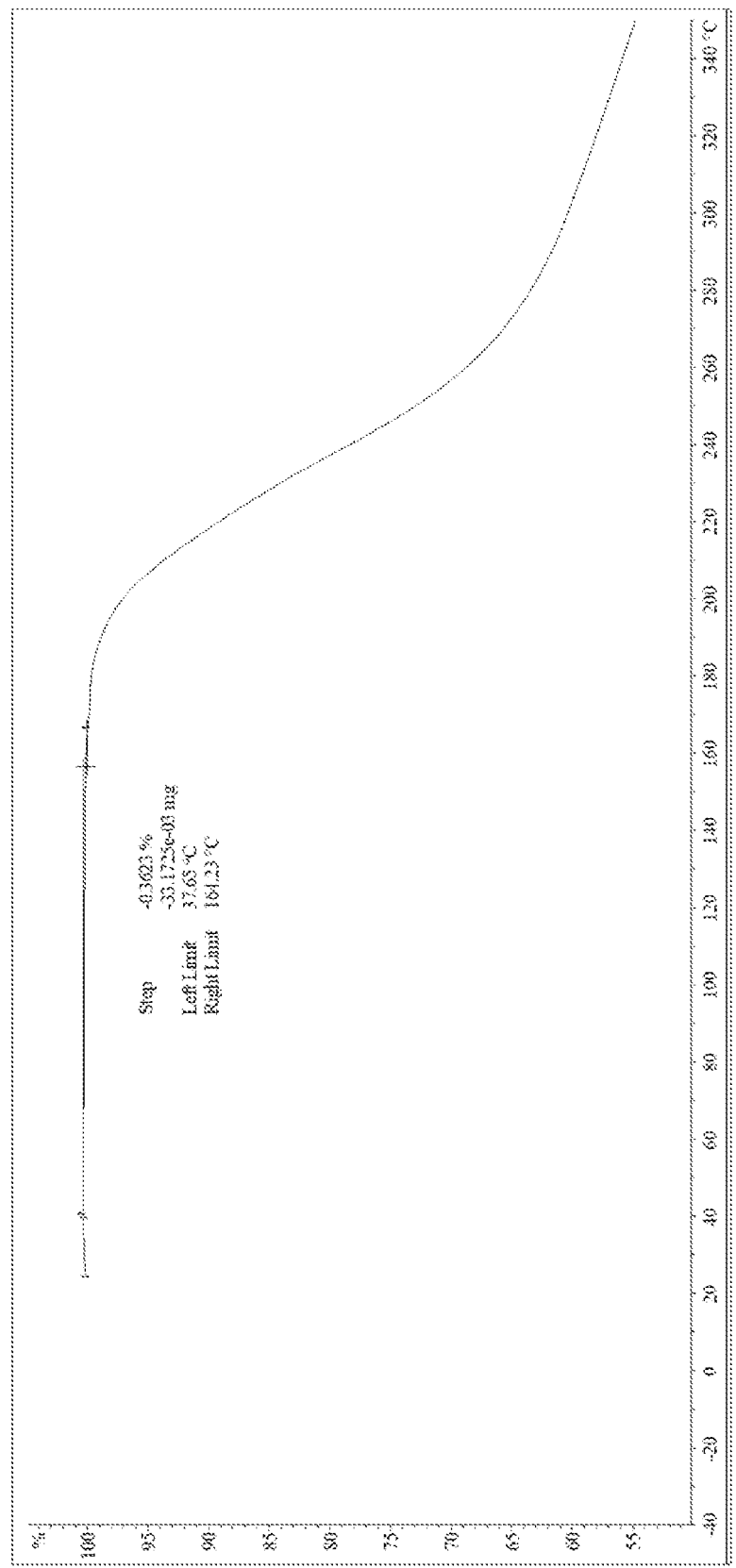
FIG. 14: TGA trace for the psilocin tartrate salt 3

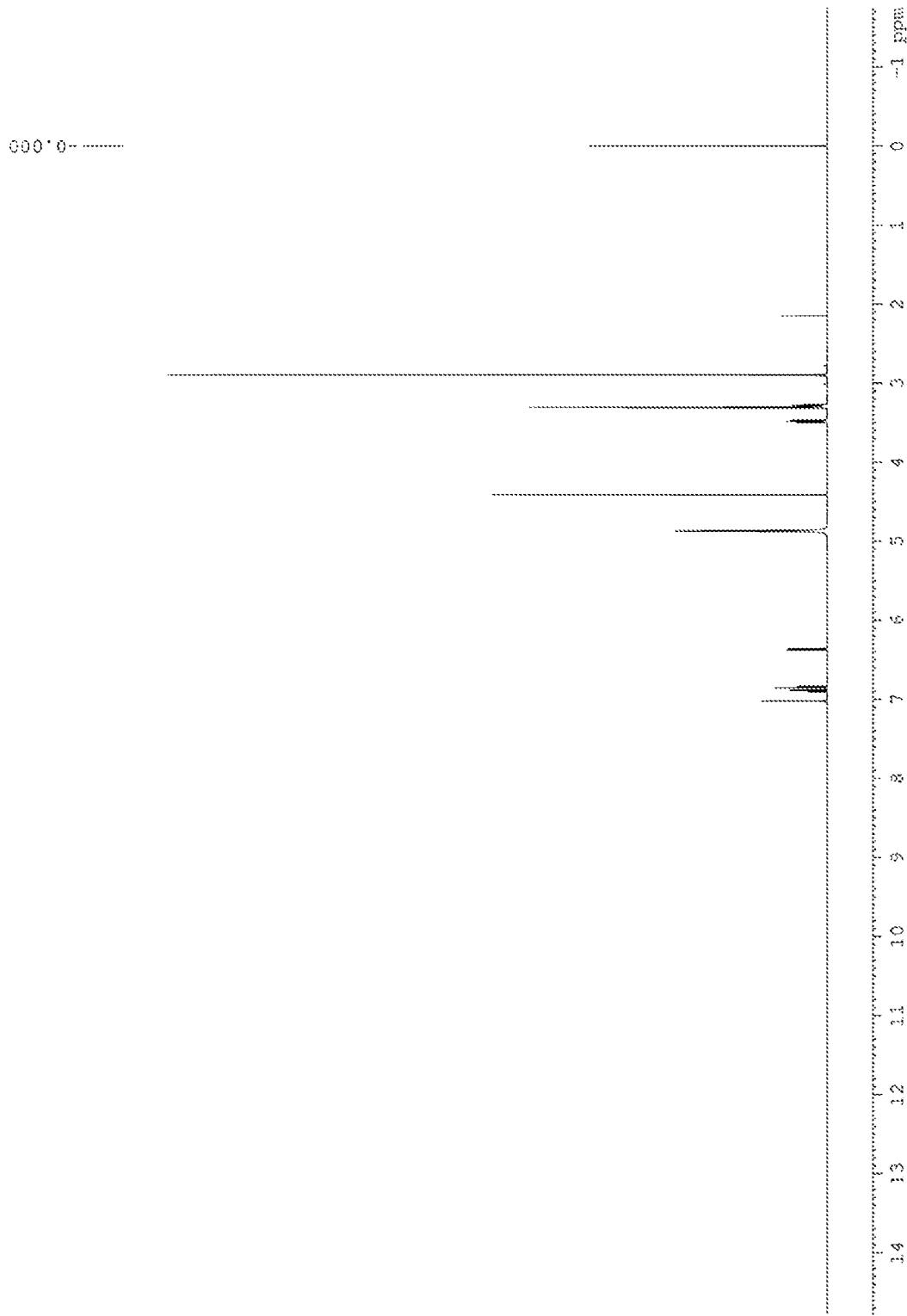
FIG. 15: $^1$H NMR spectrum of the psilocin tartrate salt 3

FIG. 16: XRPD pattern of the hemiacetone solvate of the psilocin hemiadipate salt 4
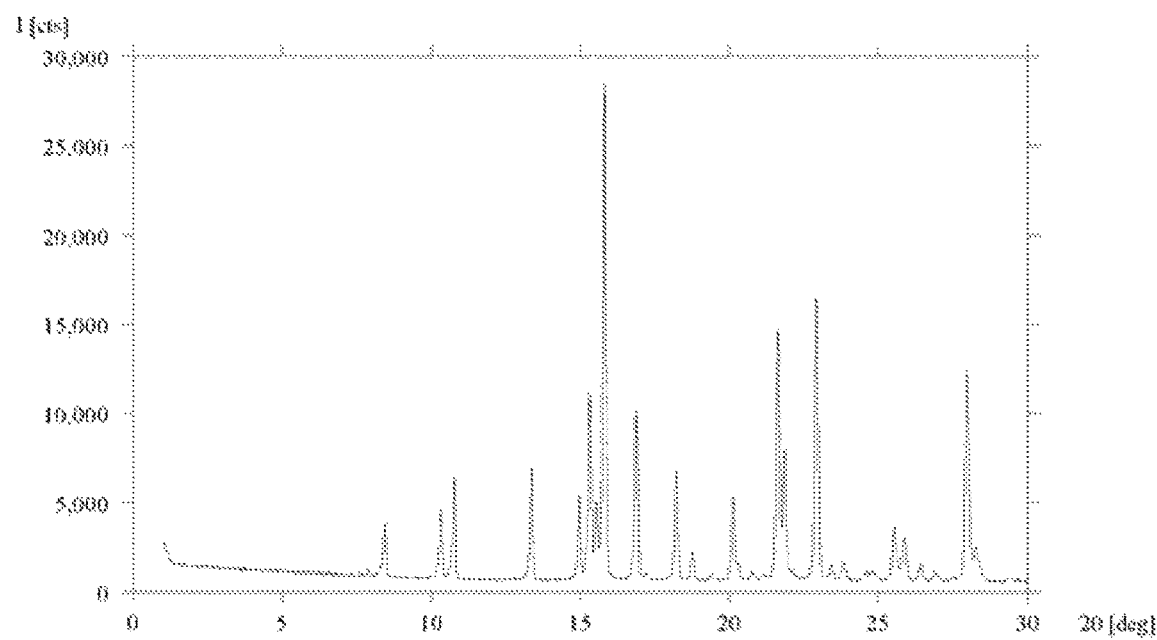

FIG. 17: XRPD pattern indexing of the hemiacetone solvate of the psilocin hemiadipate salt 4
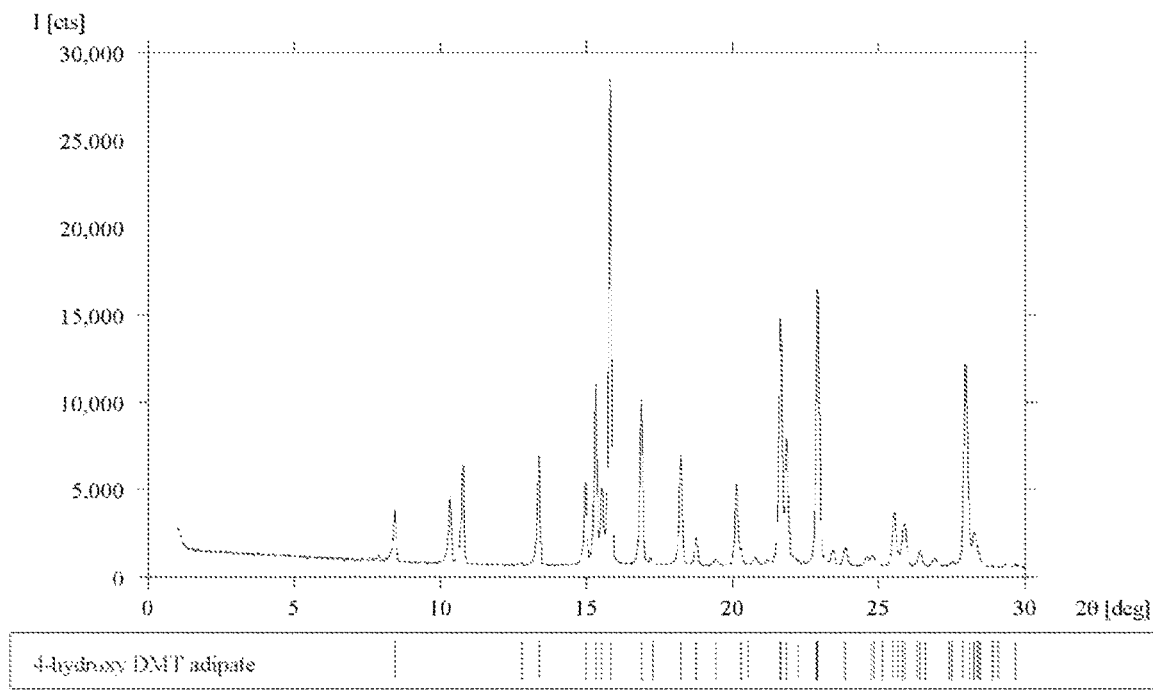

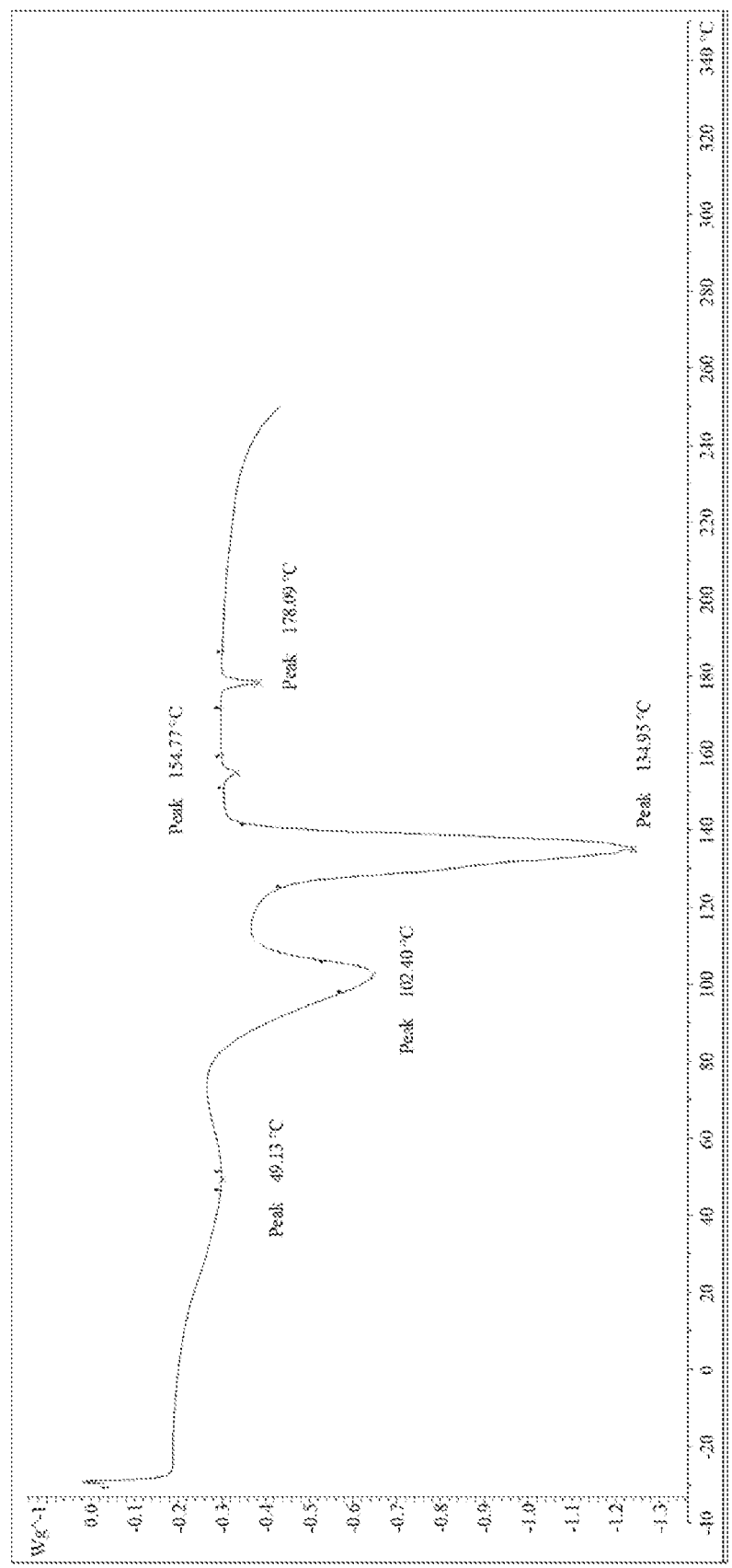
FIG. 18: DSC trace for the hemiacetone solvate of the psilocin hemiadipate salt 4

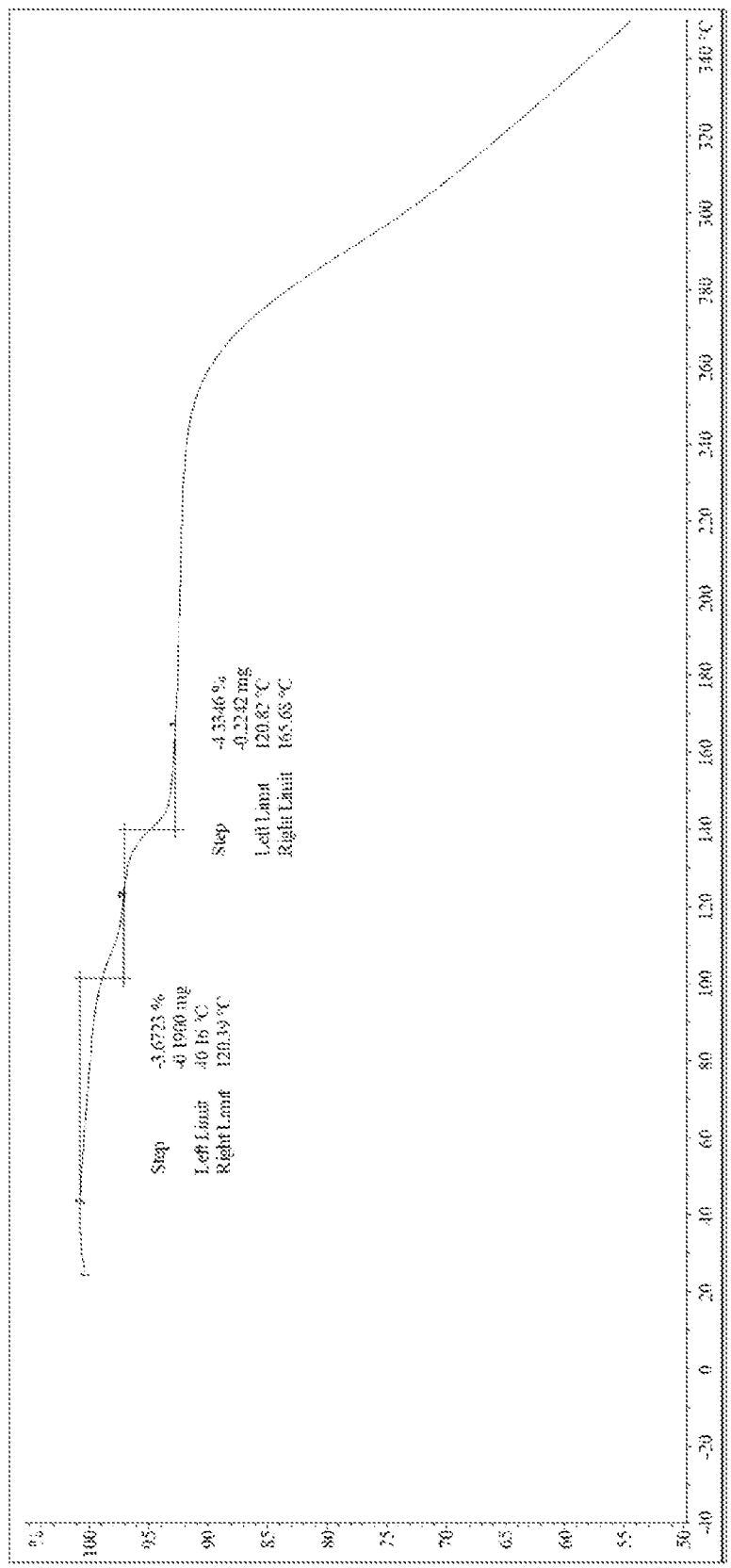
FIG. 19: TGA trace for the hemiacetone solvate of the psilocin hemiadipate salt 4

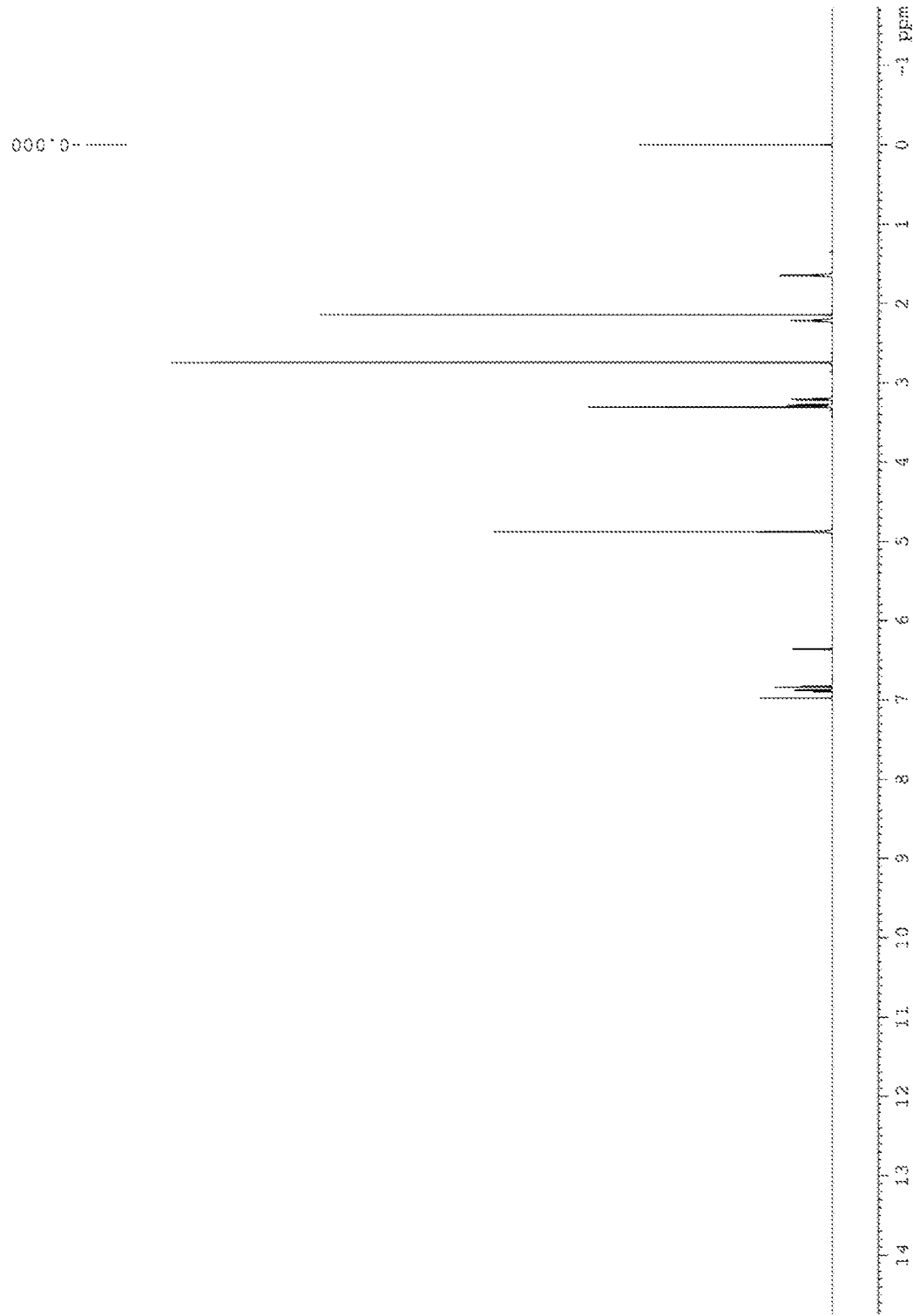
FIG. 20: $^1$H NMR spectrum of the hemiacetone solvate of the psilocin hemiadipate salt 4

FIG. 21: XRPD pattern of the psilocin fumarate salt 5
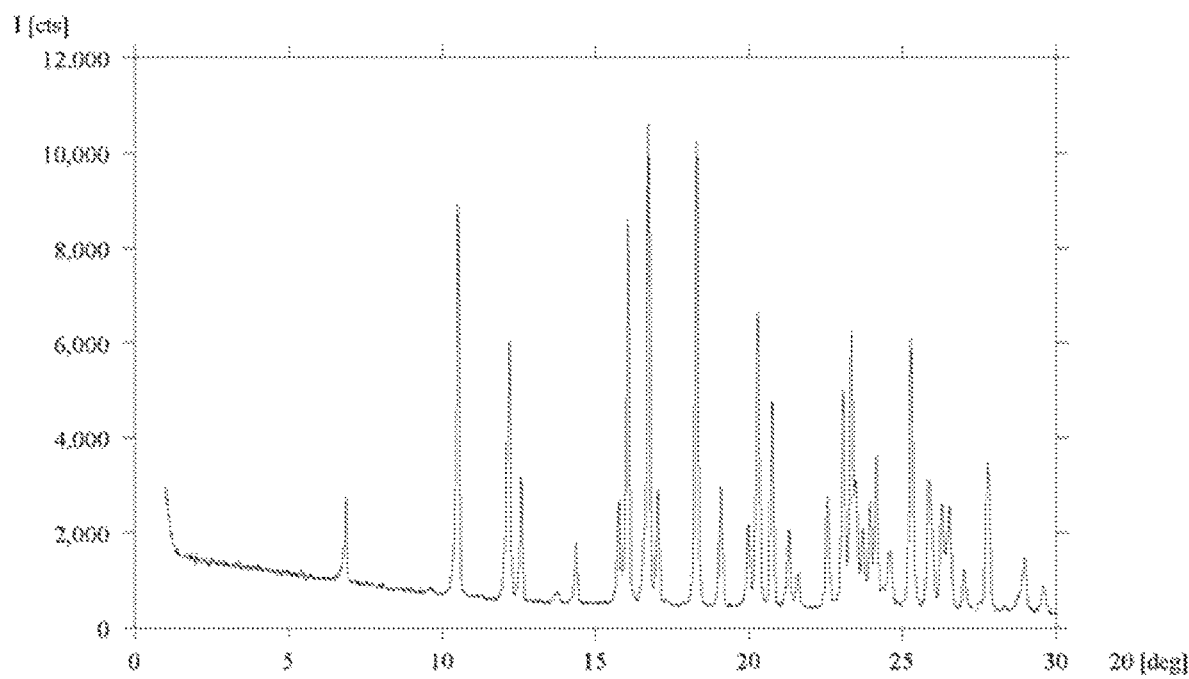

FIG. 22: XRPD pattern indexing of the psilocin fumarate salt 5
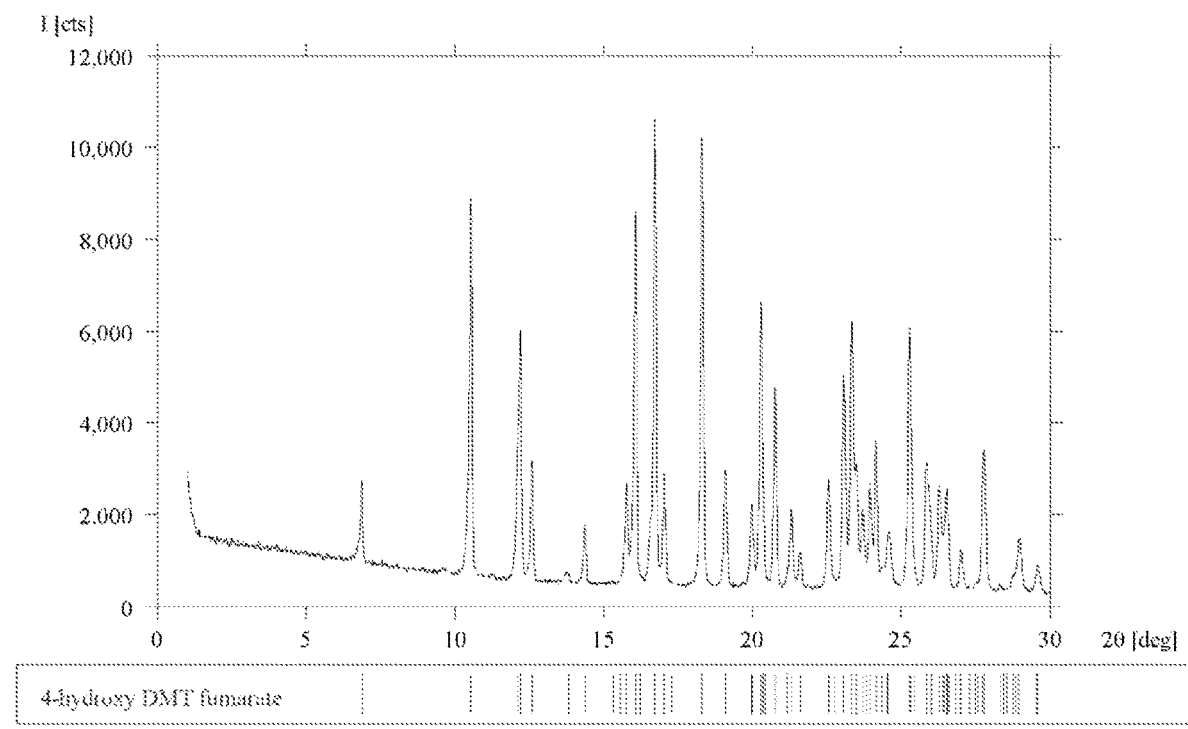

FIG. 23: DSC trace for the psilocin fumarate salt 5
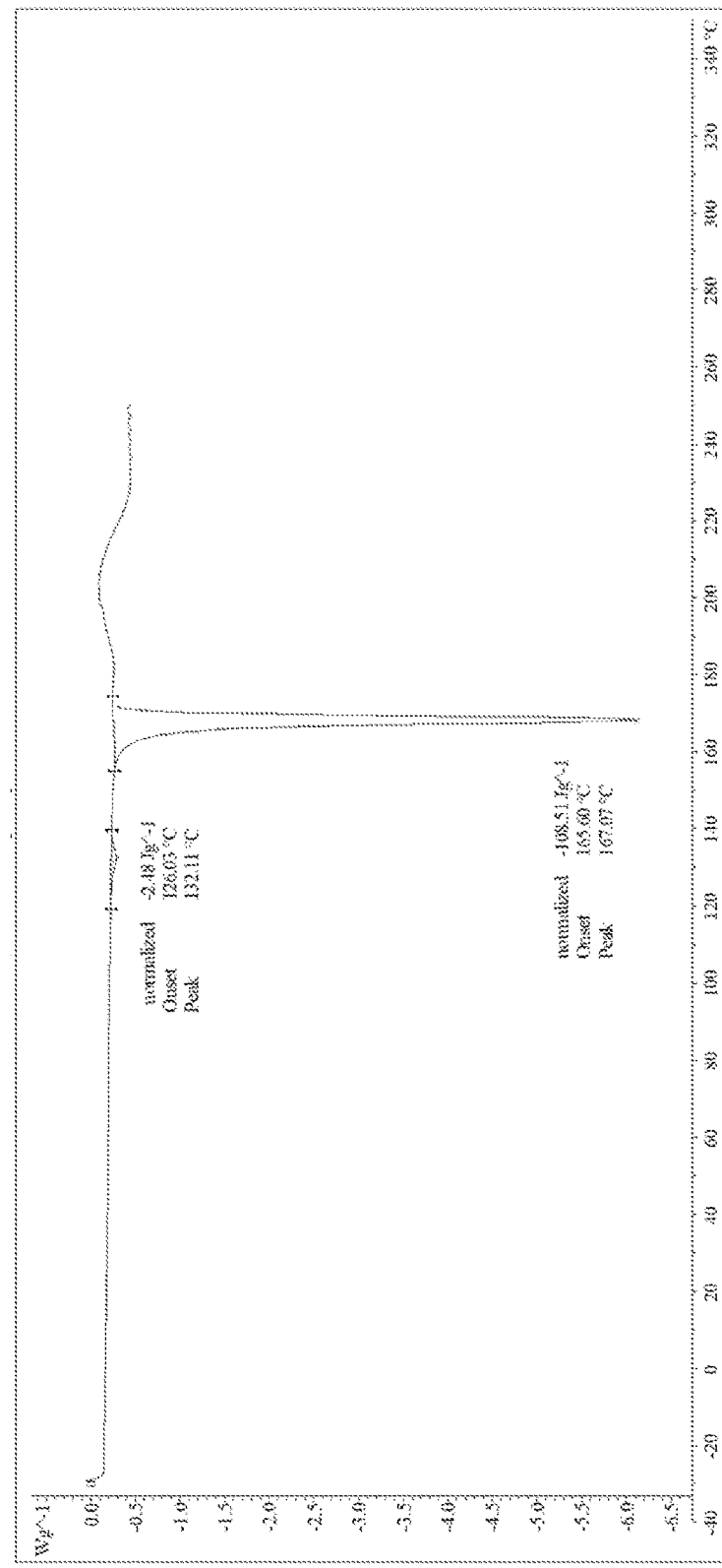

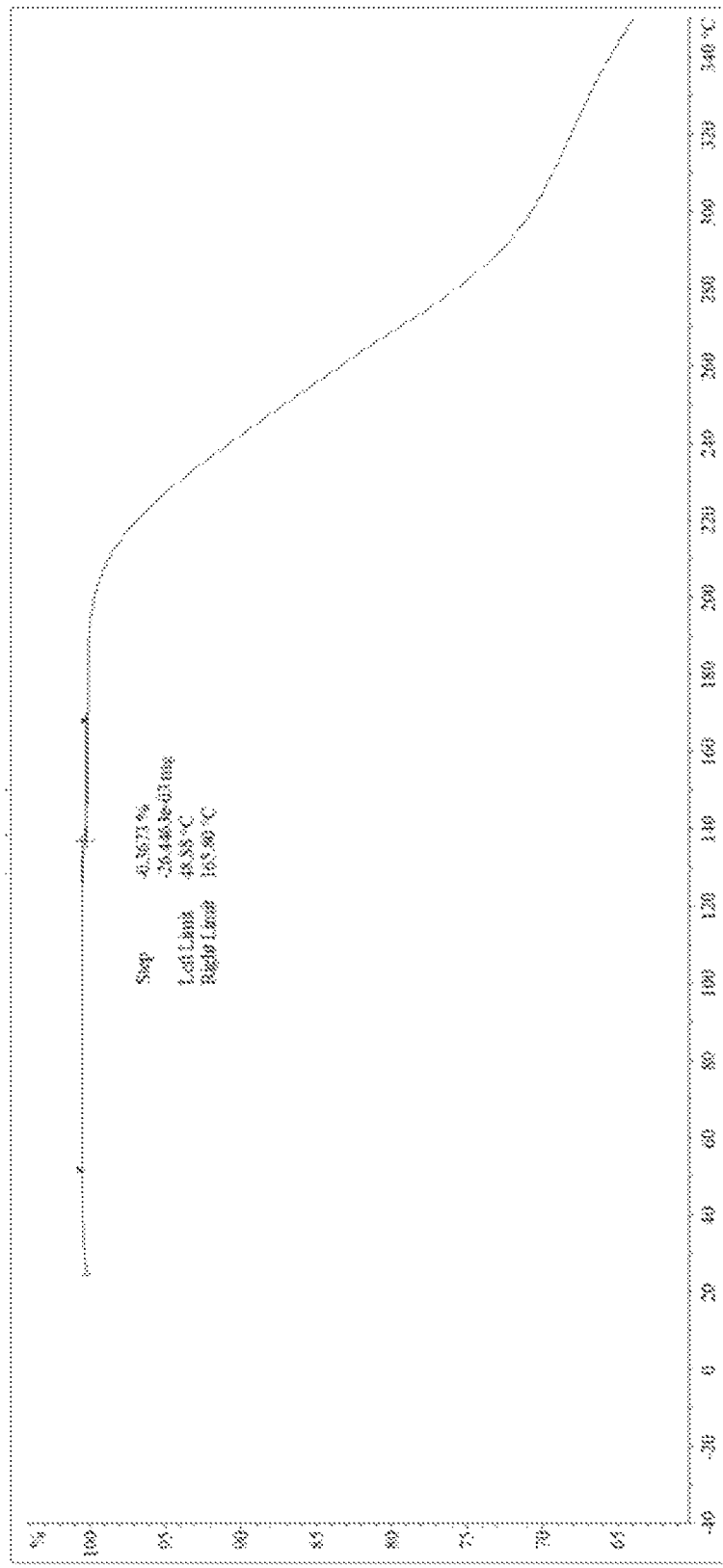
FIG. 24: TGA trace for the psilocin fumarate salt 5

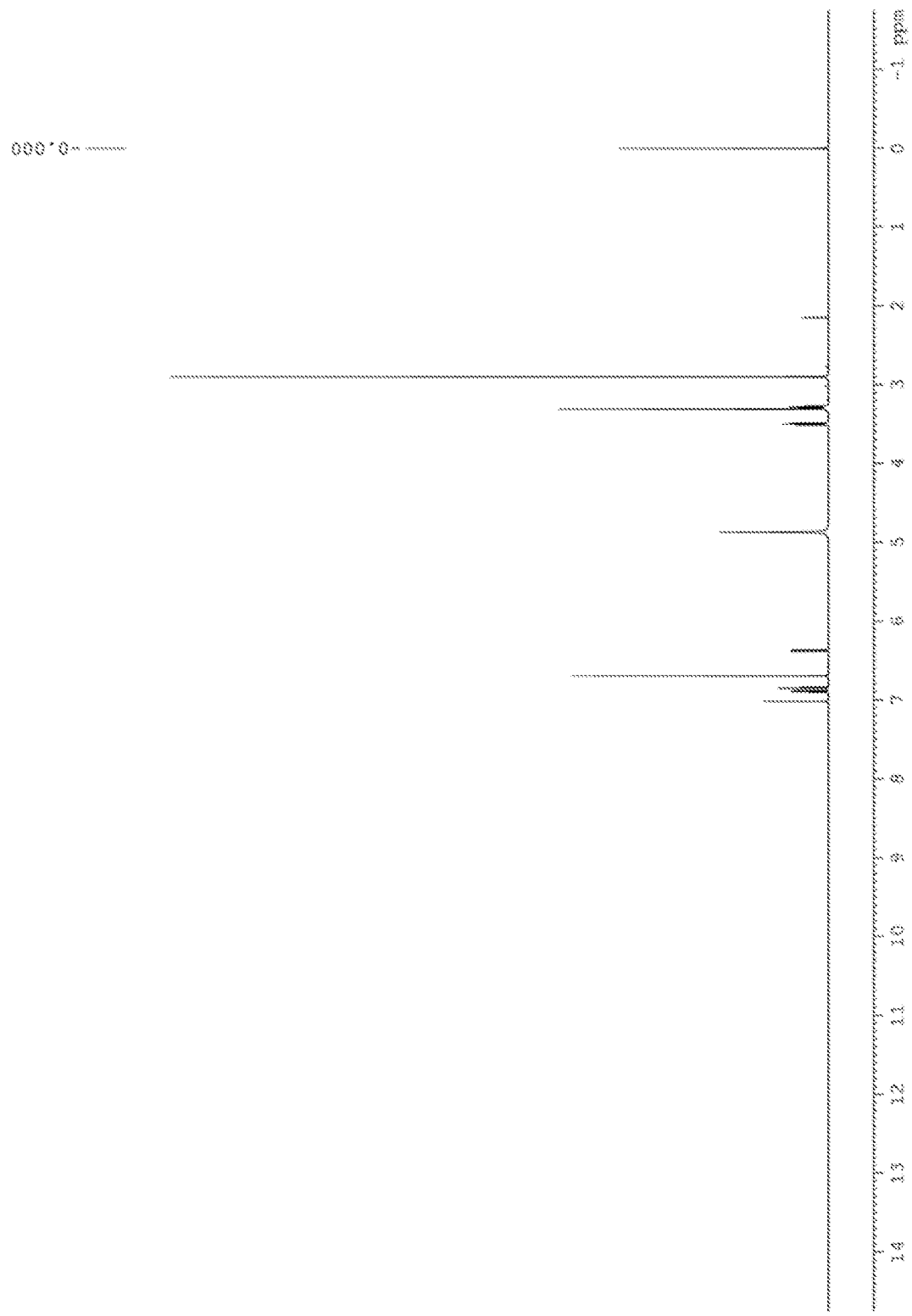
FIG. 25: ¹H NMR spectrum of the psilocin fumarate salt 5

FIG. 26: XRPD pattern of the psilocin hemifumarate salt 6
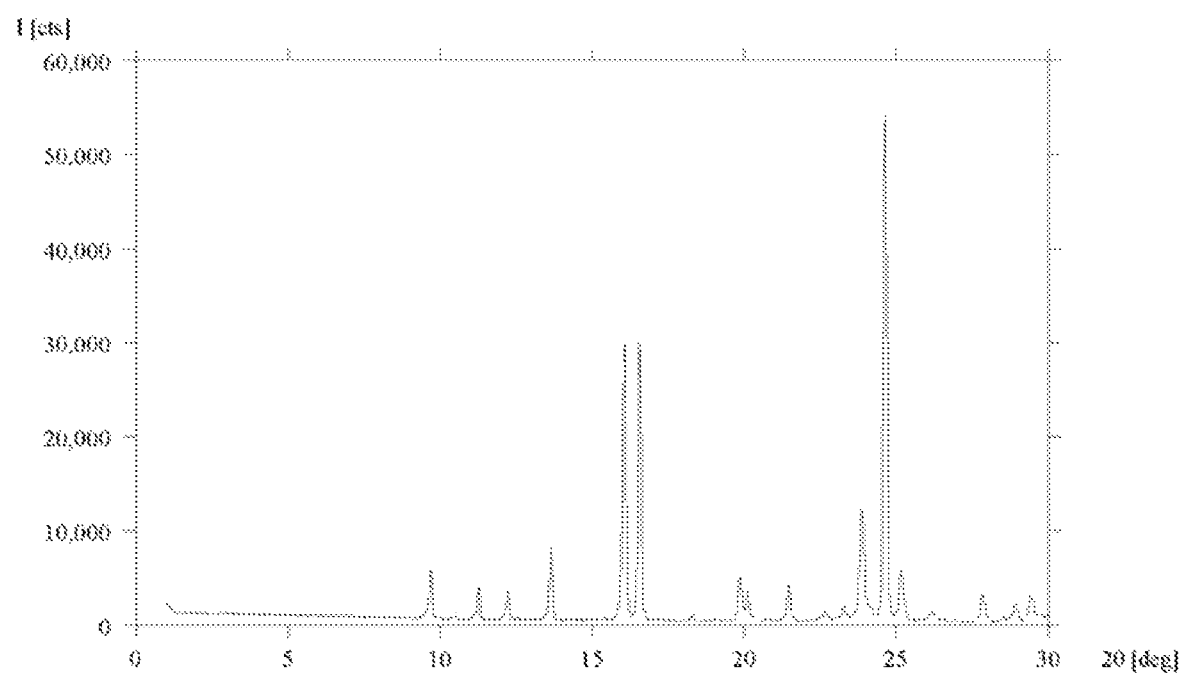

FIG. 27: XRPD pattern indexing of the psilocin hemifumarate salt 6
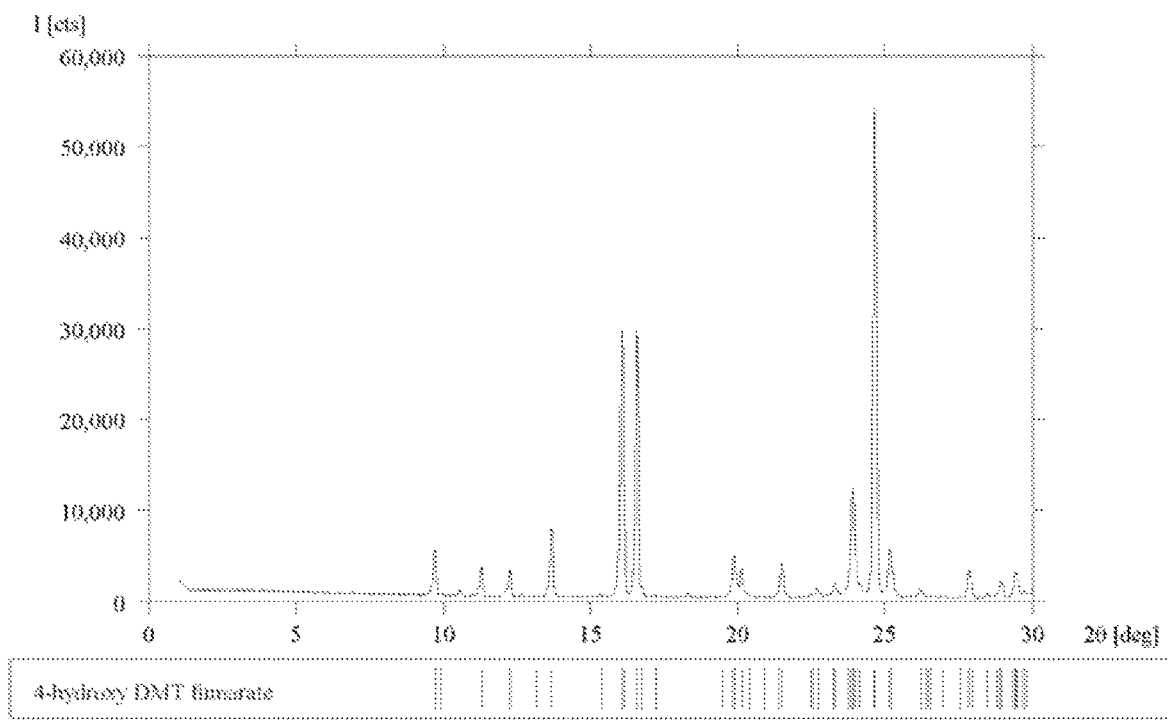

FIG. 28: DSC trace for the psilocin hemifumarate salt 6
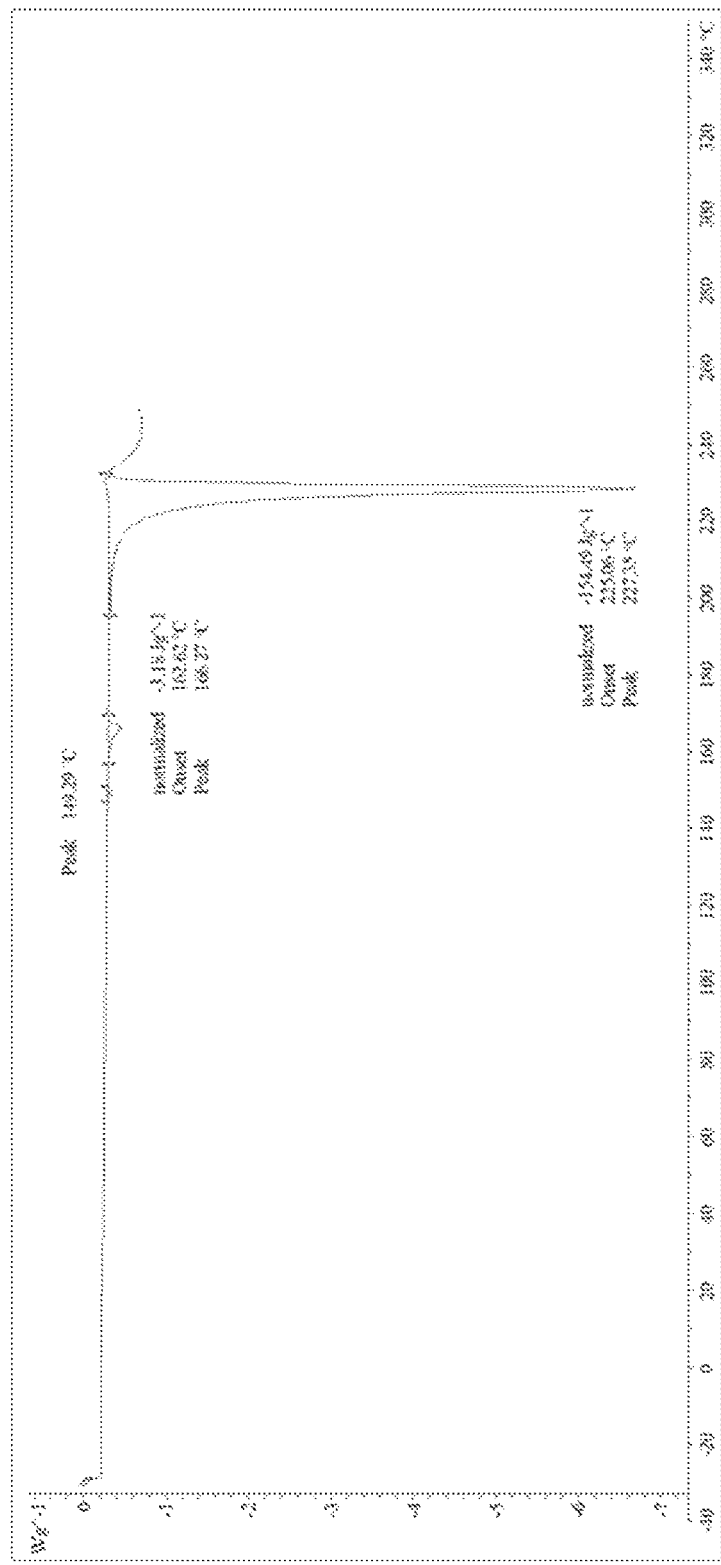

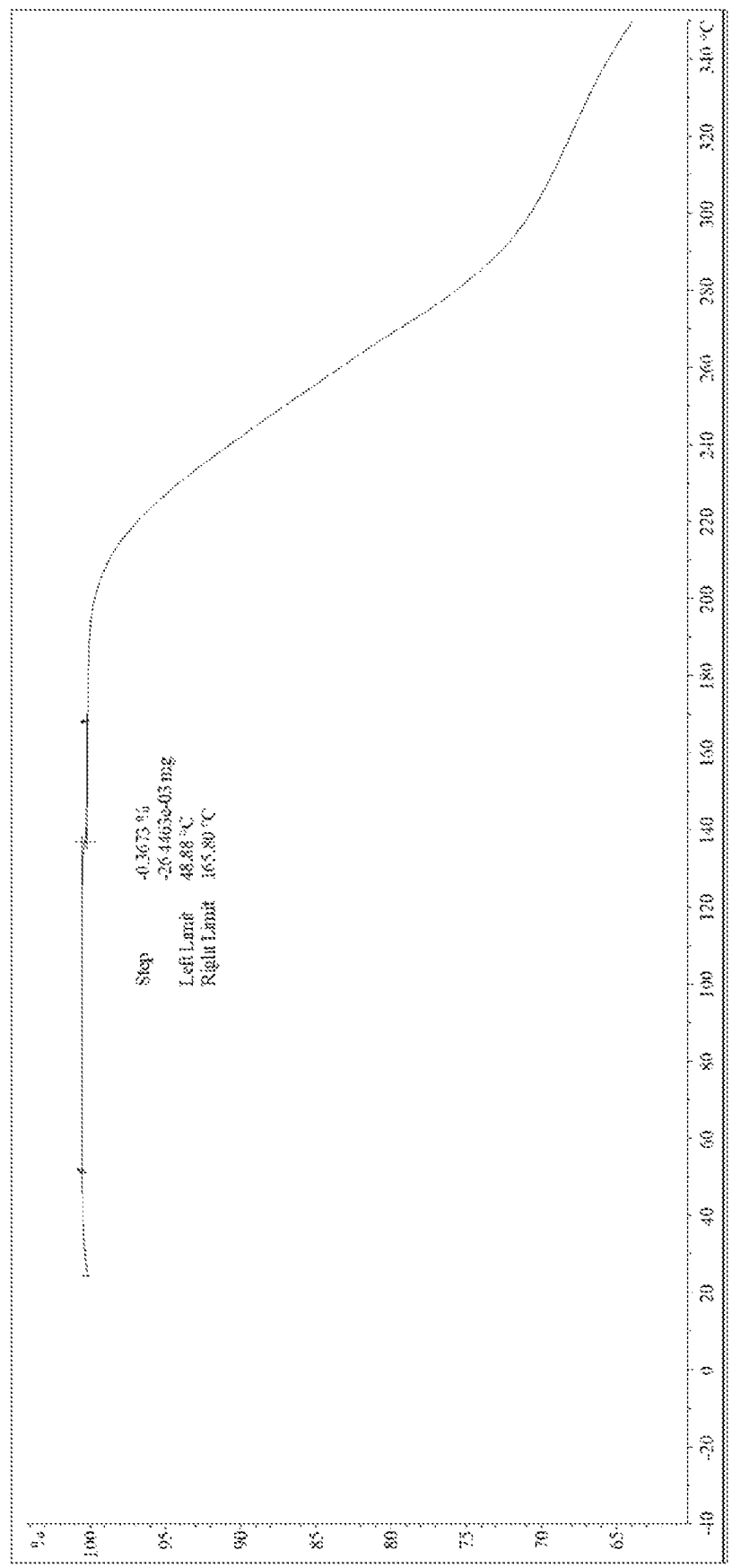
FIG. 29: TGA trace for the psilocin hemifumarate salt 6

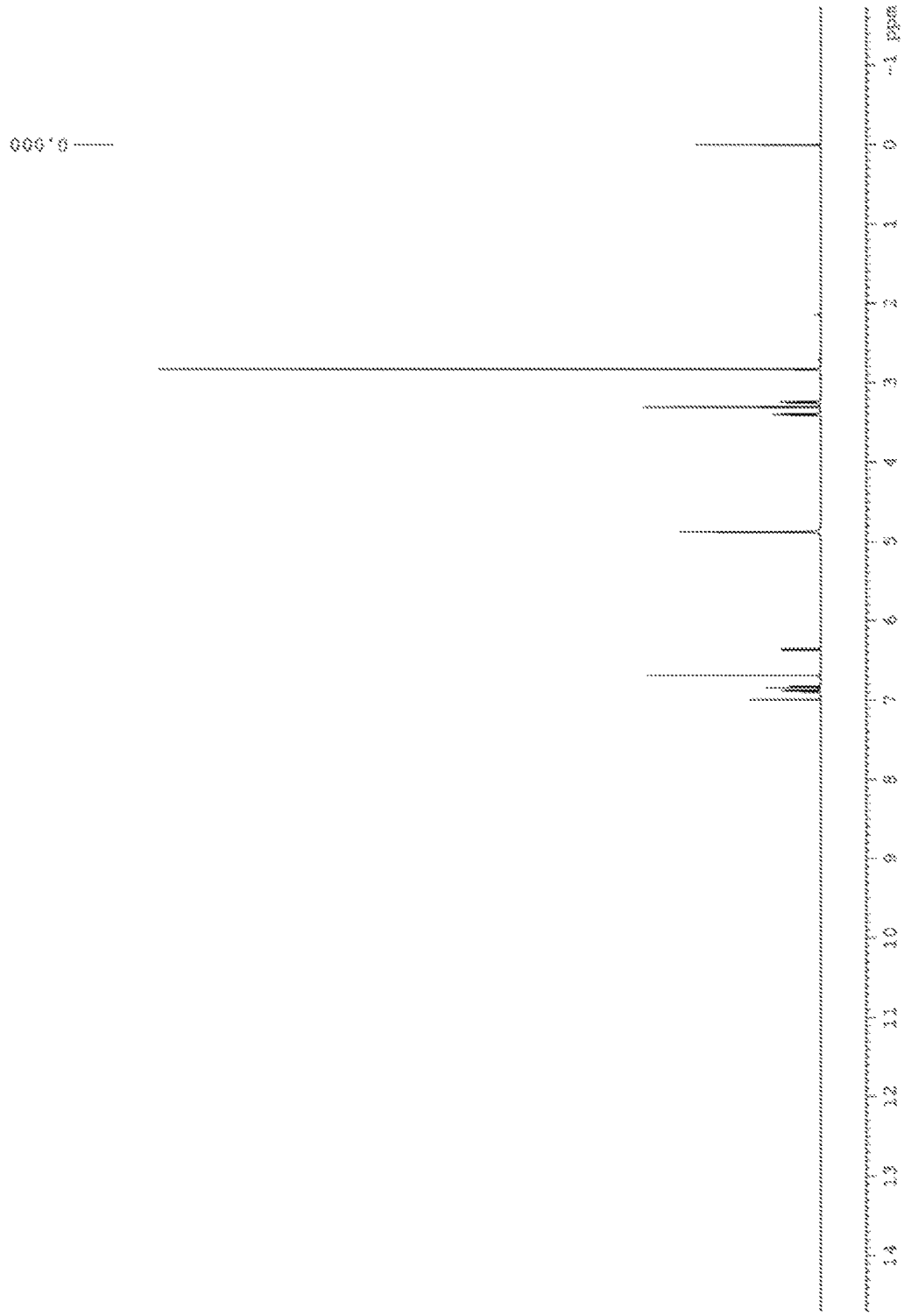
FIG. 30: 1H NMR spectrum of the psilocin hemifumarate salt 6

FIG. 31: XRPD pattern of the solvate of the psilocin oxalate salt 7
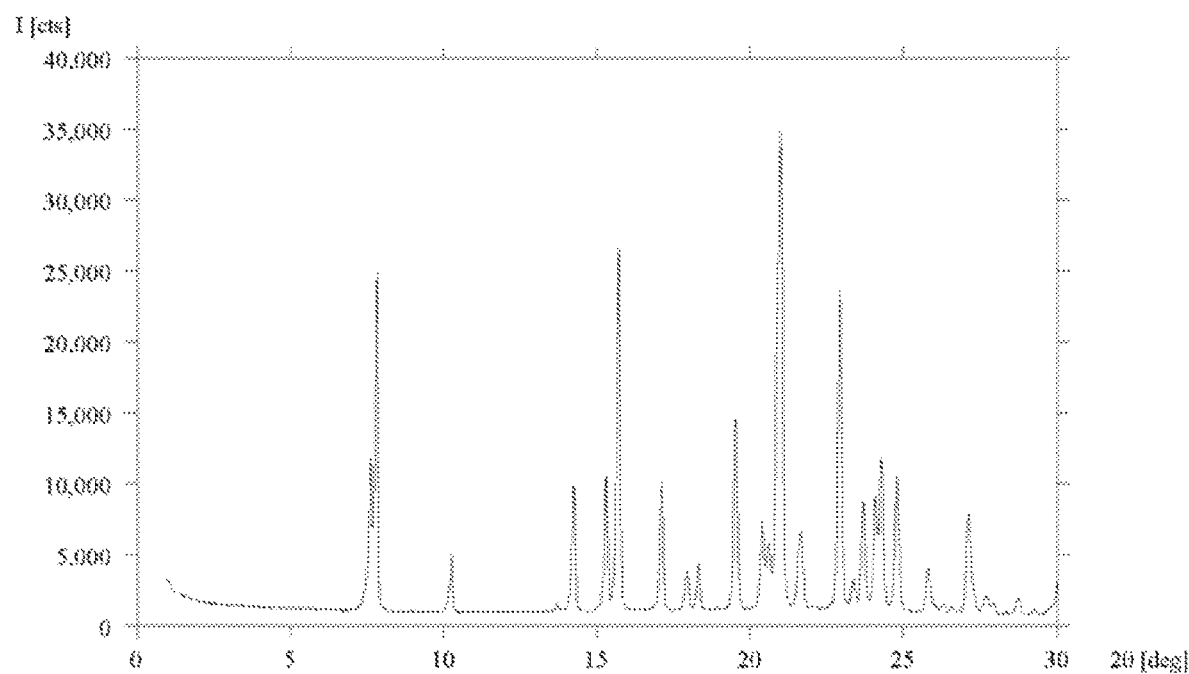

FIG. 32: XRPD pattern indexing of the solvate of the psilocin oxalate salt 7
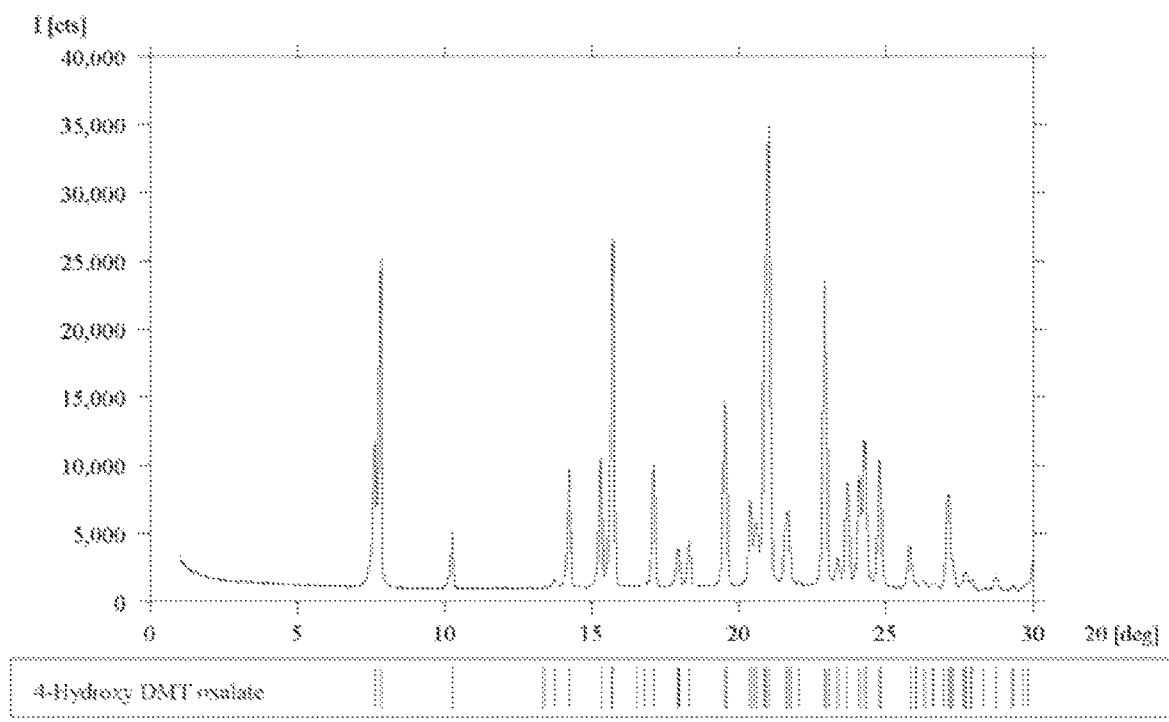

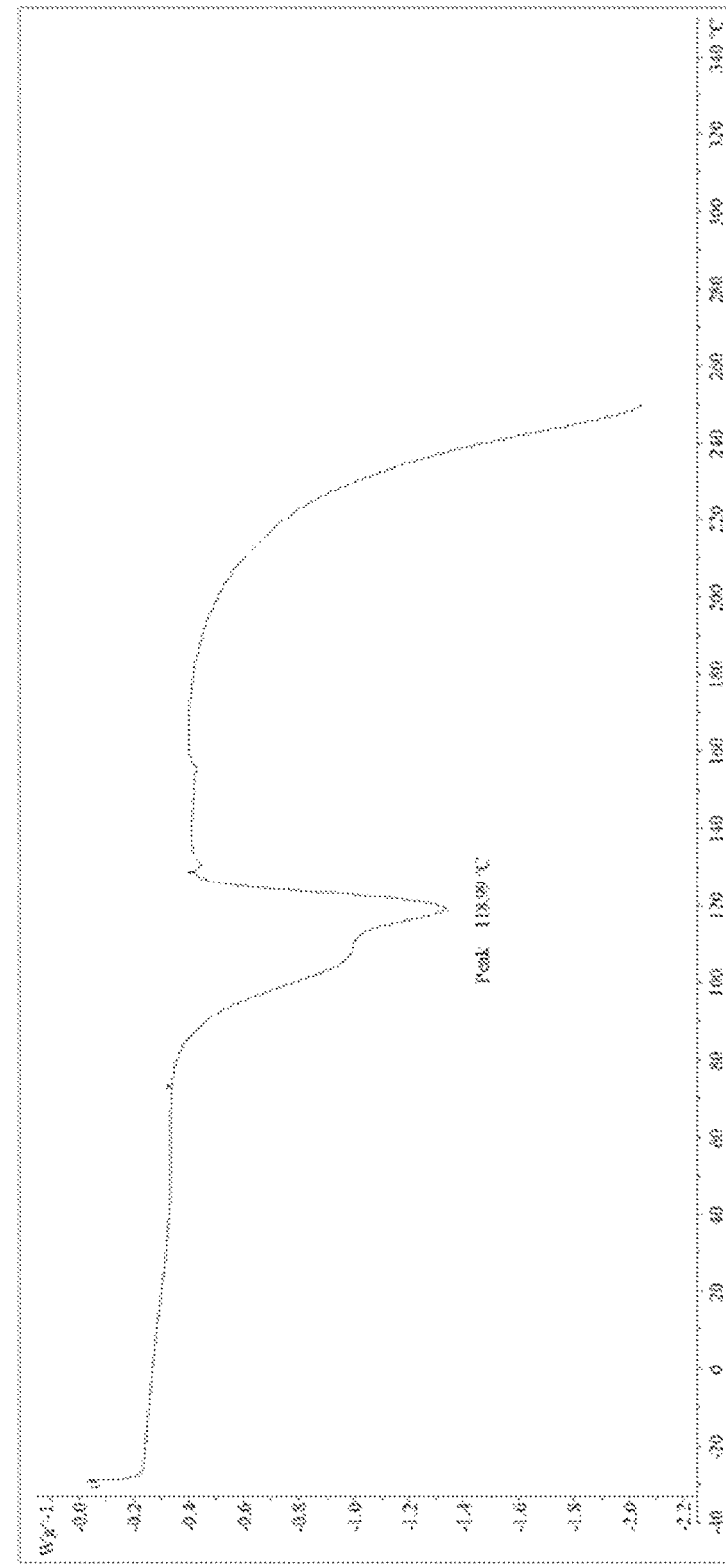
FIG. 33: DSC trace for the solvate of the psilocin oxalate salt 7

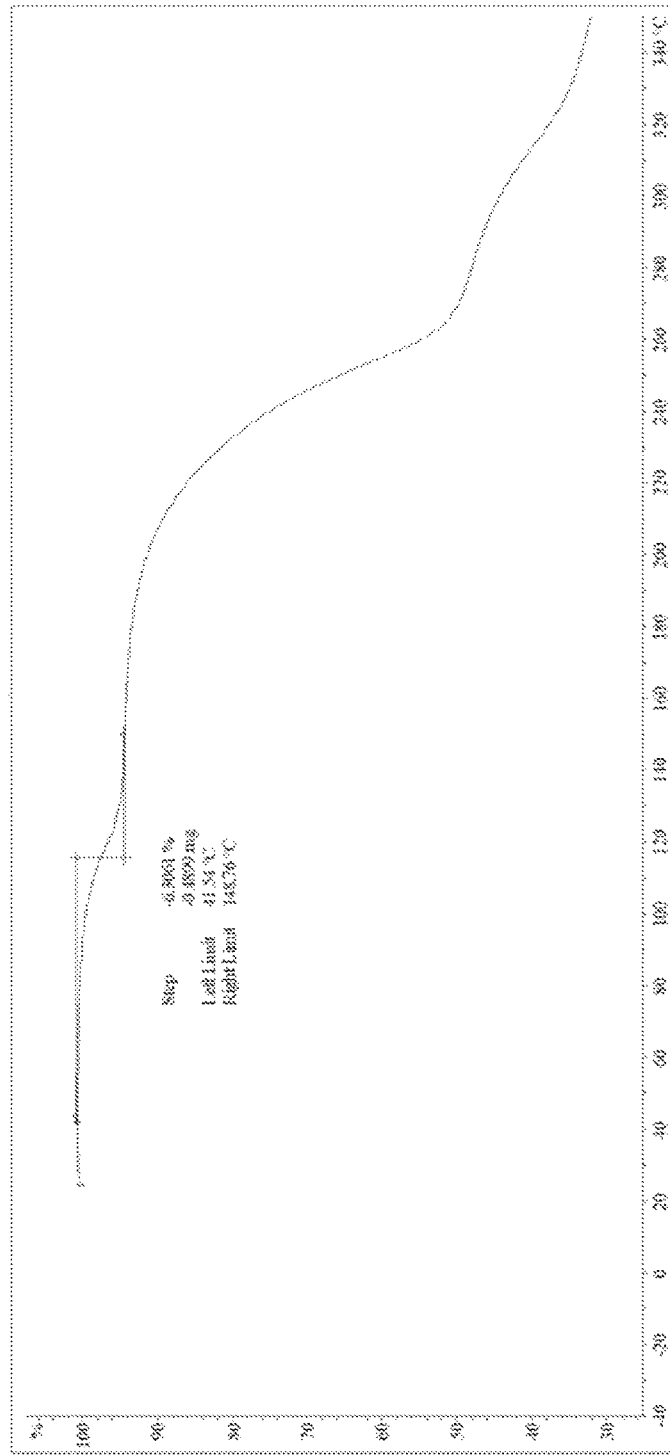
FIG. 34: TGA trace for the solvate of the psilocin oxalate salt 7

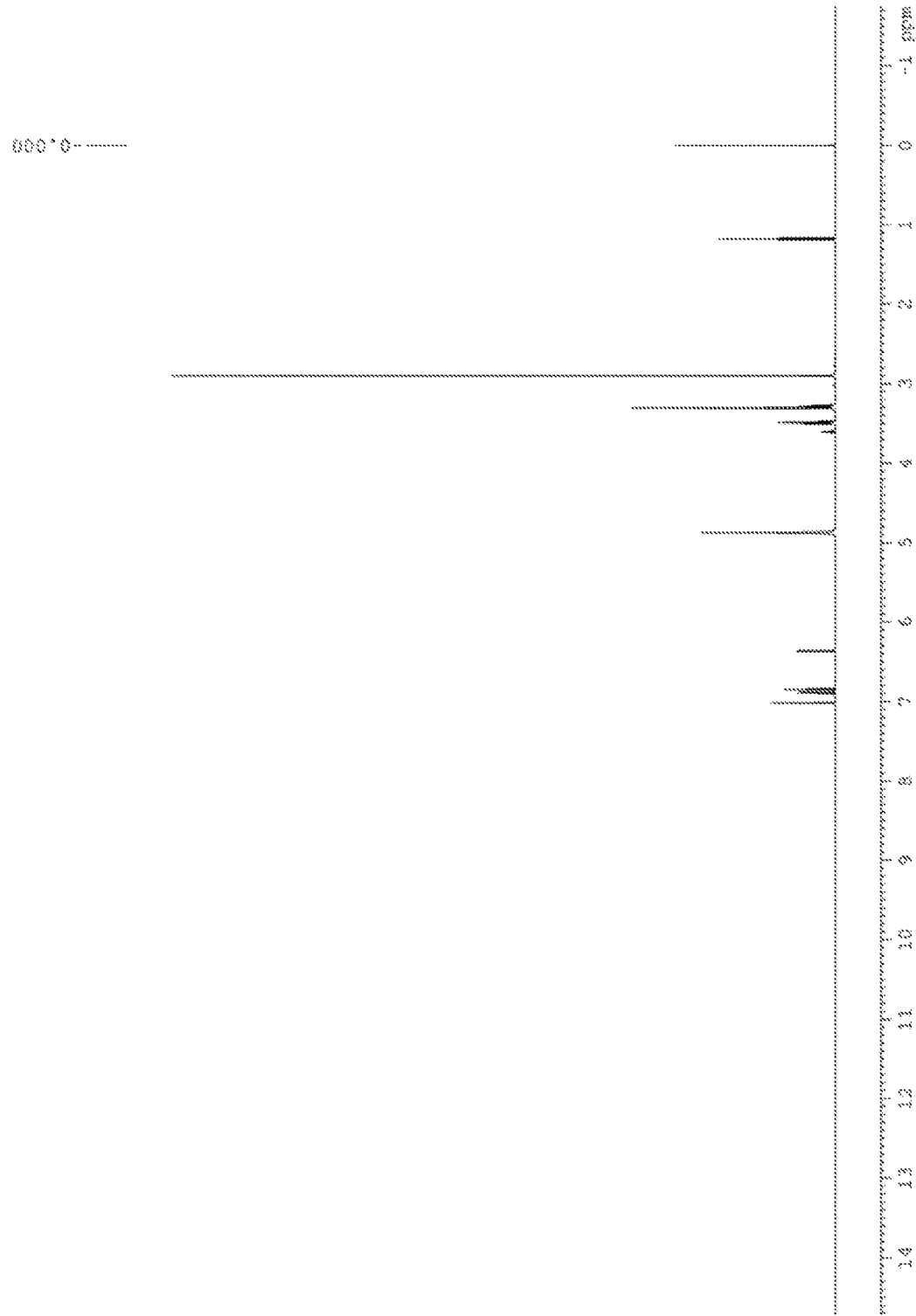
FIG. 35: ¹H NMR spectrum of the solvate of the psilocin oxalate salt 7

FIG. 36: XRPD pattern of the psilocin DL-lactate salt 8
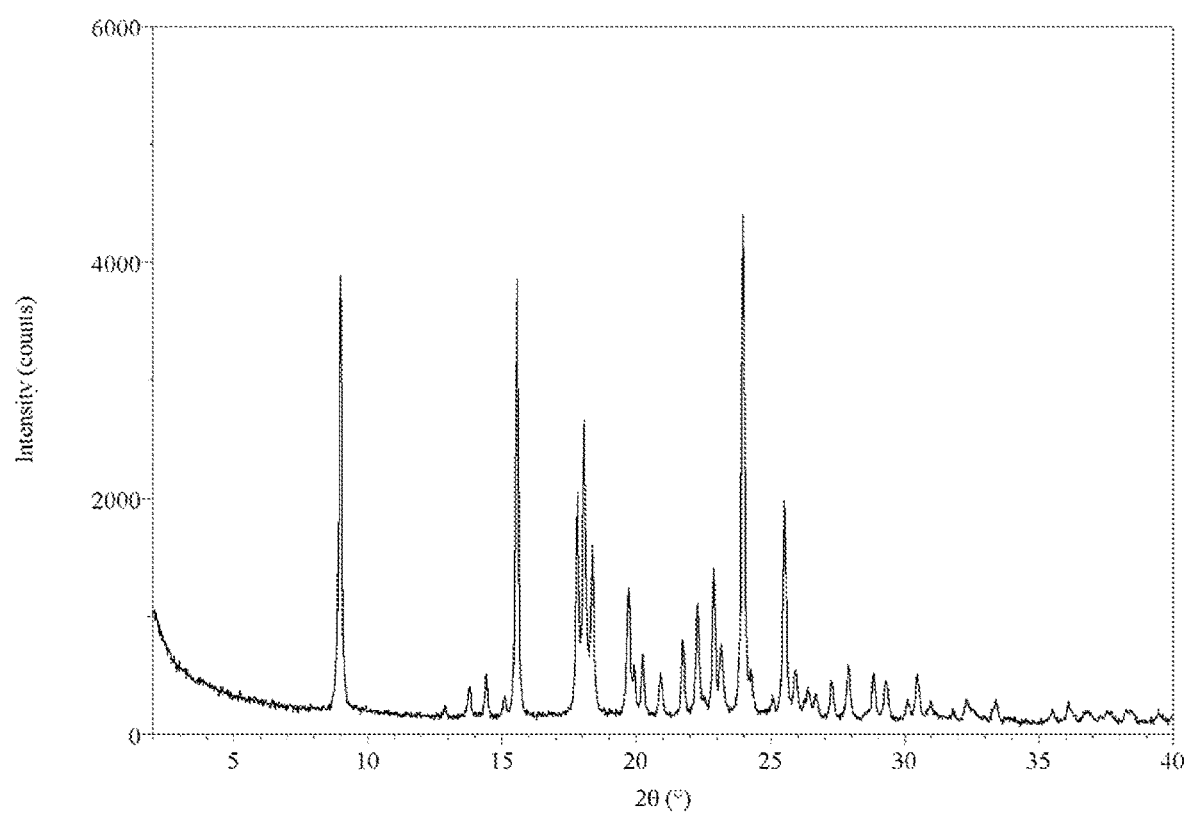

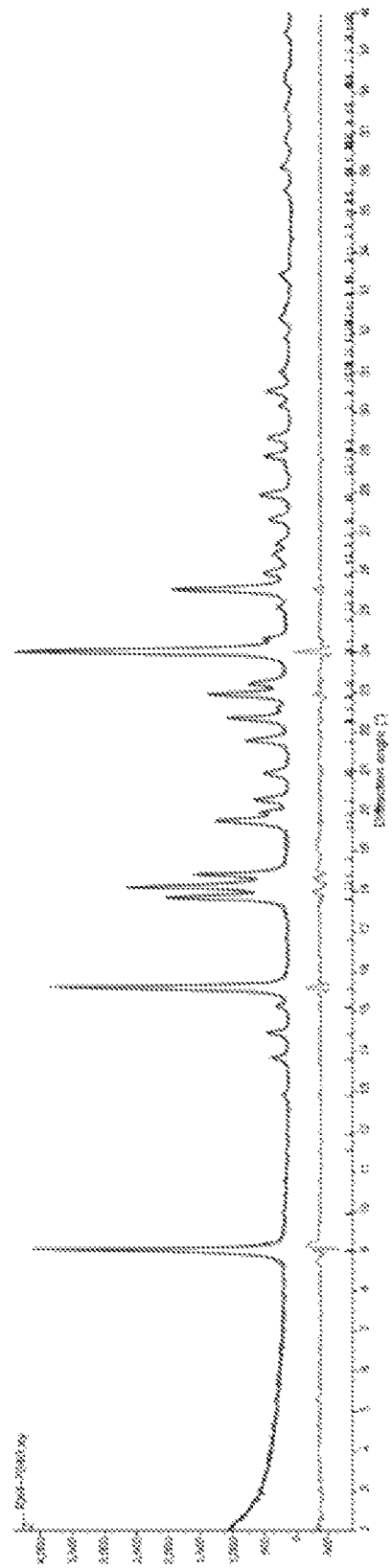
FIG. 37: XRPD pattern indexing of the psilocin DL-lactate salt 8

FIG. 38: DSC trace for the psilocin DL-lactate salt 8
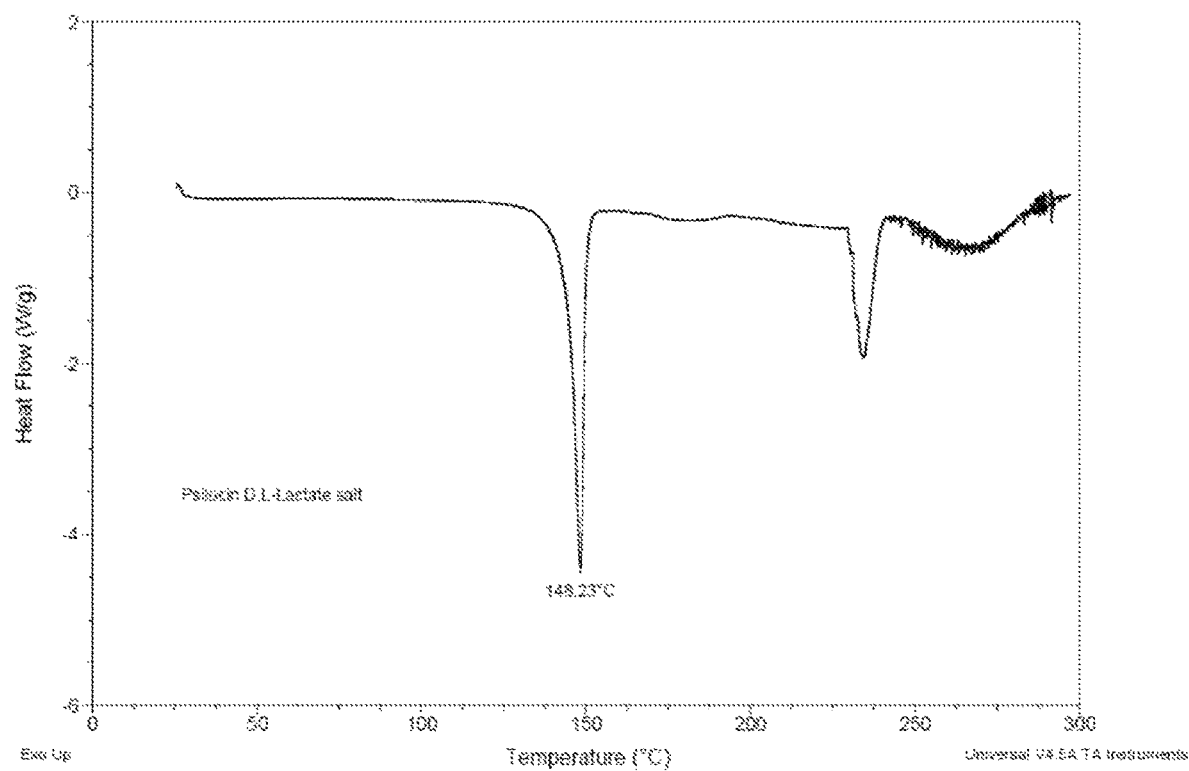

FIG. 39: TGA trace for the psilocin DL-lactate salt 8
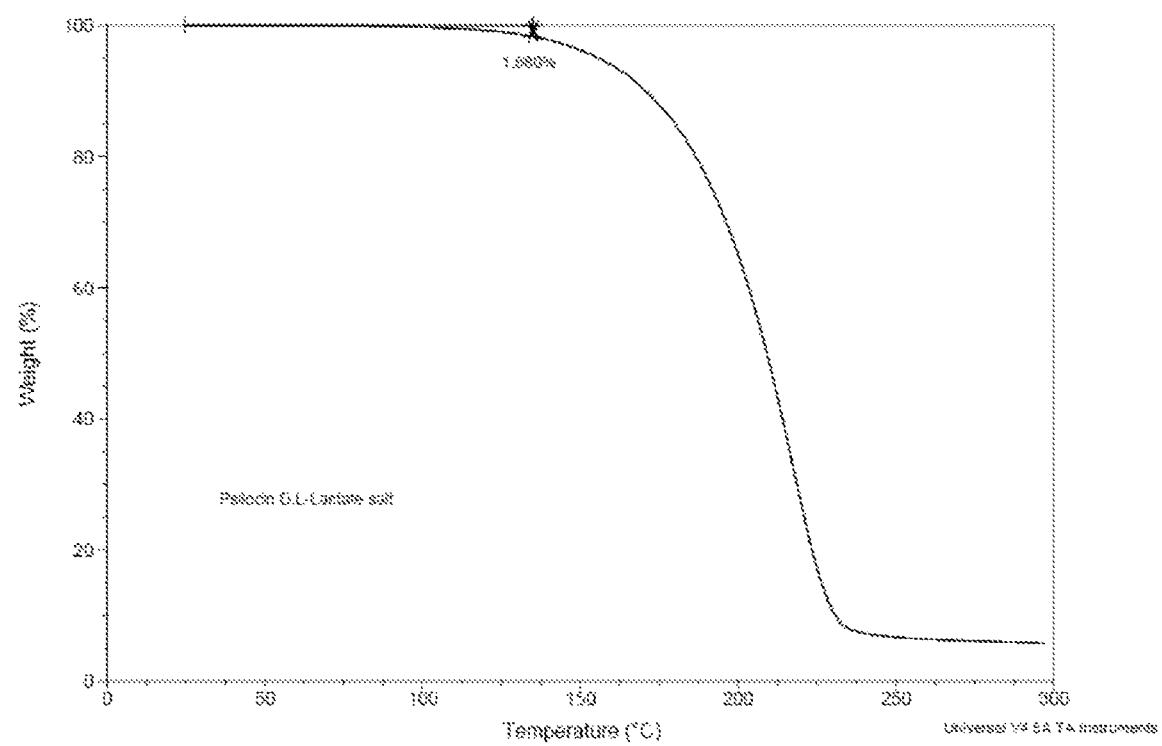

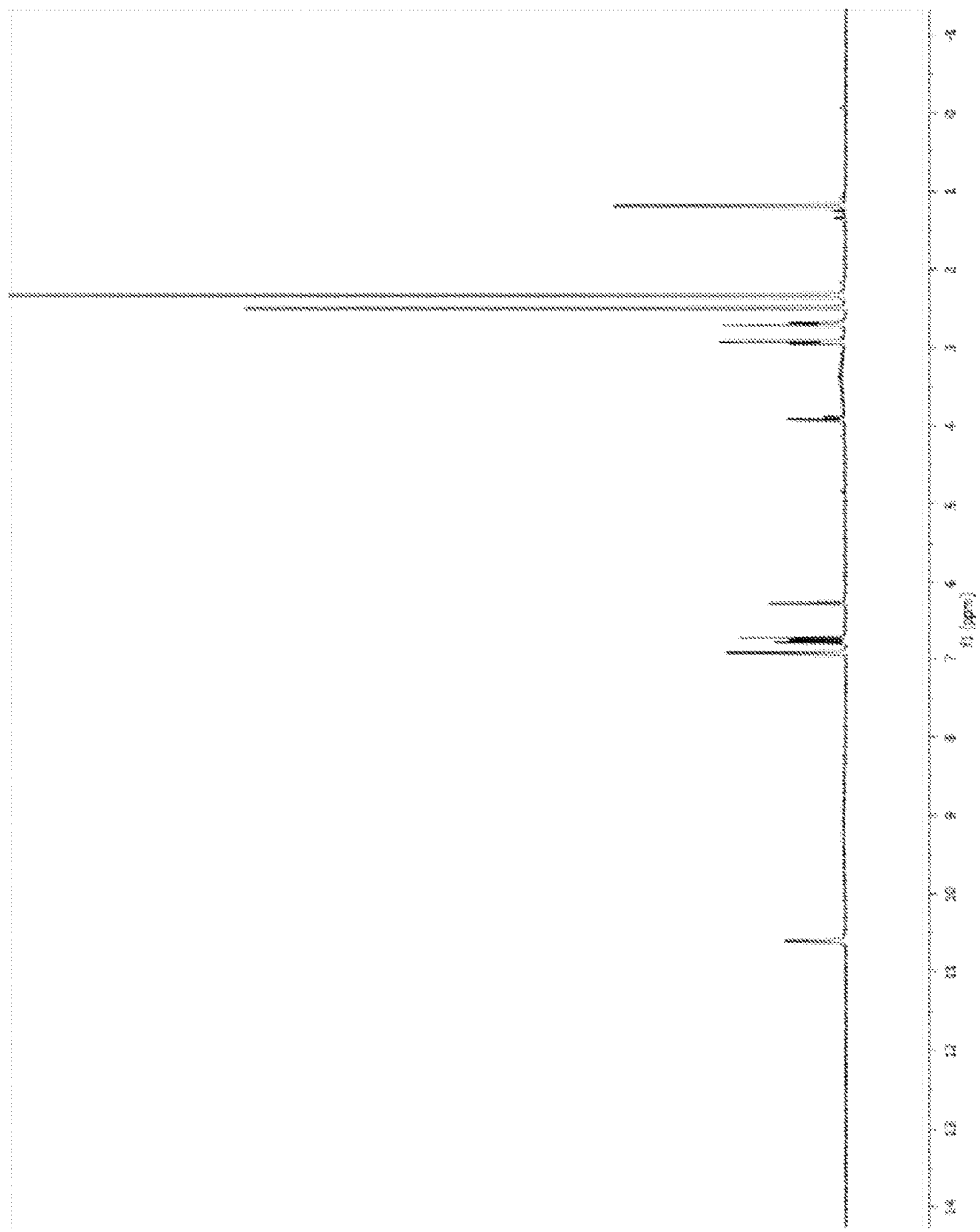
FIG. 40: ¹H NMR spectrum of the psilocin DL-lactate salt 8

FIG. 41: XRPD pattern of the psilocin L-malate salt 9
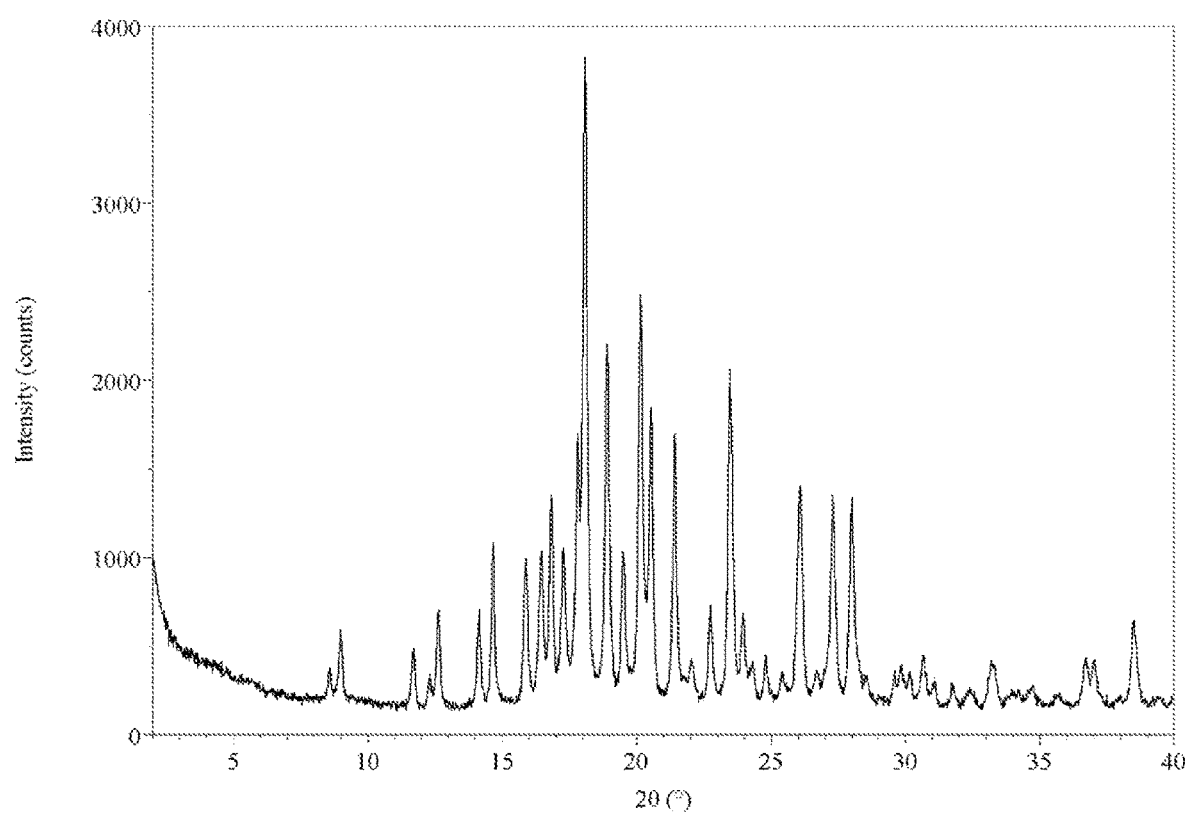

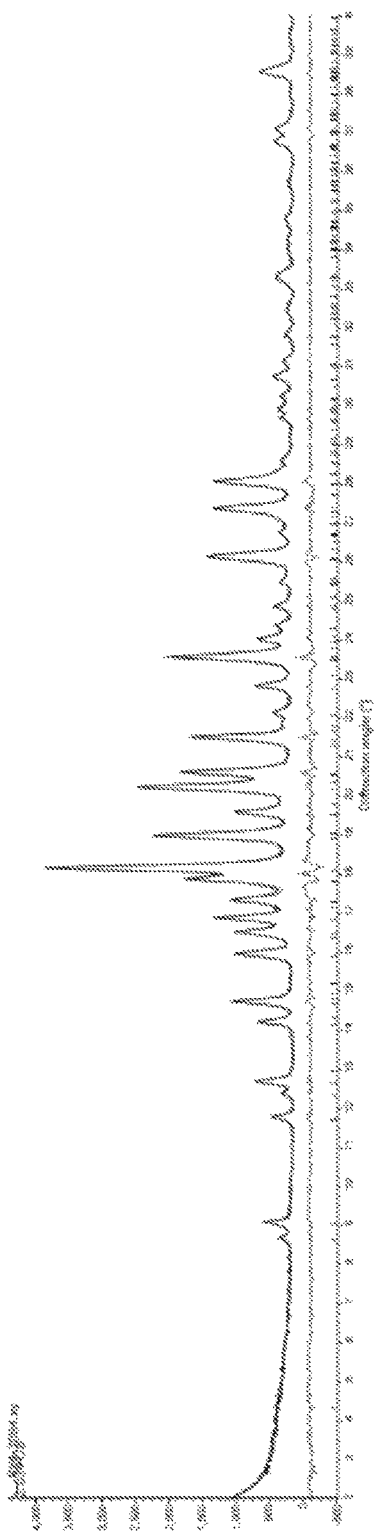
FIG. 42: XRPD pattern indexing of the psilocin L-malate salt 9

FIG. 43: DSC trace for the psilocin L-malate salt 9
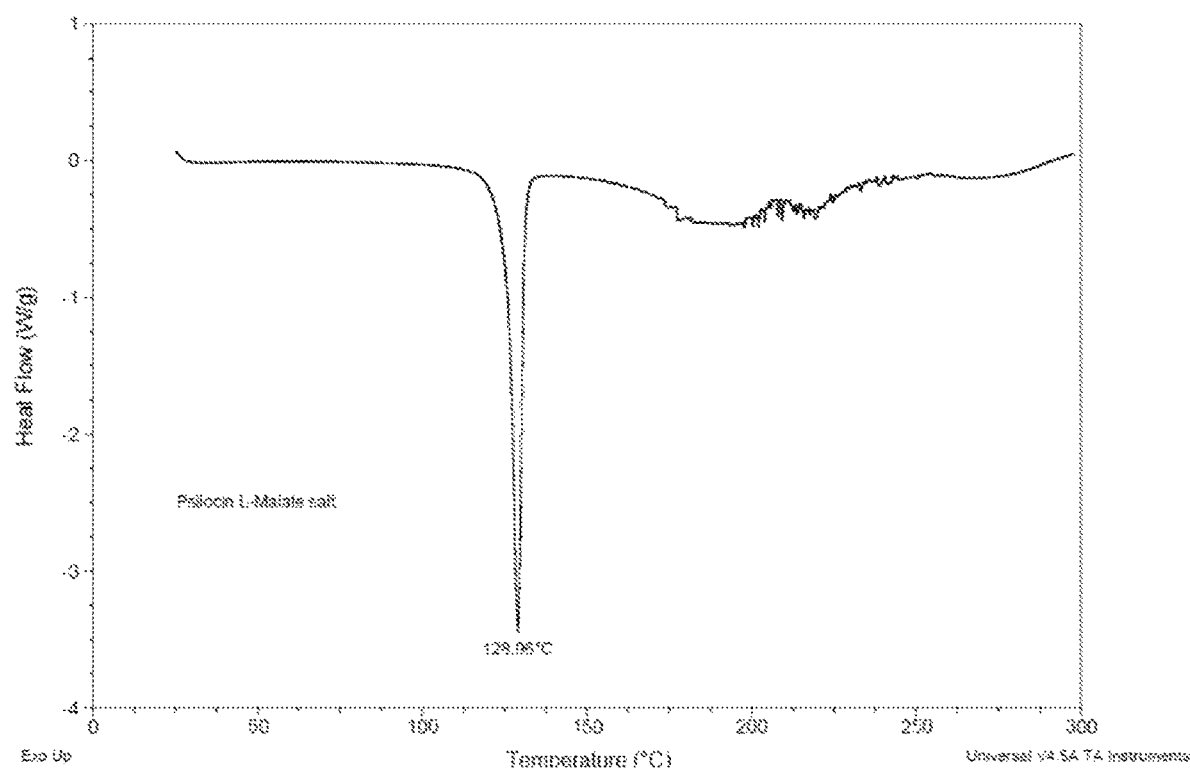

FIG. 44: TGA trace for the psilocin L-malate salt 9
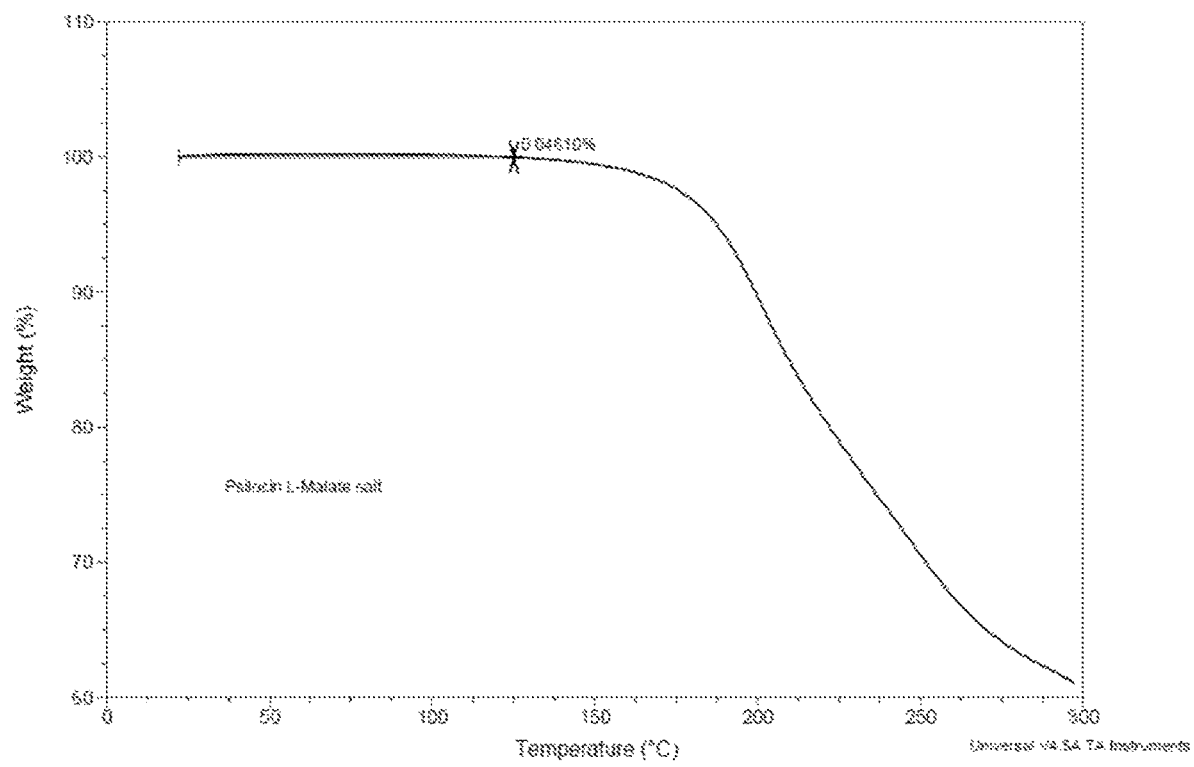

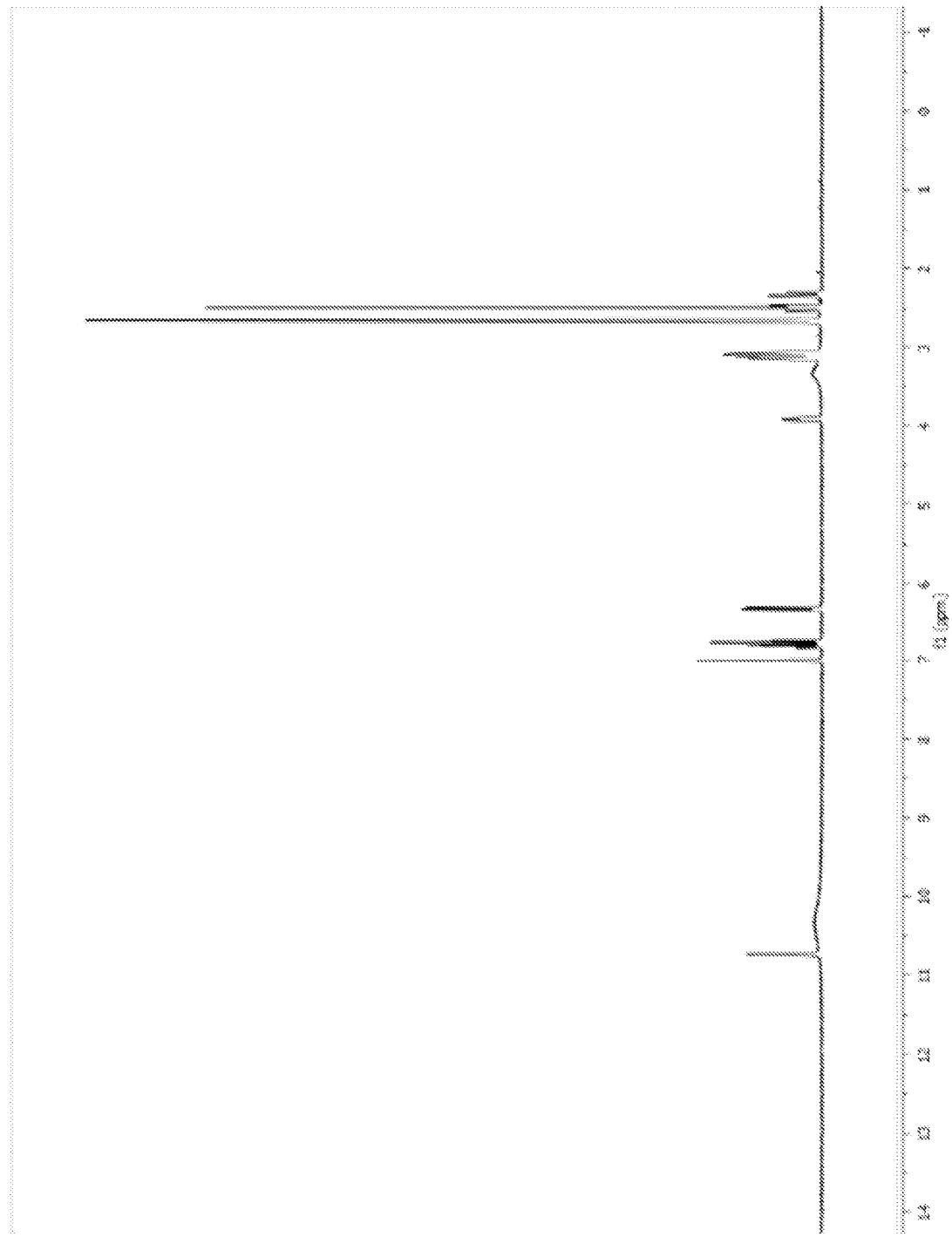
FIG. 45: ¹H NMR spectrum of the psilocin L-malate salt 9

FIG. 46: XRPD pattern of the psilocin stearate salt 10
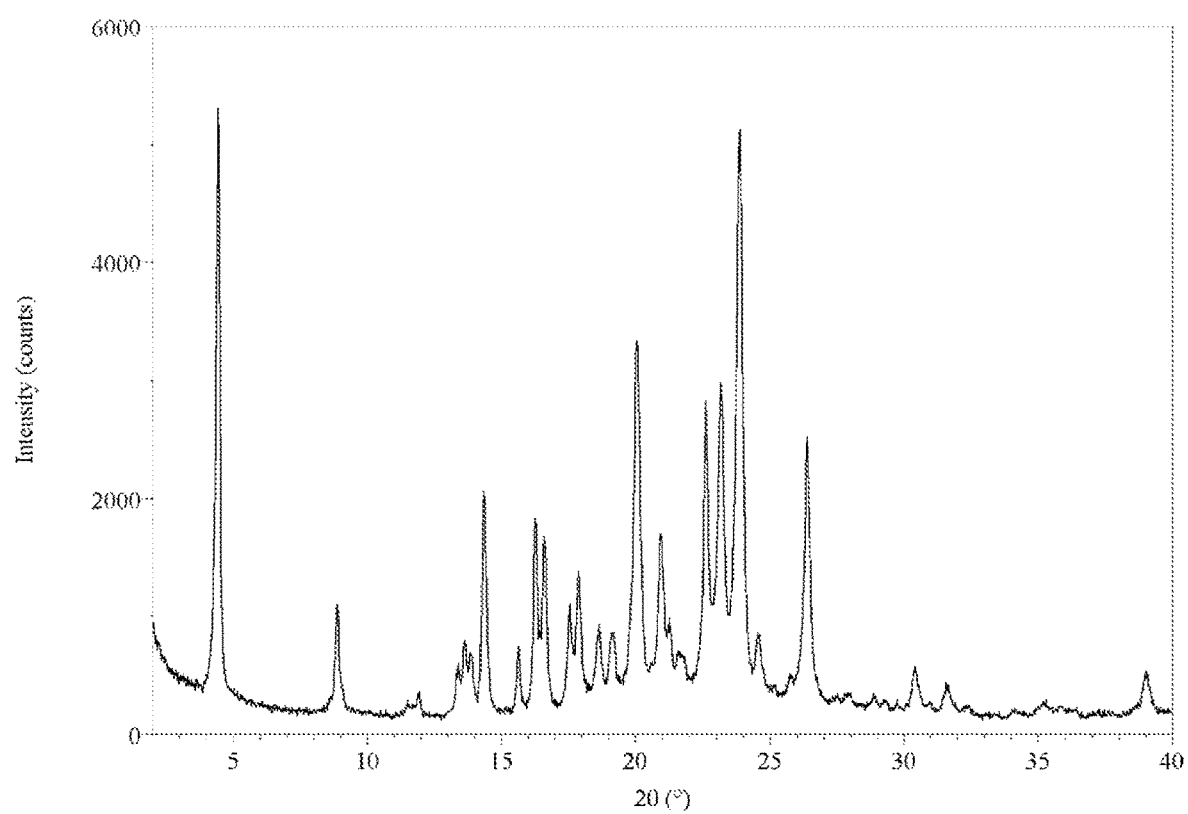

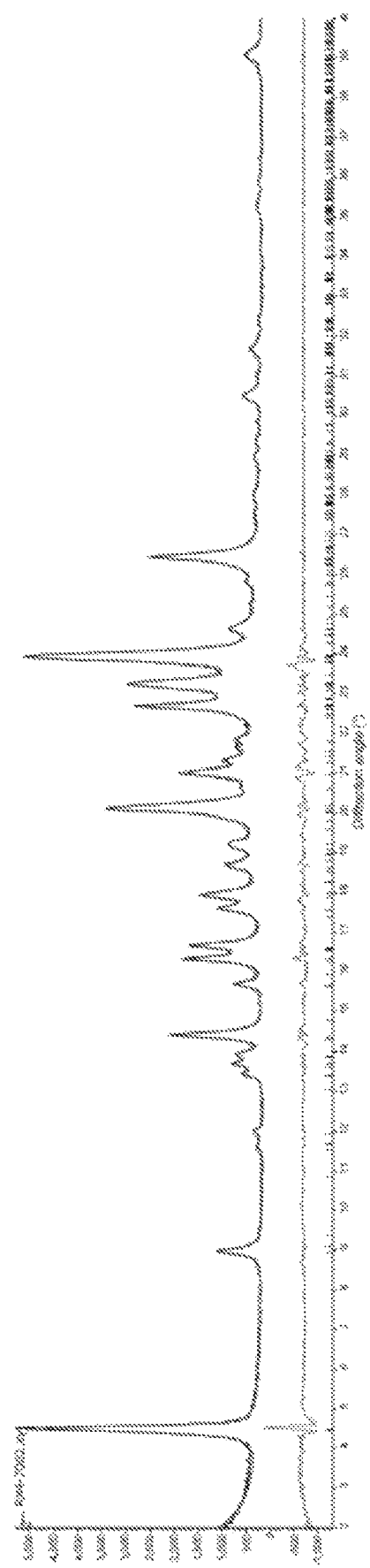
FIG. 47: XRPD pattern indexing of the psilocin stearate salt 10

FIG. 48: DSC trace for the psilocin stearate salt 10
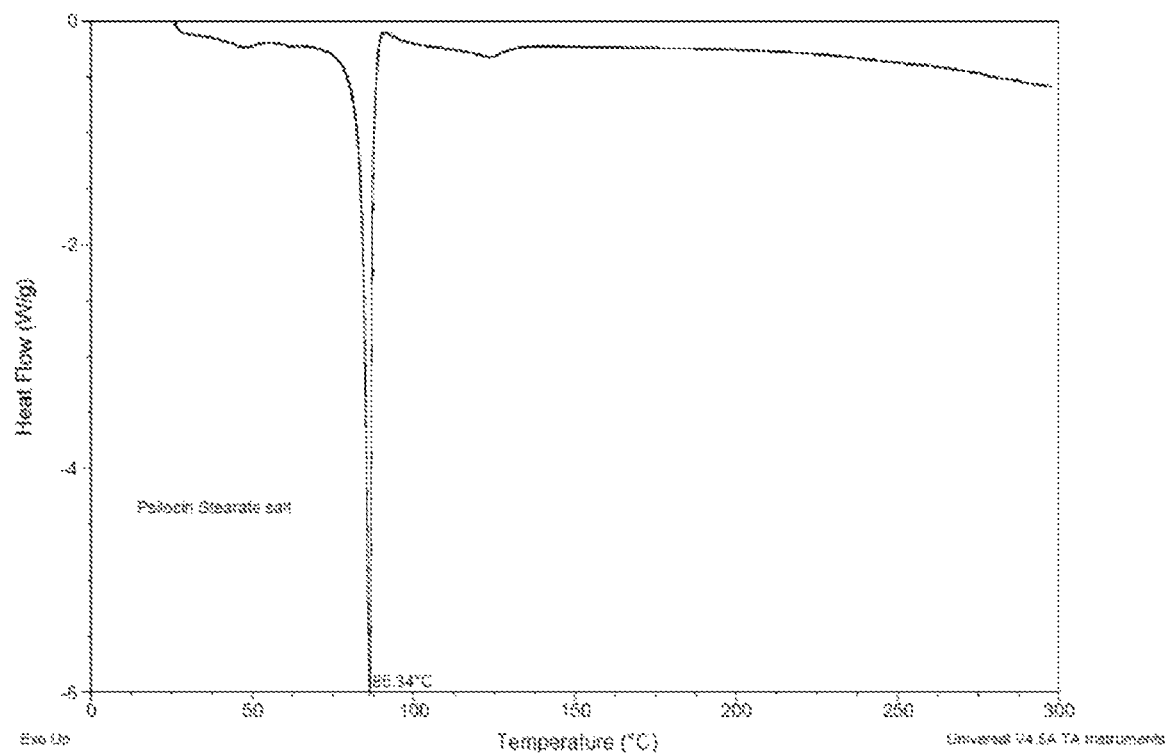

FIG. 49: TGA trace for the psilocin stearate salt 10
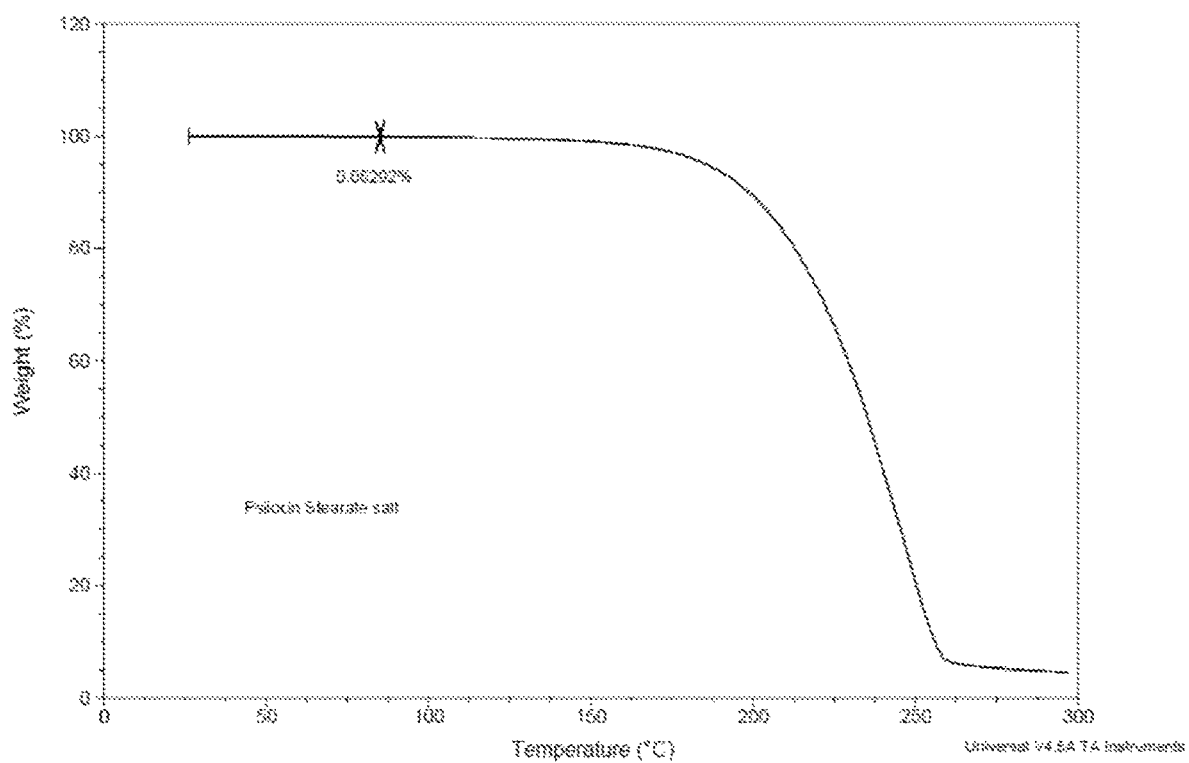

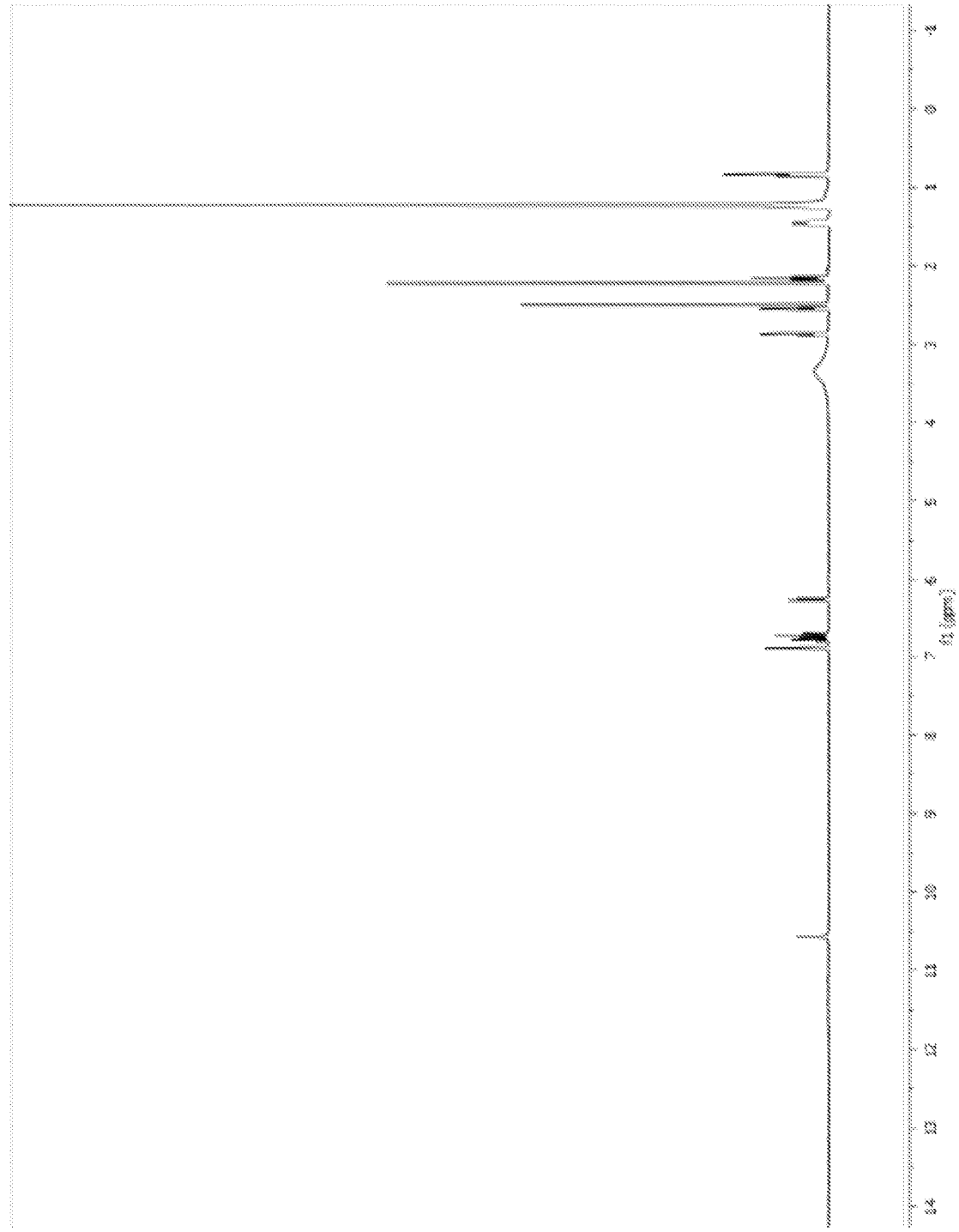
FIG. 50: $^1$H NMR spectrum of the psilocin stearate salt 10

CRYSTALLINE SALTS OF PSILOCIN

PRIORITY CLAIM

This application claims the benefit of priority to U.S. Provisional Patent Application No. 63/192,266, filed May 24, 2021, U.S. Provisional Patent Application No. 63/240,092, filed Sep. 2, 2021, U.S. Provisional Patent Application No. 63/244,610, filed Sep. 15, 2021, and U.S. Provisional Patent Application No. 63/310,703, filed Feb. 16, 2022, all of which are herein incorporated by reference in their entirety.

FIELD OF THE INVENTION

The invention relates to crystalline salts of psilocin and the processes for preparation thereof. The invention also relates to beneficial and therapeutic uses of the crystalline salts and of compositions containing the crystalline salt forms.

BACKGROUND OF THE INVENTION

Crystalline forms of therapeutic drugs have been used to alter the physicochemical properties of the drug. Each crystalline form of a drug can have different solid-state (physical and chemical) properties which may be relevant for drug delivery. Crystalline forms often have better chemical and physical properties than corresponding non-crystalline forms such as the amorphous form. The differences in physical properties exhibited by a novel solid form of a drug (such as a salt, polymorph or cocrystal) affect pharmaceutical parameters such as melting point, storage stability, compressibility, and density (relevant for formulation and product manufacturing), and dissolution rates and solubility (relevant factors in achieving suitable bioavailability).

Obtaining a suitable crystalline form of a drug is often a necessary stage for many orally available drugs. Suitable crystalline forms possess the desired properties of a particular drug. Such suitable crystalline forms may be obtained by forming a salt between the ionizable drug and a suitable acid/base. Salts often possess more favorable pharmaceutical and pharmacological properties or may be easier to process than known forms of the drug itself. For example, the salt may have different dissolution and solubility properties than the drug. Further, salts may be used as a convenient vehicle for drug delivery, and new drug formulations comprising salts of a given drug may have superior properties, for example, by facilitating better processing or handling characteristics, changing the dissolution profile in a favorable direction, or improving stability and shelf-life over existing formulations of the drug. As well, forming a salt is one way to avoid polymorph formation of the drug.

A salt of a drug (a supplement ingredient or an active pharmaceutical ingredient) is a distinct chemical composition between an ionizable drug that has been combined with a counter-ion (acid or base) to form a charge neutral complex. Salts generally possess distinct crystallographic and spectroscopic properties when combined in comparison to those of the individual drug and counter ion (acid or base). In a salt, the drug and counter-ion possess unique lattice positions within the unit cell of the crystal lattice. Crystallographic properties of salts can be analyzed as with other crystalline forms such as with X-ray powder diffraction (XRPD) among other techniques. Salts often also exhibit distinct thermal behavior compared with other forms of the corresponding drug. Thermal behavior may be analyzed by such techniques as capillary melting point, thermogravimetric analysis (TGA) and differential scanning calorimetry (DSC) to name a few. These techniques can be used to identify and characterize the salts.

A necessary consideration when designing salts, if the end goal is a potential marketed drug-product, is incorporating a suitable counter ion (acid or base) with an acceptable toxicity profile. Within the pharmaceutical industry, counter ions (acids or bases) are typically selected from the pharmaceutically accepted salt formers, generally regarded as safe (GRAS) and/or everything added to food in the United States (EAFUS) lists, due to previous occurrence of these molecules in FDA approved drug or food products. Utilizing naturally occurring compounds as counter ions (acids or bases) gives extension to the list of potential molecules accessible to the pharmaceutical industry and provides additional physiological benefits to the consumer.

Psilocin (also known as 4-hydroxy DMT, 4-OH-DMT or 4-hydroxy-N,N-dimethyltryptamine) has a CAS number 520-53-6 and is a tryptamine alkaloid and a psychedelic substance. It is found in most psychedelic mushrooms with its phosphorylated counterpart psilocybin. In fact, once ingested, psilocybin is rapidly metabolized to psilocin, which then acts on serotonin receptors in the prefrontal cortex. The mind-altering effects of psilocin typically last from one to three hours, although to individuals under the influence of psilocin, the effects may seem to last much longer, since the drug can distort the perception of time. Psilocin has a low toxicity and has no significant effect on dopamine receptors, and reports of lethal doses of the drug are rare. As a therapeutic drug psilocin may be suitable for the treatment of diseases or disorders, or symptoms of diseases or disorders, such as anxiety, depression, psychotic disorder, Schizophrenia, major depressive disorder (MDD), post-traumatic stress disorder (PTSD), obsessive-compulsive disorder, headaches and withdrawal from opioids, cocaine, heroin, amphetamines, and nicotine.

One crystal structure of psilocin has been reported in the literature by T. J. Petcher and H. P. Weber in 1974 published in the Journal of Chemical Society, Perkin Transactions 2, Pages 946-948 with a CCDC Ref Code of PSILIN. In fact, the field of psilocin crystalline materials appears to be a relatively unexplored landscape. There remains a need, therefore, for other psilocin crystalline forms.

SUMMARY OF THE INVENTION

The invention relates to new psilocin salts. In particular, the invention relates to a 1:1 psilocin benzoate salt; a 1:1 psilocin nicotinate salt; a 1:1 psilocin tartrate salt; a hemiacetone solvate of a 2:1 psilocin hemiadipate salt; a 1:1 psilocin fumarate salt; a 2:1 psilocin hemifumarate salt; a diethyl ether and/or ethanol-containing solvate of the 1:1 psilocin oxalate salt, wherein the stoichiometry of diethyl ether:ethanol:psilocin is about 0.2:0.1:1; a 1:1 psilocin DL-lactate salt; a 1:1 psilocin L-malate salt; and a 1:1 psilocin stearate salt. The invention relates to pharmaceutical compositions containing a psilocin salt of the invention and a pharmaceutically acceptable counter ion (acid). The psilocin salts may be used in the same way as psilocin. As a therapeutic drug, psilocin may be suitable for the treatment of diseases or disorders, or symptoms of diseases or disorders, such as anxiety, depression, psychotic disorder, Schizophrenia, major depressive disorder (MDD), post-traumatic stress disorder (PTSD), obsessive-compulsive disorder, headaches and withdrawal from opioids, cocaine, heroin, amphetamines, and nicotine as discussed above.

The molecular structure of psilocin is shown below:

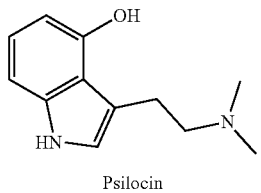

Psilocin

The invention further relates to a method of treating a disease, disorder or condition using psilocin the improvement comprising administering to a patient in need thereof a beneficial or therapeutically effective amount of psilocin, a composition, or a pharmaceutical composition of the invention.

BRIEF DESCRIPTION OF THE FIGURES

FIG. 1 shows an XRPD pattern of the 1:1 psilocin benzoate salt 1.
FIG. 2 shows an XRPD pattern indexing of the 1:1 psilocin benzoate salt 1.
FIG. 3 shows a DSC trace for the 1:1 psilocin benzoate salt 1.
FIG. 4 shows a TGA trace for the 1:1 psilocin benzoate salt 1.
FIG. 5 shows the $^1$H NMR spectrum of the 1:1 psilocin benzoate salt 1.
FIG. 6 shows an XRPD pattern of the 1:1 psilocin nicotinate salt 2.
FIG. 7 shows an XRPD pattern indexing of the 1:1 psilocin nicotinate salt 2.
FIG. 8 shows a DSC trace for the 1:1 psilocin nicotinate salt 2.
FIG. 9 shows a TGA trace for the 1:1 psilocin nicotinate salt 2.
FIG. 10 shows the $^1$H NMR spectrum of the 1:1 psilocin nicotinate salt 2.
FIG. 11 shows an XRPD pattern of the 1:1 psilocin tartrate salt 3.
FIG. 12 shows an XRPD pattern indexing of the 1:1 psilocin tartrate salt 3.
FIG. 13 shows a DSC trace for the 1:1 psilocin tartrate salt 3.
FIG. 14 shows a TGA trace for the 1:1 psilocin tartrate salt 3.
FIG. 15 shows the $^1$H NMR spectrum of the 1:1 psilocin tartrate salt 3.
FIG. 16 shows an XRPD pattern of the hemiacetone solvate of the 2:1 psilocin hemiadipate salt 4.
FIG. 17 shows an XRPD pattern indexing of the hemiacetone solvate of the 2:1 psilocin hemiadipate salt 4.
FIG. 18 shows a DSC trace for the hemiacetone solvate of the 2:1 psilocin hemiadipate salt 4.
FIG. 19 shows a TGA trace for the hemiacetone solvate of the 2:1 psilocin hemiadipate salt 4.
FIG. 20 shows the $^1$H NMR spectrum of the hemiacetone solvate of the 2:1 psilocin hemiadipate salt 4.
FIG. 21 shows an XRPD pattern of the 1:1 psilocin fumarate salt 5.
FIG. 22 shows an XRPD pattern indexing of the 1:1 psilocin fumarate salt 5.
FIG. 23 shows a DSC trace for the 1:1 psilocin fumarate salt 5.
FIG. 24 shows a TGA trace for the 1:1 psilocin fumarate salt 5.
FIG. 25 shows the $^1$H NMR spectrum of the 1:1 psilocin fumarate salt 5.
FIG. 26 shows an XRPD pattern of the 2:1 psilocin hemifumarate salt 6.
FIG. 27 shows an XRPD pattern indexing of the 2:1 psilocin hemifumarate salt 6.
FIG. 28 shows a DSC trace for the 2:1 psilocin hemifumarate salt 6.
FIG. 29 shows a TGA trace for the 2:1 psilocin hemifumarate salt 6.
FIG. 30 shows the $^1$H NMR spectrum of the 2:1 psilocin hemifumarate salt 6.
FIG. 31 shows an XRPD pattern of the solvate of the 1:1 psilocin oxalate salt 7.
FIG. 32 shows an XRPD pattern indexing of the solvate of the 1:1 psilocin oxalate salt 7.
FIG. 33 shows a DSC trace for the solvate of the 1:1 psilocin oxalate salt 7.
FIG. 34 shows a TGA trace for the solvate of the 1:1 psilocin oxalate salt 7.
FIG. 35 shows the $^1$H NMR spectrum of the solvate of the 1:1 psilocin oxalate salt 7.
FIG. 36 shows an XRPD pattern of the 1:1 psilocin DL-lactate salt 8.
FIG. 37 shows an XRPD pattern indexing of the 1:1 psilocin DL-lactate salt 8.
FIG. 38 shows a DSC trace for the 1:1 psilocin DL-lactate salt 8.
FIG. 39 shows a TGA trace for the 1:1 psilocin DL-lactate salt 8.
FIG. 40 shows the $^1$H NMR spectrum of the 1:1 psilocin DL-lactate salt 8.
FIG. 41 shows an XRPD pattern of the 1:1 psilocin L-malate salt 9.
FIG. 42 shows an XRPD pattern indexing of the 1:1 psilocin L-malate salt 9.
FIG. 43 shows a DSC trace for the 1:1 psilocin L-malate salt 9.
FIG. 44 shows a TGA trace for the 1:1 psilocin L-malate salt 9.
FIG. 45 shows the $^1$H NMR spectrum of the 1:1 psilocin L-malate salt 9.
FIG. 46 shows an XRPD pattern of the 1:1 psilocin stearate salt 10.
FIG. 47 shows an XRPD pattern indexing of the 1:1 psilocin stearate salt 10.
FIG. 48 shows a DSC trace for the 1:1 psilocin stearate salt 10.
FIG. 49 shows a TGA trace for the 1:1 psilocin stearate salt 10.
FIG. 50 shows the $^1$H NMR spectrum of the 1:1 psilocin stearate salt 10.

DETAILED DESCRIPTION OF THE INVENTION

The invention relates to new crystalline salt forms of psilocin. The crystalline salts, a 1:1 psilocin benzoate salt, a 1:1 psilocin nicotinate salt, a 1:1 psilocin tartrate salt, a hemiacetone solvate of a 2:1 psilocin hemiadipate salt, a 1:1 psilocin fumarate salt, a 2:1 psilocin hemifumarate salt, a solvate of a 1:1 psilocin oxalate salt, a 1:1 psilocin DL-lactate salt, a 1:1 psilocin L-malate salt, and a 1:1 psilocin stearate salt were prepared and characterized by X-ray powder diffraction (XRPD), differential scanning calorimetry (DSC), thermogravimetric analysis (TGA) and solution proton nuclear magnetic resonance CH NMR) as described in the examples below.

Therapeutic Uses of the Crystalline Psilocin Form

Psilocin (also known as 4-hydroxy DMT, 4-OH-DMT or 4-hydroxy-N,N-dimethyltryptamine) is known to be beneficial for human health. The invention also provides therapeutic and beneficial uses of the psilocin salts and methods for its delivery, and compositions, such as pharmaceutical dosage forms, containing the crystalline psilocin salts, to humans. The crystalline psilocin salts of the invention may then be used to treat diseases, disorders, and conditions, such as those discussed above, and to provide beneficial treatment for humans.

The invention then also relates to the method of treating such a disease, disorder or condition comprising the step of administering to a patient in need thereof a beneficial or therapeutically effective amount of a crystalline psilocin salt, a composition, or a pharmaceutical composition of the invention. Similarly, the invention relates to the use of psilocin to treat a disease, disorder or condition characterized by administering to a patient in need thereof a beneficial or therapeutically effective amount of a crystalline psilocin salt, a composition, or a pharmaceutical composition of the invention.

The invention then also relates to the method of treating (or the use of crystalline psilosin salts to treat) such a disease, disorder, or condition by administering to a human or animal patient in need thereof a therapeutically effective or beneficial amount of the crystalline psilocin salts of the invention or of administering to a human or animal patient in need thereof a therapeutic composition containing the crystalline psilocin of the invention. The term "treatment" or "treating" means any treatment of a disease, disorder or condition in a mammal, including: preventing or protecting against the disease, disorder or condition, that is, causing the clinical symptoms not to develop; inhibiting the disease, disorder or condition, that is arresting or suppressing, the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder or condition. The term "protection" is meant to include "prophylaxis."

The crystalline psilocin salts of the invention may be administered at psilocin dosage levels of about 0.001 mg/kg to about 1.0 mg/kg, from about 0.01 mg/kg to about 0.5 mg/kg, or from about 0.1 mg/kg to about 0.20 mg/kg of subject body weight per day, one or more times a day, to obtain the desired effect. It will also be appreciated that, where appropriate, dosages smaller than 0.001 mg/kg or greater than 1.0 mg/kg (for example 1-2 mg/kg) can be administered to a subject in need thereof.

Compositions Containing the Crystalline Psilocin Salts

The invention also relates to compositions, such as dietary supplement and pharmaceutical compositions, comprising a beneficial or therapeutically effective amount of the crystalline psilocin salts according to the invention and a carrier, such as a pharmaceutically acceptable carrier (also known as a pharmaceutically acceptable excipient). The compositions and pharmaceutical dosage forms may be administered using any amount, any form of composition, dietary supplement or pharmaceutical composition and any route of administration a beneficial or therapeutically effective for treatment. As mentioned above, these pharmaceutical compositions are therapeutically useful to treat or prevent disorders such as those discussed above.

A pharmaceutical composition of the invention may be in any pharmaceutical dosage form known in the art which contains the crystalline psilocin salts according to the invention. A composition, particularly a pharmaceutical composition, may be, for example, a tablet, a capsule, a liquid suspension, an injectable composition, a topical composition, an inhalable composition, or a transdermal composition. The compositions, particularly pharmaceutical compositions generally contain, for example, about 0.1% to about 99.9% by weight of the crystalline psilocin salts, for example, about 0.5% to about 99% by weight of the crystalline psilocin salts of the invention and, for example, 99.5% to 0.5% by weight of at least one suitable pharmaceutically acceptable carrier and/or excipient. The composition may also be between about 5% and about 75% by weight of the crystalline psilocin salts of the invention with the rest being at least one suitable pharmaceutical acceptable carrier and/or excipient, as discussed below.

The dosage form an appropriate pharmaceutically acceptable carrier and/or excipient in a desired dosage, as known by those of skill in the art, the pharmaceutical compositions of this disclosure can be administered to humans and other animals orally, rectally, parenterally, intravenously, intracisternally, intravaginally, intraperitoneally, topically (as by powders, ointments, or drops), buccally, as an oral or nasal spray, or the like, depending on the location and severity of the condition being treated. In one embodiment, the pharmaceutical composition is with an oral unit dosage form.

Compositions, particularly pharmaceutical compositions, of the invention include a beneficial or therapeutically effective amount of the crystalline psilocin salts of the invention and a carrier such as a pharmaceutically acceptable carrier and/or excipient. Such pharmaceutically acceptable carriers and excipients, including, without limitation, binders, fillers, lubricants, emulsifiers, suspending agents, sweeteners, flavorings, preservatives, buffers, wetting agents, disintegrants, effervescent agents, and other conventional excipients and additives. The pharmaceutical compositions of the invention can thus include any one or a combination of the following: a pharmaceutically acceptable carrier or excipient; other medicinal agent(s); pharmaceutical agent(s); adjuvants; buffers; preservatives; diluents; and various other pharmaceutical additives and agents known in the art. These additional formulation additives and agents will often be biologically inactive and can be administered to humans without causing deleterious side effects or interactions.

Suitable additives may include, but are not limited to, microcrystalline cellulose, lactose, sucrose, fructose, glucose, dextrose, other sugars, di-basic calcium phosphate, calcium sulfate, cellulose, methylcellulose, cellulose derivatives, kaolin, mannitol, lactitol, maltitol, xylitol, sorbitol, other sugar alcohols, dry starch, dextrin, maltodextrin, other polysaccharides, or mixtures thereof.

In one embodiment of the invention the pharmaceutical composition is an oral unit dosage form containing a therapeutically effective amount of the crystalline psilocin salts of the invention and a pharmaceutically acceptable carrier and/or excipient. Exemplary oral unit dosage forms for use in the present disclosure include tablets, capsules, powders, suspensions, and lozenges, which may be prepared by any conventional method of preparing pharmaceutical oral dosage forms. Oral unit dosage forms, such as tablets, may contain one or more pharmaceutically acceptable carriers and/or excipients such as known in the art as discussed above, including but not limited to, release modifying agents, glidants, compression aides, disintegrants, effervescent agents, lubricants, binders, diluents, flavors, flavor enhancers, sweeteners, and preservatives.

Tablet dosage forms may be partially or fully coated, sub-coated, uncoated, and may include channeling agents. The ingredients are selected from a wide variety of excipients known in the pharmaceutical formulation art. Depending on the desired properties of the oral dosage form, any number of ingredients may be selected alone or in combination for their known use in preparing such dosage forms as tablets.

EXAMPLES

The following reagents and analytical methods were used to prepare and characterize the psilocin salts 1-10 of the invention. For work done at room temperature (RT) that is generally about 25° C.

Reagents: Psilocin was acquired from Cayman Chemical and used as received. All other chemicals were purchased from various suppliers and used without further purification.

X-ray Powder Diffraction (XRPD): XRPD patterns for psilocin salts 1-7 were collected with a PANalytical X'Pert PRO MPD or a PANalytical Empyrean diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640f) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5.

XRPD patterns for psilocin salts 8-10 were collected with the Rigaku Smart-Lab X-ray diffraction system configured for reflection Bragg-Brentano geometry using a line source X-ray beam. The x-ray source was a Cu Long Fine Focus tube that was operated at 40 kV and 44 ma. That source provided an incident beam profile at the sample that changes from a narrow line at high angles to a broad rectangle at low angles. Beam conditioning slits were used on the line X-ray source to ensure that the maximum beam size was less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam was controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ.

X-ray Powder Diffraction Indexing: The patterns for psilocin salts 1-7 were indexed using proprietary software [TRIADS™ is covered by U.S. Pat. No. 8,576,985] or X'Pert High Score Plus 2.2a (2.2.1). The patterns for psilocin salts 8-10 were indexed using TOPAS 6 (TOPAS 6.0.0.9, 2018 Bruker AXS GmbH, Karlsruhe, Germany) along with Pawley refinements. Refinements are performed on all parameters simultaneously to a convergence of 0.001 in $X^2$. Indexing is the process of determining the size and shape of the crystallographic unit cell given the peak positions in a diffraction pattern. The term gets its name from the assignment of Miller index labels to individual peaks. If all of the peaks in a pattern are indexed by a single unit cell, this is strong evidence that the sample contains a single crystalline phase. Given the indexing solution, the unit cell volume may be calculated directly. Indexing is also a robust description of a crystalline form and provides a concise summary of all available peak positions for that phase at a particular thermodynamic state point. Within the figure referenced for a given indexed XRPD pattern, agreement between the allowed peak positions, with the indexing marked with either red bars in a box below the XRPD pattern (for salts 1-7 shown in FIGS. 2, 7, 12, 17, 22, 27, and 32) or blue tick marks marked on the x-axis below the XPRD pattern (for salts 8-10 in FIGS. 37, 42, and 47), and the observed peaks indicates a consistent unit cell determination. Space groups consistent with the assigned extinction symbol, unit cell parameters, and derived quantities are either tabulated below the figures for salts 1-7 shown in FIGS. 2, 7, 12, 17, 22, 27, and 32, or described below for salts 8-10 when discussing FIGS. 37, 42, and 47.

Differential Scanning calorimetry (DSC): DSC analyses were performed on psilocin salts 1-7 using a Mettler-Toledo DSC3+ differential scanning calorimeter. A tau lag adjustment was performed with indium, tin, and zinc. The temperature and enthalpy were adjusted with octane, phenyl salicylate, indium, tin and zinc. The adjustment was then verified with octane, phenyl salicylate, indium, tin, and zinc. The sample was placed into a hermetically sealed aluminum DSC pan, the weight was accurately recorded, and the sample was inserted into the DSC cell. A weighed aluminum pan configured as the sample pan was placed on the reference side of the cell. The pan lid was pierced prior to sample analysis.

DSC analyses were performed on psilocin salts 8-10 using a TA Instruments Q2500 Discovery Series instrument. The instrument temperature calibration was performed using indium. The DSC cell was kept under a nitrogen purge of ~50 mL per minute during each analysis. The sample was placed in a standard, crimped, aluminum pan and was heated from approximately 25° C. to 350° C. at a rate of 10° C. per minute.

Thermogravimetric Analysis (TGA): Thermogravimetric analyses were performed on psilocin salts 1-7 using a Mettler-Toledo TGA/DSC3+ analyzer. Temperature and enthalpy adjustments were performed using indium, tin, zinc, and phenyl salicylate, and then verified with indium. The balance was verified with calcium oxalate. The sample was placed in an aluminum pan. The pan was hermetically sealed, the lid pierced, and the pan was then inserted into the TG furnace. A weighed aluminum pan configured as the sample pan was placed on the reference platform. The furnace was heated under nitrogen. Thermogravimetric analyses typically experience a period of equilibration at the start of each analysis, indicated by red parentheses on the thermograms; the starting temperature for relevant weight loss calculations is selected at a point beyond this region (typically above 35° C.) for accuracy.

TGA analyses were performed on psilocin salts 8-10 using a TA Instruments Q5500 Discovery Series instrument. The instrument balance was calibrated using class M weights and the temperature calibration was performed using alumel. The nitrogen purge was ~40 mL per minute at the balance and ~60 mL per minute at the furnace. Each sample was placed into a pre-tared platinum pan and heated from approximately 25° C. to 350° C. at a rate of 10° C. per minute.

Solution $^1$H Nuclear Magnetic Resonance (NMR) Spectroscopy: The solution NMR spectra were acquired on psilocin salts 1-7 with an Avance 600 MHz spectrometer. The samples were prepared by dissolving approximately 5-10 mg of sample in methanol-$d_4$ containing TMS. The data acquisition parameters are provided on the spectrum.

The solution NMR spectra were acquired on psilocin salts 8-10 with a Bruker Avance II 400 spectrometer. Samples were prepared by dissolving material in DMSO-d6. The solutions were filtered and placed into individual 5-mm NMR tubes for subsequent spectral acquisition. The temperature controlled (295K) $^1$H NMR spectra acquired on the Avance II 400 utilized a 5-mm cryoprobe operating at an observing frequency of 400.18 MHz.

Ion Chromatography (IC): A multi-element anion standard solution (Alltech Anion Mix 5, Part No. 269110, 50 µg/mL) was diluted 5-fold with water to a working concentration of 2000 µg/L. Ion chromatography analyses were performed using a Dionex ICS-5000$^+$ series ion chromatograph. The ICS-5000$^+$ consists of two chromatography systems that share an autosampler. The system used for anion detection was equipped with a gradient pump, an eluent generator module, a conductivity detector, and a suppressor (AERS 4 mm). A Dionex UTAC-ULP1 5×23 mm concentrator column was installed in place of the sample loop. A Dionex IonPac™ AG19 4×50 mm guard column and a Dionex IonPac™ AS19 4×250 mm analytical column were installed. Water (18.2 MΩ, dispensed from ELGA Purelab Flex 2) was used to fill the eluent reservoir, for standard preparations, and for autosampler flush. DMSO was used for sample preparation and associated blank injections.

Example 1: 1:1 Psilocin Benzoate Salt, 1

1.1 Preparation of the 1:1 Psilocin Benzoate Salt, 1

A slightly turbid suspension of 200.0 mg of psilocin (Cayman Chemical, lot 0594443) in 20 mL of diethyl ether (Sigma Aldrich, lot SHBL6577) was decolorized with activated charcoal and filtered through a 0.2-µm nylon filter. Approximately half of the clear solution was added to 59.8 mg of benzoic acid (Sigma Aldrich, lot MKCL7479). The sample was agitated by hand until precipitates formed. The sample was left undisturbed at ambient temperature for one day and then the precipitant was isolated by water aspirated vacuum filtration.

1.2 XRPD Characterization of the 1:1 Psilocin Benzoate Salt, 1

The experimental XRPD pattern of the 1:1 psilocin benzoate salt 1 is shown in FIG. 1. Table 1 lists the angles, ° 2θ±0.2° 2θ, and d-spacing of the peaks identified in the experimental XRPD pattern of FIG. 1. The entire list of peaks, or a subset thereof, may be sufficient to characterize the salt, as well as by an XRPD pattern substantially similar (that is, identifiable by one of ordinary skill using this method within experimental variations) to FIG. 1. For example, a 1:1 psilocin benzoate salt of the invention may be characterized by a powder X-ray diffraction pattern having at least three, four, or five peaks selected from 9.4, 12.3, 14.5, 16.3, 16.4, 18.1, 18.9, 19.2, 19.7, 21.3, 22.6, 22.9, 24.7, 24.8, and 26.0° 2θ±0.2° 2θ.

TABLE 1

| 2-theta (deg) | d-spacing (Å) | Relative Intensity (I) |
| --- | --- | --- |
| 9.4 | 9.41 | 13 |
| 10.9 | 8.11 | 8 |
| 12.3 | 7.20 | 24 |
| 13.3 | 6.63 | 5 |
| 14.5 | 6.11 | 54 |
| 16.3 | 5.43 | 40 |
| 16.4 | 5.40 | 54 |
| 18.1 | 4.89 | 100 |
| 18.9 | 4.70 | 35 |
| 19.2 | 4.61 | 55 |
| 19.7 | 4.50 | 20 |
| 19.9 | 4.45 | 8 |
| 20.7 | 4.28 | 4 |
| 21.3 | 4.16 | 18 |
| 21.9 | 4.05 | 4 |
| 22.6 | 3.93 | 29 |
| 22.9 | 3.89 | 33 |
| 23.8 | 3.74 | 6 |
| 24.1 | 3.70 | 5 |
| 24.7 | 3.60 | 17 |
| 24.8 | 3.58 | 27 |
| 25.6 | 3.47 | 6 |
| 26.0 | 3.42 | 54 |
| 26.3 | 3.39 | 11 |
| 26.9 | 3.31 | 4 |
| 27.6 | 3.23 | 11 |
| 27.9 | 3.19 | 4 |
| 28.5 | 3.13 | 7 |
| 29.0 | 3.08 | 4 |
| 29.8 | 3.00 | 3 |
| 29.9 | 2.98 | 4 |

1.3 XRPD Pattern Indexing of the 1:1 Psilocin Benzoate Salt, 1

The XRPD indexing description, FIG. 2, shows a primitive monoclinic crystal system with a space group of P2$_1$/c (14). The unit cell parameters are a=9.633 Å, b=11.526 Å, c=16.873 Å, α=90°, β=106.23°, γ=90° with a unit cell volume of 1798.7 Å$^3$.

1.4 DSC of the 1:1 Psilocin Benzoate Salt, 1

The differential scanning calorimetry (DSC) trace, FIG. 3, shows a single endotherm with a peak maximum of about 237° C. corresponding to the melt of the salt.

1.5 TGA of the 1:1 Psilocin Benzoate Salt, 1

The thermal gravimetric analysis (TGA) trace, FIG. 4, shows no significant weight loss prior to the salt melt temperature near 200° C.

1.6 $^1$H NMR Spectrum of the 1:1 Psilocin Benzoate Salt, 1

The $^1$H NMR spectrum of the 1:1 psilocin benzoate salt shown in FIG. 5 displays the following peaks: $^1$H NMR (600 MHz, CD$_3$OD) δ: 7.95 (2H), 7.34-7.42 (3H), 6.99 (1H), 6.83-6.90 (2H), 6.37 (1H), 3.40 (2H), 3.25 (2H), and 2.83 (6H). The multiplet at 6.37 ppm in the $^1$H NMR spectrum corresponds to 1 proton of psilocin. Comparison of the integration of this peak with the multiplet at 7.95 ppm, which corresponds to two of the aromatic ring protons of benzoic acid, indicates that the salt has a psilocin:benzoate stoichiometry of 1:1.

Example 2: 1:1 Psilocin Nicotinate Salt, 2

2.1 Preparation of the 1:1 Psilocin Nicotinate Salt, 2

A solution of 207.1 mg of psilocin (Cayman Chemical, lot 0594443) in 10 mL of isopropyl alcohol (Fisher Scientific, lot 182481) was generated at 60° C. The solution was decolorized with activated charcoal and filtered through a 0.2-μm nylon filter. A 5-mL aliquot of the clear solution was added to 60.7 mg of nicotinic acid (Sigma Aldrich, lot SLBH9954V). The suspension was briefly heated to 60° C. until fully dissolved. The clear solution was refrigerated for one day and then stored in the freezer for an additional 5 days. The precipitant was isolated by water aspirated vacuum filtration and briefly dried under a nitrogen purge.

2.2 XRPD Characterization of the 1:1 Psilocin Nicotinate Salt, 2

The experimental XRPD pattern of the 1:1 psilocin nicotinate salt 2 is shown in FIG. 6. Table 2 lists the angles, ° 2θ±0.2° 2θ, and d-spacing of the peaks identified in the experimental XRPD pattern of FIG. 6. The entire list of peaks, or a subset thereof, may be sufficient to characterize the salt, as well as by an XRPD pattern substantially similar (that is, identifiable by one of ordinary skill using this method within experimental variations) to FIG. 6. For example, a 1:1 psilocin nicotinate salt of the invention may be characterized by a powder X-ray diffraction pattern having at least three, four, or five peaks selected from 10.2, 11.4, 12.4, 14.0, 15.1, 15.6, 17.2, 17.5, 18.4, 19.2, 20.0, 22.4, 23.5, 24.1, 25.0, and 25.2° 2θ±0.2° 2θ.

TABLE 2

| 2-theta (deg) | d-spacing (Å) | Relative Intensity (I) |
| --- | --- | --- |
| 9.7 | 9.10 | 10 |
| 10.2 | 8.66 | 14 |
| 11.4 | 7.77 | 28 |
| 11.8 | 7.49 | 5 |
| 12.4 | 7.13 | 37 |
| 14.0 | 6.33 | 14 |
| 15.1 | 5.88 | 22 |
| 15.6 | 5.69 | 17 |
| 17.2 | 5.16 | 99 |
| 17.5 | 5.06 | 30 |
| 18.4 | 4.83 | 41 |
| 19.2 | 4.61 | 35 |
| 20.0 | 4.43 | 37 |
| 20.8 | 4.27 | 10 |
| 21.1 | 4.20 | 9 |
| 22.4 | 3.98 | 39 |
| 23.5 | 3.78 | 100 |
| 24.1 | 3.69 | 30 |
| 25.0 | 3.56 | 18 |
| 25.2 | 3.53 | 20 |
| 26.9 | 3.31 | 6 |
| 27.5 | 3.25 | 10 |
| 27.7 | 3.22 | 9 |
| 29.3 | 3.05 | 8 |
| 30.5 | 2.93 | 9 |

2.3 XRPD Pattern Indexing of the 1:1 Psilocin Nicotinate Salt, 2

The XRPD indexing description, FIG. 7, shows a triclinic crystal system with a space group of P1(1) or P$\bar{1}$ (2). The unit cell parameters are a=9.343 Å, b=9.595 Å, c=11.079 Å, α=76.04°, β=71.26°, γ=74.13° with a unit cell volume of 891.7 Å$^3$.

2.4 DSC of the 1:1 Psilocin Nicotinate Salt, 2

The differential scanning calorimetry (DSC) trace, FIG. 8, shows a single endotherm with a peak maximum of about 189° C. corresponding to the melt of the salt.

2.5 TGA of the 1:1 Psilocin Nicotinate Salt, 2

The thermal gravimetric analysis (TGA) trace, FIG. 9, shows no significant weight loss prior to the salt melt temperature near 187° C.

2.6 $^1$H NMR Spectrum of the 1:1 Psilocin Nicotinate Salt, 2

The $^1$H NMR spectrum of the 1:1 psilocin nicotinate salt shown in FIG. 10 displays the following peaks: $^1$H NMR (600 MHz, CD$_3$OD) δ: 9.06 (1H), 8.53 (1H), 8.31 (1H), 7.43 (1H), 7.01 (1H), 6.83-6.90 (2H), 6.37 (1H), 3.48 (2H), 3.26 (2H), and 2.89 (6H). The multiplet at 6.37 ppm in the $^1$H NMR spectrum corresponds to 1 proton of psilocin. Comparison of the integration of this peak with the multiplet at 9.06 ppm, which corresponds to one of the aromatic ring protons of nicotinic acid, indicates that the salt has a psilocin:nicotinate stoichiometry of 1:1.

Example 3: 1:1 Psilocin Tartrate Salt, 3

3.1 Preparation of the 1:1 Psilocin Tartrate Salt, 3

A solution of 69.6 mg of psilocin (Cayman Chemical, lot 0594443) in 2 mL of acetone (Fisher Scientific, lot 494118) was decolorized with activated charcoal and filtered through a 0.2-μm nylon filter. The clear solution was added to 50.1 mg of L-(+)-tartaric acid (Sigma Aldrich, lot BCBT1076), providing a turbid suspension. An additional 2 mL of acetone was added and the suspension was slurried for 6 days at room temperature. The precipitant was isolated by water aspirated vacuum filtration.

3.2 XRPD Characterization of the 1:1 Psilocin Tartrate Salt, 3

The experimental XRPD pattern of the 1:1 psilocin tartrate salt 3 is shown in FIG. 11. Table 3 lists the angles, ° 2θ±0.2° 2θ, and d-spacing of the peaks identified in the experimental XRPD pattern of FIG. 11. The entire list of peaks, or a subset thereof, may be sufficient to characterize the salt, as well as by an XRPD pattern substantially similar (that is, identifiable by one of ordinary skill using this method within experimental variations) to FIG. 11. For example, a 1:1 psilocin tartrate salt of the invention may be characterized by a powder X-ray diffraction pattern having at least three, four, or five peaks selected from 13.4, 14.7, 15.9, 17.2, 18.8, 20.2, 20.8, 21.8, 22.6, 23.4, 24.6, 24.8, 25.5, and 26.6° 2θ±0.2° 2θ.

TABLE 3

| 2-theta (deg) | d-spacing (Å) | Relative Intensity (I) |
| --- | --- | --- |
| 6.68 | 13.22 | 7 |
| 11.2 | 7.87 | 3 |
| 12.7 | 6.99 | 8 |
| 13.4 | 6.60 | 15 |
| 14.7 | 6.02 | 24 |
| 15.9 | 5.58 | 13 |
| 16.2 | 5.46 | 7 |
| 17.2 | 5.14 | 100 |
| 18.8 | 4.71 | 43 |
| 20.0 | 4.45 | 34 |
| 20.2 | 4.40 | 28 |
| 20.8 | 4.26 | 14 |
| 21.8 | 4.07 | 36 |
| 22.6 | 3.93 | 52 |
| 22.9 | 3.88 | 7 |
| 23.2 | 3.84 | 7 |
| 23.4 | 3.80 | 14 |
| 23.7 | 3.76 | 12 |
| 24.6 | 3.62 | 15 |
| 24.8 | 3.59 | 22 |
| 25.5 | 3.49 | 17 |
| 25.8 | 3.46 | 6 |
| 26.1 | 3.42 | 4 |
| 26.6 | 3.35 | 17 |

TABLE 3-continued

| 2-theta (deg) | d-spacing (Å) | Relative Intensity (I) |
|---|---|---|
| 27.0 | 3.30 | 7 |
| 27.4 | 3.25 | 6 |
| 27.8 | 3.21 | 3 |
| 28.1 | 3.17 | 5 |
| 28.5 | 3.20 | 14 |
| 29.0 | 3.08 | 6 |
| 29.2 | 3.06 | 7 |
| 29.5 | 3.03 | 9 |
| 29.7 | 3.01 | 5 |
| 29.9 | 2.99 | 5 |
| 31.0 | 2.89 | 10 |
| 31.5 | 2.84 | 7 |
| 32.0 | 2.80 | 9 |
| 32.2 | 2.78 | 6 |
| 32.7 | 2.74 | 3 |
| 33.0 | 2.71 | 5 |
| 33.7 | 2.66 | 3 |
| 33.9 | 2.64 | 5 |
| 34.3 | 2.61 | 11 |
| 34.9 | 2.57 | 5 |

3.3 XRPD Pattern Indexing of the 1:1 Psilocin Tartrate Salt, 3

The XRPD indexing description, FIG. 12, shows a primitive orthorhombic crystal system with a space group of $P2_12_12_1$ (19). The unit cell parameters are a=7.588 Å, b=8.236 Å, c=26.409 Å, α=90°, β=90°, γ=90° with a unit cell volume of 1650.4 Å$^3$.

3.4 DSC of the 1:1 Psilocin Tartrate Salt, 3

The differential scanning calorimetry (DSC) trace, FIG. 13, shows a single endotherm with a peak maximum of about 167° C. corresponding to the melt of the salt.

3.5 TGA of the 1:1 Psilocin Tartrate Salt, 3

The thermal gravimetric analysis (TGA) trace, FIG. 14, shows no significant weight loss prior to the salt melt temperature near 164° C.

3.6 $^1$H NMR Spectrum of the 1:1 Psilocin Tartrate Salt, 3

The $^1$H NMR spectrum of the 1:1 psilocin tartrate salt shown in FIG. 15 displays the following peaks: $^1$H NMR (600 MHz, CD$_3$OD) δ: 7.02 (1H), 6.85-6.90 (2H), 6.37 (1H), 4.41 (2H), 3.48 (2H), 3.27-3.31 (2H), and 2.90 (6H). The multiplet at 6.37 ppm in the $^1$H NMR spectrum corresponds to 1 proton of psilocin. Comparison of the integration of this peak with the singlet at 4.41 ppm, which corresponds to two of the protons of tartaric acid, indicates that the salt has a psilocin:tartrate stoichiometry of 1:1.

Example 4: Hemiacetone Solvate of the 2:1 Psilocin Hemiadipate Salt, 4

4.1 Preparation of the Hemiacetone Solvate of the 2:1 Psilocin Hemiadipate Salt, 4

A solution of 62.4 mg of psilocin (Cayman Chemical, lot 0594443) in 2 mL of acetone (Fisher Scientific, lot 494118) was decolorized with activated charcoal and filtered through a 0.2-μm nylon filter. The clear solution was added to 43.6 mg of adipic acid (Sigma Aldrich, lot MKBP7307V) resulting in oil. The oily suspension was slurried for 6 days at room temperature until precipitation occurred. The precipitant was isolated by water aspirated vacuum filtration.

4.2 XRPD Characterization of the Hemiacetone Solvate of the 2:1 Psilocin Hemiadipate Salt, 4

The experimental XRPD pattern of the hemiacetone solvate of the 2:1 psilocin hemiadipate salt, 4 is shown in FIG. 16. Table 4 lists the angles, ° 2θ±0.2° 2θ, and d-spacing of the peaks identified in the experimental XRPD pattern of FIG. 16. The entire list of peaks, or a subset thereof, may be sufficient to characterize the salt, as well as by an XRPD pattern substantially similar (that is, identifiable by one of ordinary skill using this method within experimental variations) to FIG. 16. For example, a hemiacetone solvate of the 2:1 psilocin hemiadipate salt of the invention may be characterized by a powder X-ray diffraction pattern having at least three, four, or five peaks selected from 8.4, 10.3, 10.8, 13.4, 15.0, 15.3, 15.5, 15.8, 16.9, 18.2, 20.1, 21.6, 21.8, 22.9, and 28.0° 2θ±0.2° 2θ.

TABLE 4

| 2-theta (deg) | d-spacing (Å) | Relative Intensity (I) |
|---|---|---|
| 7.8 | 11.21 | 4 |
| 8.4 | 10.47 | 14 |
| 10.3 | 8.56 | 16 |
| 10.8 | 8.22 | 22 |
| 12.8 | 6.93 | 3 |
| 13.4 | 6.62 | 24 |
| 15.0 | 5.91 | 19 |
| 15.3 | 5.78 | 39 |
| 15.5 | 5.70 | 18 |
| 15.8 | 5.60 | 100 |
| 16.9 | 5.25 | 36 |
| 17.2 | 5.16 | 4 |
| 18.2 | 4.86 | 24 |
| 18.8 | 4.73 | 8 |
| 19.4 | 4.57 | 3 |
| 20.1 | 4.41 | 19 |
| 20.3 | 4.38 | 6 |
| 20.8 | 4.28 | 4 |
| 21.2 | 4.19 | 3 |
| 21.6 | 4.11 | 52 |
| 21.8 | 4.07 | 28 |
| 22.1 | 4.02 | 5 |
| 22.9 | 3.88 | 58 |
| 23.4 | 3.80 | 6 |
| 23.9 | 3.73 | 6 |
| 24.6 | 3.61 | 4 |
| 24.8 | 3.59 | 4 |
| 25.5 | 3.49 | 13 |
| 25.9 | 3.44 | 11 |
| 26.4 | 3.37 | 5 |
| 26.9 | 3.31 | 4 |
| 27.5 | 3.24 | 3 |
| 28.0 | 3.19 | 43 |
| 28.3 | 3.15 | 9 |

4.3 XRPD Pattern Indexing of the Hemiacetone Solvate of the 2:1 Psilocin Hemiadipate Salt, 4

The XRPD indexing description, FIG. 17, shows a primitive orthorhombic crystal system with a space group of Pbcn (60). The unit cell parameters are a=11.826 Å, b=22.402 Å, c=13.236 Å, α=90°, β=90°, γ=90° with a unit cell volume of 3506.6 Å$^3$.

4.4 DSC of the Hemiacetone Solvate of the 2:1 Psilocin Hemiadipate Salt, 4

The differential scanning calorimetry (DSC) trace, FIG. 18, shows multiple endothermic events with peak maxima at about 49, 102, 135 and 155° C. along with a single endotherm with a peak maximum of about 179° C.

4.5 TGA of the Hemiacetone Solvate of the 2:1 Psilocin Hemiadipate Salt, 4

The thermal gravimetric analysis (TGA) trace, FIG. 19, shows a weight loss of about 8% up to about 166° C. which is likely to be the loss of the acetone which is part of the crystal lattice.

4.6 $^1$H NMR Spectrum of the Hemiacetone Solvate of the 2:1 Psilocin Hemiadipate Salt, 4

The $^1$H NMR spectrum of the hemiacetone solvate of the 2:1 psilocin hemiadipate salt shown in FIG. 20 displays the following peaks: $^1$H NMR (600 MHz, CD$_3$OD) δ: 6.97 (1H), 6.83-6.90 (2H), 6.36 (1H), 3.28-3.30 (2H), 3.20-3.22 (2H), 2.75 (6H), 2.20-2.25 (2H), 2.15 (3H), and 1.63-1.67 (2H). The multiplet at 6.36 ppm in the $^1$H NMR spectrum corresponds to 1 proton of psilocin. Comparison of the integration of this peak with the multiplet at 1.63-1.67 ppm, which corresponds to 2 of the protons of adipic acid, indicates that the salt has a psilocin:adipate stoichiometry of 2:1. Furthermore, comparison of the integration of the singlet at 2.15 ppm, which corresponds to 3 protons of acetone indicates that the salt contains 0.5 equivalents of acetone solvent.

Example 5: 1:1 Psilocin Fumarate Salt, 5

5.1 Preparation of the 1:1 Psilocin Fumarate Salt, 5

A solution of 60.7 mg of psilocin (Cayman Chemical, lot 0594443) in 2 mL of acetone (Fisher Scientific, lot 494118) was decolorized with activated charcoal and filtered through a 0.2-μm nylon filter. The clear solution was added to 32.6 mg of fumaric acid (Sigma Aldrich, lot MKBB7131), providing immediate precipitation. The suspension was slurried for 6 days at room temperature. The precipitant was isolated by water aspirated vacuum filtration.

5.2 XRPD Characterization of the 1:1 Psilocin Fumarate Salt, 5

The experimental XRPD pattern of the 1:1 psilocin fumarate salt 5 is shown in FIG. 21. Table 5 lists the angles, ° 2θ±0.2° 2θ, and d-spacing of the peaks identified in the experimental XRPD pattern of FIG. 21. The entire list of peaks, or a subset thereof, may be sufficient to characterize the salt, as well as by an XRPD pattern substantially similar (that is, identifiable by one of ordinary skill using this method within experimental variations) to FIG. 21. For example, a 1:1 psilocin fumarate salt of the invention may be characterized by a powder X-ray diffraction pattern having at least three, four, or five peaks selected from 6.9, 10.5, 12.2, 12.6, 15.8, 16.1, 16.7, 17.0, 18.3, 19.1, 20.3, 20.8, 22.6, 23.1, 23.3, 23.5, 24.2, 25.3, 25.9, and 27.8° 2θ±0.2° 2θ.

TABLE 5

| 2-theta (deg) | d-spacing (Å) | Relative Intensity (I) |
| --- | --- | --- |
| 6.9 | 12.86 | 26 |
| 10.5 | 8.39 | 84 |
| 12.2 | 7.26 | 56 |
| 12.6 | 7.03 | 30 |
| 13.8 | 6.44 | 7 |
| 14.4 | 6.16 | 17 |
| 15.8 | 5.62 | 25 |
| 16.1 | 5.51 | 80 |
| 16.7 | 5.30 | 100 |
| 17.0 | 5.20 | 26 |
| 18.3 | 4.84 | 96 |
| 19.1 | 4.65 | 28 |
| 20.0 | 4.44 | 21 |
| 20.3 | 4.37 | 63 |
| 20.8 | 4.28 | 45 |
| 21.3 | 4.17 | 20 |
| 21.6 | 4.11 | 11 |
| 22.6 | 3.94 | 26 |
| 23.1 | 3.85 | 46 |
| 23.3 | 3.81 | 59 |
| 23.5 | 3.79 | 29 |
| 23.7 | 3.75 | 20 |
| 23.9 | 3.71 | 25 |
| 24.2 | 3.68 | 34 |
| 24.6 | 3.62 | 15 |
| 25.3 | 3.52 | 56 |
| 25.9 | 3.44 | 29 |
| 26.3 | 3.39 | 25 |
| 26.5 | 3.36 | 23 |
| 27.0 | 3.30 | 12 |

TABLE 5-continued

| 2-theta (deg) | d-spacing (Å) | Relative Intensity (I) |
| --- | --- | --- |
| 27.8 | 3.21 | 33 |
| 28.3 | 3.15 | 4 |
| 29.0 | 3.08 | 14 |
| 29.6 | 3.02 | 8 |
| 30.6 | 2.92 | 9 |
| 31.0 | 2.89 | 7 |
| 31.4 | 2.85 | 7 |
| 31.7 | 2.82 | 11 |
| 32.2 | 2.78 | 4 |
| 32.5 | 2.75 | 13 |

5.3 XRPD Pattern Indexing of the 1:1 Psilocin Fumarate Salt, 5

The XRPD indexing description, FIG. 22, shows a primitive monoclinic crystal system with a space group of P2$_1$/n (14). The unit cell parameters are a=7.441 Å, b=8.877 Å, c=25.707 Å, α=90°, β=93.34°, γ=90° with a unit cell volume of 1695.2 Å$^3$.

5.4 DSC of the 1:1 Psilocin Fumarate Salt, 5

The differential scanning calorimetry (DSC) trace, FIG. 23, shows a significant endotherm with a peak maximum of about 167° C. corresponding to the melt of the salt.

5.5 TGA of the 1:1 Psilocin Fumarate Salt, 5

The thermal gravimetric analysis (TGA) trace, FIG. 24, shows a negligible weight loss of less than 0.4% prior to the salt melt onset temperature near 166° C.

5.6 $^1$H NMR Spectrum of the 1:1 Psilocin Fumarate Salt, 5

The $^1$H NMR spectrum of the 1:1 psilocin fumarate salt shown in FIG. 25 displays the following peaks: $^1$H NMR (600 MHz, CD$_3$OD) δ: 7.02 (1H), 6.84-6.92 (2H), 6.69 (2H), 6.38-6.36 (1H), 3.49 (2H), 3.28 (2H), 2.90 (6H). The multiplet at 6.38-6.36 ppm in the $^1$H NMR spectrum corresponds to 1 proton of psilocin. Comparison of the integration of this peak with the singlet at 6.69 ppm, which corresponds to the two protons of fumaric acid, indicates that the salt has a psilocin:fumarate stoichiometry of 1:1.

Example 6: 2:1 Psilocin Hemifumarate Salt, 6

6.1 Preparation of the 2:1 Psilocin Hemifumarate Salt, 6

A solution of 90.8 mg of psilocin (Cayman Chemical, lot 0594443) in 2 mL of acetone (Fisher Scientific, lot 494118) was decolorized with activated charcoal and filtered through a 0.2-μm nylon filter. The room-temperature solution was added to a 60° C. suspension, containing 51.1 mg of fumaric acid (Sigma Aldrich, lot MKBB7131) in 3 mL of acetone (Fisher Scientific, lot 494118), resulting in oil. The oily suspension was seeded with 1:1 psilocin fumarate salt 5 and sonicated for 30 seconds, providing precipitation. The precipitant was isolated by water aspirated vacuum filtration, rinsed with 2 mL of acetone (Fisher Scientific, lot 494118), and briefly dried under a nitrogen purge.

6.2 XRPD Characterization of the 2:1 Psilocin Hemifumarate Salt, 6

The experimental XRPD pattern of the 2:1 psilocin hemifumarate salt 6 is shown in FIG. 26. Table 6 lists the angles, ° 2θ±0.2° 2θ, and d-spacing of the peaks identified in the experimental XRPD pattern of FIG. 26. The entire list of peaks, or a subset thereof, may be sufficient to characterize the salt, as well as by an XRPD pattern substantially similar (that is, identifiable by one of ordinary skill using this method within experimental variations) to FIG. 26. For example, a 2:1 psilocin hemifumarate salt of the invention may be characterized by a powder X-ray diffraction pattern having at least three, four, or five peaks selected from 9.7, 13.7, 16.1, 16.6, 23.9, 24.7, and 25.2° 2θ±0.2° 2θ. Additional peaks near 10.5, 12.6, 18.3, 19.1, and 20.8° 2θ are consistent with the peaks corresponding to the 1:1 psilocin fumarate component, and were therefore not attributed to 2:1 psilocin fumarate.

TABLE 6

| 2-theta (deg) | d-spacing (Å) | Relative Intensity (I) |
|---|---|---|
| 9.7 | 9.11 | 11 |
| 11.3 | 7.85 | 7 |
| 12.2 | 7.23 | 7 |
| 13.7 | 6.48 | 15 |
| 16.1 | 5.51 | 55 |
| 16.6 | 5.35 | 54 |
| 17.2 | 5.15 | 1 |
| 19.9 | 4.47 | 9 |
| 20.1 | 4.41 | 7 |
| 21.5 | 4.13 | 8 |
| 22.7 | 3.92 | 3 |
| 23.3 | 3.82 | 4 |
| 23.9 | 3.72 | 23 |
| 24.7 | 3.61 | 100 |
| 25.2 | 3.54 | 11 |
| 26.2 | 3.40 | 2 |
| 27.9 | 3.20 | 6 |
| 28.5 | 3.13 | 2 |
| 28.9 | 3.08 | 4 |
| 29.4 | 3.03 | 6 |
| 29.7 | 3.00 | 2 |
| 30.0 | 2.97 | 2 |
| 30.2 | 2.96 | 2 |
| 30.7 | 2.91 | 1 |
| 31.8 | 2.81 | 1 |
| 32.1 | 2.79 | 2 |
| 32.7 | 2.74 | 5 |

6.3 XRPD Pattern Indexing of the 2:1 Psilocin Hemifumarate Salt, 6

The XRPD indexing description, FIG. 27, shows a triclinic crystal system with space groups of P1(1) or P$\bar{1}$ (2). The unit cell parameters are a=8.118 Å, b=9.361 Å, c=9.396 Å, α=101.03°, β=96.64°, γ=102.18° with a unit cell volume of 676.0 Å$^3$.

6.4 DSC of the 2:1 Psilocin Hemifumarate Salt, 6

The differential scanning calorimetry (DSC) trace, FIG. 28, shows minor endotherms near 149 and 166° C. The weak endotherm observed near 166° C. is consistent with the melt of the 1:1 psilocin fumarate component. The final endotherm with the onset of about 225° C. has been attributed to the melt of 2:1 psilocin hemifumarate.

6.5 TGA of the 2:1 Psilocin Hemifumarate Salt, 6

The thermal gravimetric analysis (TGA) trace, FIG. 29, shows no significant weight loss prior to the salt melt temperature near 225° C.

6.6 $^1$H NMR Spectrum of the 2:1 Psilocin Hemifumarate Salt, 6

The $^1$H NMR spectrum of the 2:1 psilocin hemifumarate salt shown in FIG. 30 displays the following peaks: $^1$H NMR (600 MHz, CD$_3$OD) δ: 6.99 (1H), 6.90-6.83 (2H), 6.69 (1H), 6.37-6.36 (1H), 3.40 (2H), 3.25 (2H), and 2.83 (6H). The multiplet at 6.37-6.36 ppm in the $^1$H NMR spectrum corresponds to 1 proton of psilocin. Comparison of the integration of this peak with the singlet at 6.69 ppm, which corresponds to protons of fumaric acid, indicates that the salt has a psilocin:fumarate stoichiometry of 2:1.

Example 7: A Solvate of the 1:1 Psilocin Oxalate Salt, 7

7.1 Preparation of the Solvate of the 1:1 Psilocin Oxalate Salt, 7

A solution of 216.5 mg of psilocin (Cayman Chemical, lot 0594443) in 15 mL of 80:20 v/v diethyl ether/ethanol (Sigma Aldrich; lots SHBL6577 and SHBK9943, respectively) was decolorized with activated charcoal and filtered through a 0.2-μm nylon filter. A 5 mL aliquot of the clear solution was added to 31.3 mg of oxalic acid (Sigma Aldrich, lot SHBC7057V), providing a turbid suspension. The suspension was slurried for a day at room temperature. The precipitant was isolated by water aspirated vacuum filtration.

7.2 XRPD Characterization of the Solvate of the 1:1 Psilocin Oxalate Salt, 7

The experimental XRPD pattern of the solvate of the 1:1 psilocin oxalate salt, 7 is shown in FIG. 31. Table 7 lists the angles, ° 2θ±0.2° 2θ, and d-spacing of the peaks identified in the experimental XRPD pattern of FIG. 31. The entire list of peaks, or a subset thereof, may be sufficient to characterize the salt, as well as by an XRPD pattern substantially similar (that is, identifiable by one of ordinary skill using this method within experimental variations) to FIG. 31. For example, a solvate of the 1:1 psilocin oxalate salt of the invention may be characterized by a powder X-ray diffraction pattern having at least three, four, or five peaks selected from 7.6, 7.8, 10.3, 14.2, 15.3, 15.7, 17.1, 19.5, 20.4, 20.6, 21.0, 21.7, 22.9, 23.7, 24.1, 24.3, 24.8, and 27.1° 2θ±0.2° 2θ.

TABLE 7

| 2-theta (deg) | d-spacing (Å) | Relative Intensity (I) |
|---|---|---|
| 7.6 | 11.56 | 33 |
| 7.8 | 11.28 | 70 |
| 10.3 | 8.62 | 14 |
| 13.7 | 6.45 | 4 |
| 14.2 | 6.22 | 28 |
| 15.3 | 5.78 | 30 |
| 15.7 | 5.63 | 75 |
| 17.1 | 5.18 | 29 |
| 18.0 | 4.94 | 11 |
| 18.3 | 4.84 | 13 |
| 19.5 | 4.54 | 42 |
| 20.4 | 4.35 | 21 |
| 20.6 | 4.31 | 17 |
| 21.0 | 4.23 | 100 |
| 21.7 | 4.10 | 19 |
| 22.9 | 3.88 | 67 |
| 23.4 | 3.81 | 9 |
| 23.7 | 3.75 | 25 |
| 24.1 | 3.69 | 26 |
| 24.3 | 3.66 | 33 |
| 24.8 | 3.59 | 30 |
| 25.8 | 3.45 | 12 |
| 26.3 | 3.39 | 4 |
| 26.6 | 3.35 | 4 |
| 27.1 | 3.29 | 22 |
| 27.7 | 3.22 | 6 |
| 27.9 | 3.19 | 5 |
| 28.7 | 3.10 | 6 |
| 29.3 | 3.05 | 3 |
| 30.0 | 2.97 | 9 |
| 30.4 | 2.93 | 4 |

7.3 XRPD Pattern Indexing of the Solvate of the 1:1 Psilocin Oxalate Salt, 7

The XRPD indexing description, FIG. 32, shows a primitive monoclinic crystal system with a space group of P2$_1$/n (14). The unit cell parameters are a=5.690 Å, b=12.894 Å, c=23.273 Å, α=90°, β=96.83°, γ=90° with a unit cell volume of 1695.3 Å$^3$.

The XRPD pattern of 7 was successfully indexed by a single unit cell and provides strong evidence that the pattern is representative of a single crystalline phase. The unit cell likely contains four psilocin cations and four oxalic acid anions. Consequently, the formula unit volume of 424 Å$^3$ calculated from the indexing results could provide approximately 58 Å$^3$ of free volume that could partially accommodate solvent.

7.4 DSC of the Solvate of the 1:1 Psilocin Oxalate Salt, 7

The differential scanning calorimetry (DSC) trace, FIG. 33, shows multiple endothermic events between 80 and 160° C. likely due to the volatilization of the solvent.

7.5 TGA of the Solvate of the 1:1 Psilocin Oxalate Salt, 7

The thermal gravimetric analysis (TGA) trace, FIG. 34, shows a weight loss of approximately 6% up to 149° C. which is likely to be the loss of diethyl ether and ethanol solvent that are part of the crystal lattice. The weight loss is consistent with the combined volatilization of 0.2 and 0.1 mol/mol of diethyl ether and ethanol, respectively.

7.6 $^1$H NMR Spectrum of the Solvate of the 1:1 Psilocin Oxalate Salt, 7

The $^1$H NMR spectrum shown in FIG. 35 displays the following peaks: $^1$H NMR (600 MHz, CD$_3$OD) δ: 7.02 (1H), 6.84-6.90 (2H), 6.36-6.37 (1H), 3.47-3.51 (2H), 3.27-3.29 (2H), and 2.90 (6H). The multiplet at 6.36-6.37 ppm in the $^1$H NMR spectrum corresponds to 1 proton of psilocin. Comparison of the integration of the multiplet at 6.36-6.37 ppm, which corresponds to 1 proton of psilosin, to the solvent peaks indicates that the salt contains approximately 0.2 and 0.1 mol/mol of diethyl ether and ethanol, respectively. 7.7 Ion Chromatography of the Solvate of the 1:1 Psilocin Oxalate Salt, 7

The ion chromatography technique described above was used to analyze the samples for anion content and to quantitate multiple anions in the sample. The ion chromatography analysis of the solvate of the 1:1 psilocin oxalate salt 7 revealed the presence of the oxalate ion and indicates that the salt is a mono-oxalate.

Example 8: 1:1 Psilocin DL-Lactate Salt, 8

8.1 Preparation of the 1:1 Psilocin DL-Lactate Salt, 8

In a 1-dram glass vial were combined 24.7 mg of psilocin (Cayman Chemical) and 5 mL of diethylether. Complete dissolution was observed. Activated charcoal was added to the vial. The sample was then sonicated and filtered through a 0.45 μm filter into a vial containing 12.0 mg of D,L-lactic acid (1 molar equivalent). White solids formed and the sample was stirred at 50° C. for 4 days. The sample was cooled to room temperature and centrifuged followed by decantation of the supernatant. Solids were air dried.

8.2 XRPD Characterization of the 1:1 Psilocin DL-Lactate Salt, 8

The experimental XRPD pattern of the 1:1 psilocin DL-lactate salt 8 is shown in FIG. 36. Table 8 lists the angles, ° 2θ±0.2° 2θ, and d-spacing of the peaks identified in the experimental XRPD pattern of FIG. 36. The entire list of peaks, or a subset thereof, may be sufficient to characterize the salt, as well as by an XRPD pattern substantially similar (that is, identifiable by one of ordinary skill using this method within experimental variations) to FIG. 36. For example, a 1:1 psilocin DL-lactate salt of the invention may be characterized by a powder X-ray diffraction pattern having at least three, four, or five peaks selected from 9.0, 13.8, 14.4, 15.6, 17.8, 18.4, 20.3, 21.7, 22.3, 22.9, 24.0, and 25.5° 2θ±0.2° 2θ.

TABLE 8

| 2-theta (deg) | d-spacing (Å) | Relative Intensity (I) |
| --- | --- | --- |
| 9.0 | 9.81 | 88 |
| 12.9 | 6.87 | 5 |
| 13.8 | 6.41 | 9 |

TABLE 8-continued

| 2-theta (deg) | d-spacing (Å) | Relative Intensity (I) |
| --- | --- | --- |
| 14.4 | 6.14 | 11 |
| 15.1 | 5.86 | 7 |
| 15.6 | 5.69 | 87 |
| 17.8 | 4.98 | 45 |
| 18.1 | 4.90 | 60 |
| 18.4 | 4.82 | 36 |
| 19.7 | 4.50 | 28 |
| 19.9 | 4.45 | 13 |
| 20.3 | 4.38 | 16 |
| 21.0 | 4.24 | 11 |
| 21.7 | 4.08 | 18 |
| 22.3 | 3.99 | 25 |
| 22.6 | 3.94 | 7 |
| 22.9 | 3.88 | 31 |
| 23.2 | 3.84 | 18 |
| 24.0 | 3.71 | 100 |
| 24.3 | 3.66 | 12 |
| 25.1 | 3.55 | 7 |
| 25.5 | 3.49 | 45 |
| 26.0 | 3.43 | 12 |
| 26.4 | 3.37 | 8 |
| 26.7 | 3.34 | 8 |
| 27.3 | 3.27 | 10 |
| 27.9 | 3.20 | 13 |
| 28.9 | 3.09 | 11 |
| 29.3 | 3.05 | 10 |

8.3 XRPD Pattern Indexing of the 1:1 Psilocin DL-Lactate Salt, 8

The XRPD indexing description, FIG. 37, shows a primitive monoclinic crystal system with a space group of P2$_1$/c (14). The unit cell parameters are a=11.787 Å, b=8.473 Å, c=18.455 Å, α=90°, β=56.30°, γ=90° with a unit cell volume of 1533.5 Å$^3$.

8.4 DSC of the 1:1 Psilocin DL-Lactate Salt, 8

The differential scanning calorimetry (DSC) trace, FIG. 38, shows a single endotherm with a peak maximum of about 148° C. corresponding to concomitant melt/decomposition of the salt.

8.5 TGA of the 1:1 Psilocin DL-Lactate Salt, 8

The thermal gravimetric analysis (TGA) trace, FIG. 39, shows a weight loss of 1.7% below 135° C., likely due to loss of DL-lactic acid (boiling point is approximately 122° C.).

8.6 $^1$H NMR Spectrum of the 1:1 Psilocin DL-Lactate Salt, 8

The $^1$H NMR spectrum of the 1:1 psilocin DL-lactate salt shown in FIG. 40 displays the following peaks: $^1$H NMR (400 MHz, DMSO-D$_6$) δ: 10.61 (1H), 6.93 (1H), 6.73-6.81 (2H), 6.27 (1H), 3.90-3.95 (1H), 2.93 (2H), 2.70 (2H), 2.34 (6H), and 1.19 (3H). The multiplet at 6.27 ppm in the $^1$H NMR spectrum corresponds to 1 proton of psilocin. Comparison of the integration of this peak with the multiplet at 1.19 ppm, which corresponds to the 3 protons of the methyl group of DL-lactic acid, indicates that the salt has a psilocin: DL-lactate stoichiometry of 1:1.

Example 9: 1:1 Psilocin L-Malate Salt, 9

9.1 Preparation of the 1:1 Psilocin L-Malate Salt, 9

In a 1-dram glass vial were combined 24.7 mg of psilocin (Cayman Chemical) and 1 mL of methyl ethyl ketone. Complete dissolution was observed. Activated charcoal was added to the vial. The sample was then sonicated and filtered through a 0.45 μm filter into a new vial containing 16.2 mg of L-malic acid (1 molar equivalent). The sample was stirred at room temperature for 7 days. The sample was centrifuged followed by decantation of the supernatant. Solids were air dried.

9.2 XRPD Characterization of the 1:1 Psilocin L-Malate Salt, 9

The experimental XRPD pattern of the 1:1 psilocin L-malate salt 9 is shown in FIG. 41. Table 9 lists the angles, ° 2θ±0.2° 2θ, and d-spacing of the peaks identified in the experimental XRPD pattern of FIG. 41. The entire list of peaks, or a subset thereof, may be sufficient to characterize the salt, as well as by an XRPD pattern substantially similar (that is, identifiable by one of ordinary skill using this method within experimental variations) to FIG. 41. For example, a 1:1 psilocin L-malate salt of the invention may be characterized by a powder X-ray diffraction pattern having at least three peaks selected from 8.6, 9.0, 11.7, 12.6, 15.9, 16.8, 18.1, 20.2, 20.6, 21.4, 22.8, 26.1 and 28.0° 2θ±0.2° 2θ.

TABLE 9

| 2-theta (deg) | d-spacing (Å) | Relative Intensity (I) |
|---|---|---|
| 8.6 | 10.25 | 10 |
| 9.0 | 9.80 | 15 |
| 11.7 | 7.55 | 13 |
| 12.3 | 7.18 | 9 |
| 12.6 | 7.00 | 18 |
| 14.2 | 6.25 | 19 |
| 14.7 | 6.03 | 28 |
| 15.9 | 5.58 | 26 |
| 16.5 | 5.38 | 27 |
| 16.8 | 5.27 | 35 |
| 17.3 | 5.13 | 28 |
| 17.8 | 4.98 | 44 |
| 18.1 | 4.90 | 100 |
| 18.9 | 4.69 | 58 |
| 19.5 | 4.54 | 27 |
| 20.2 | 4.40 | 65 |
| 20.6 | 4.32 | 48 |
| 21.4 | 4.14 | 44 |
| 22.1 | 4.03 | 11 |
| 22.8 | 3.91 | 19 |
| 23.5 | 3.79 | 54 |
| 24.0 | 3.71 | 18 |
| 24.3 | 3.66 | 11 |
| 24.8 | 3.59 | 12 |
| 25.4 | 3.50 | 9 |
| 26.1 | 3.41 | 37 |
| 26.7 | 3.34 | 10 |
| 27.3 | 3.27 | 35 |
| 28.0 | 3.19 | 35 |
| 28.6 | 3.12 | 9 |
| 29.6 | 3.02 | 9 |
| 29.8 | 3.00 | 10 |
| 30.2 | 2.96 | 9 |
| 30.7 | 2.91 | 12 |
| 31.1 | 2.88 | 8 |

9.3 XRPD Pattern Indexing of the 1:1 Psilocin L-Malate Salt, 9

The XRPD indexing description, FIG. 42, shows a primitive monoclinic crystal system with a space group of P2$_1$ (4). The unit cell parameters are a=7.558 Å, b=11.151 Å, c=20.520 Å, α=90°, β=92.15°, γ=90° with a unit cell volume of 1728.3 Å$^3$.

9.4 DSC of the 1:1 Psilocin L-Malate Salt, 9

The differential scanning calorimetry (DSC) trace, FIG. 43, shows a single endotherm with a peak maximum of about 129° C. corresponding to the melt of the salt.

9.5 TGA of the 1:1 Psilocin L-Malate Salt, 9

The thermal gravimetric analysis (TGA) trace, FIG. 44, shows no significant weight loss up to near 125° C.

9.6 $^1$H NMR Spectrum of the 1:1 Psilocin L-Malate Salt, 9

The $^1$H NMR spectrum of the 1:1 psilocin L-malate salt shown in FIG. 45 displays the following peaks: $^1$H NMR (400 MHz, DMSO-D$_6$) δ: 10.73 (1H), 7.01 (1H), 6.80-6.84 (2H), 6.32 (1H), 3.92 (1H), 3.07-3.14 (4H), 2.67 (6H), and 2.30-2.35 (1H). The multiplet at 6.32 ppm in the $^1$H NMR spectrum corresponds to 1 proton of psilocin. Comparison of the integration of this peak with the multiplet at 3.92 ppm, which corresponds to the 1 proton of the malic acid, indicating that the salt has a psilocin:malate stoichiometry of 1:1.

Example 10: 1:1 Psilocin Stearate Salt, 10

10.1 Preparation of the 1:1 Psilocin Stearate Salt, 10

In a PEEK grinding cup were combined 24.7 mg of psilocin (Cayman Chemical) and 33.8 mg of stearic acid (1 molar equivalent). Ten micro liters of 50:50 methyl tertiary-butyl ether/hexane and a stainless-steel ball were added to the cup. The PEEK grinding cup was capped and placed on a Retsch Mill MM200 and milled at 100% power for 30 minutes. The resulting solids were recovered and analyzed.

10.2 XRPD Characterization of the 1:1 Psilocin Stearate Salt, 10

The experimental XRPD pattern of the 1:1 psilocin stearate salt 10 is shown in FIG. 46. Table 10 lists the angles, ° 2θ±0.2° 2θ, and d-spacing of the peaks identified in the experimental XRPD pattern of FIG. 46. The entire list of peaks, or a subset thereof, may be sufficient to characterize the salt, as well as by an XRPD pattern substantially similar (that is, identifiable by one of ordinary skill using this method within experimental variations) to FIG. 46. For example, a 1:1 psilocin stearate salt of the invention may be characterized by a powder X-ray diffraction pattern having at least three peaks selected from 4.5, 8.9, 14.4, 15.6, 20.1, 21.0, 23.9, and 26.4° 2θ±0.2° 2θ.

TABLE 10

| 2-theta (deg) | d-spacing (Å) | Relative Intensity (I) |
|---|---|---|
| 4.5 | 19.83 | 100 |
| 8.9 | 9.92 | 21 |
| 11.5 | 7.67 | 6 |
| 11.9 | 7.43 | 7 |
| 13.4 | 6.61 | 12 |
| 13.6 | 6.50 | 15 |
| 13.9 | 6.38 | 13 |
| 14.4 | 6.16 | 39 |
| 15.6 | 5.67 | 14 |
| 16.3 | 5.45 | 34 |
| 16.6 | 5.34 | 32 |
| 17.5 | 5.05 | 21 |
| 17.9 | 4.96 | 26 |
| 18.6 | 4.76 | 16 |
| 19.2 | 4.62 | 16 |
| 20.1 | 4.42 | 63 |
| 20.6 | 4.31 | 12 |
| 21.0 | 4.24 | 32 |
| 21.3 | 4.18 | 19 |
| 21.5 | 4.12 | 13 |
| 22.6 | 3.93 | 53 |
| 23.2 | 3.84 | 55 |
| 23.9 | 3.73 | 96 |
| 24.6 | 3.62 | 16 |
| 25.2 | 3.54 | 8 |
| 25.8 | 3.45 | 10 |
| 26.4 | 3.38 | 48 |
| 27.5 | 3.24 | 7 |
| 27.8 | 3.20 | 7 |
| 28.9 | 3.09 | 7 |
| 29.3 | 3.05 | 6 |
| 29.8 | 3.00 | 6 |
| 30.4 | 2.94 | 11 |

10.3 XRPD Pattern Indexing of the 1:1 Psilocin Stearate Salt, 10

The XRPD indexing description, FIG. 47, shows a primitive triclinic crystal system with a space group of P1 (1) or P-1 (2). The unit cell parameters are a=7.726 Å, b=11.747 Å, c=20.293 Å, α=77.79°, β=96.28°, γ=122.75° with a unit cell volume of 1513.96 Å$^3$.

10.4 DSC of the 1:1 Psilocin Stearate Salt, 10

The differential scanning calorimetry (DSC) trace, FIG. 48, shows a single endotherm with a peak maximum of about 86° C. corresponding to the melt of the salt.

10.5 TGA of the 1:1 Psilocin Stearate Salt, 10

The thermal gravimetric analysis (TGA) trace, FIG. 49, shows no significant weight loss up to 85° C.

10.6 $^1$H NMR Spectrum of the 1:1 Psilocin Stearate Salt, 10

The $^1$H NMR spectrum of the 1:1 psilocin stearate salt shown in FIG. 50 displays the following peaks: $^1$H NMR (400 MHz, DMSO-D$_6$) δ: 10.58 (1H), 6.90 (1H), 6.72-6.80 (2H), 6.25 (1H), 2.87 (2H), 2.55 (2H), 2.22 (6H), 2.17 (2H), 1.46 (2H), 1.23 (29H), and 0.85 (3H). The multiplet at 6.25 ppm in the $^1$H NMR spectrum corresponds to 1 proton of psilocin. Comparison of the integration of this peak with the multiplet at 0.85 ppm, which corresponds to the 3 protons of the methyl group of stearic acid, indicates that the salt has a psilocin: stearate stoichiometry of 1.1.

What is claimed is:

1. A crystalline form of a salt or cocrystal of stearic acid and psilocin (4-hydroxy-N,N-dimethyltryptamine) having about a 1:1 stoichiometry, and, exhibiting an X-ray powder diffraction pattern having at least three peaks at the following 2θ diffraction angles: 4.5, 8.9, 14.4, 15.6, 20.1, 21.0, 23.9, and 26.4° 2θ±0.2° 2θ.

2. The crystalline form of claim 1, wherein the crystalline form has an X-ray powder diffraction pattern as shown in FIG. 46.

3. The crystalline form of claim 1, wherein the crystalline form comprises a crystal having unit cell parameters substantially equal to the following:

| Crystal system | Primitive monoclinic |
|---|---|
| Space group | P1 (1) or P-7 (2) |
| Unit cell parameters | |
| a = 7.726 Å | α = 77.79° |
| b = 11.747 Å | β = 96.28° |
| c = 20.293 Å | γ = 122.75° |
| Unit cell volume (Å$^3$) | 1513.96. |

4. The crystalline form of claim 1, wherein the crystalline form further exhibits one or more of the following characteristics:
   an endothermic event having a peak maximum at about 86° C., measured by differential scanning calorimetry;
   a thermogravimetric analysis thermogram as shown in FIG. 49; or
   a solution $^1$H NMR spectrum in d$_6$-DMSO comprising one or more chemical shift peaks at about 0.9 ppm, 1.2 ppm, 1.5 ppm, 2.2 ppm, 2.6 ppm, 2.9 ppm, 6.3 ppm, 6.7 ppm, 6.8 ppm, 6.9 ppm, and 10.6 ppm.

5. The crystalline form of claim 4, wherein the crystalline form has a differential scanning calorimetry thermogram as shown in FIG. 48.

6. The crystalline form of claim 4, wherein the crystalline form has a solution $^1$H NMR spectrum in d$_6$-DMSO comprising at least the characteristic chemical shift peaks at about 6.3 ppm and about 0.9 ppm.

7. The crystallien form of claim 4, wherein the crystalline form has a solution $^1$H NMR spectrum as shown in FIG. 50.

8. A pharmaceutical composition comprising the crystalline form of claim 1, and at least one pharmaceutically acceptable carrier.

9. The pharmaceutical composition of claim 8, wherein the pharmaceutical composition is an oral formulation.

10. The pharmaceutical composition of claim 9, wherein the pharmaceutical composition is in an oral solid dosage form.

11. A method for preparing a the crystalline form of claim 1, comprising:
    reacting psilocin with stearic acid, to precipitate the salt or cocrystal of psilocin and stearic acid in a crystalline form.

12. The method of claim 11, further comprising:
    dissolving or suspending or grinding the psilocin and/or the acid in an organic solvent selected from the group consisting of an alcohol, ether, ketone, alkane, and a mixture thereof.

13. The method of claim 12, wherein the organic solvent is diethyl ether, isopropyl alcohol, acetone, ethanol, methyl ethyl ketone, methyl tertiary-butyl ether, hexaone, or a mixture thereof.

14. The method of claim 13, wherein the organic solvent is a mixture of methyl tertiary-butyl ether, and hexane.

15. The method of claim 14, wherein the organic solvent is a 50:50 mixture of methyl tertiary-butyl ether:hexane.

16. A method of treating a disease or disorder in a subject in need thereof, comprising:
    administering to the subject in need thereof a therapeutically effective amount of the crystallien form of claim 1, wherein the disease or disorder is a psychiatric or psychotic disorder, a neurocognitive disease or disorder, autism spectrum disorder (ASD), chronic pain, inflammatory disease or disorder, stroke, epilepsy disorder, amyotrophic lateral sclerosis (ALS), or combinations thereof.

17. The method of claim 16, wherein the disease or disorder is a psychiatric or psychotic disorder selected from the group consisting of attention-deficit hyperactivity disorder (ADHD), anxiety disorder, sleep-wake disorder, impulse-control disorder, disruptive behavior, conduct disorder, depressive disorder, major depressive disorder (MDD), post-traumatic stress disorder (PTSD), obsessive-compulsive and related disorder, bipolar disorder, schizophrenia, and combinations thereof.

18. The method of claim 16, wherein the disease or disorder is a neurocognitive disease or disorder selected from the group consisting of Alzheimer's disease; Lewy Body Dementia; Traumatic Brain Injury; Prion Disease; HIV Infection; Parkinson's disease; Huntington's disease; and combinations thereof.

* * * * *